United States Patent
Baeschlin et al.

(10) Patent No.: US 7,851,642 B2
(45) Date of Patent: Dec. 14, 2010

(54) δ-AMINO-γ-HYDROXY-ω-ARYL-ALKANOIC ACID AMIDE COMPOUND

(75) Inventors: Daniel Kaspar Baeschlin, Arlesheim (CH); Juergen Klaus Maibaum, Weil-Haltingen (DE); Holger Sellner, Therwil (DE)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 12/483,582

(22) Filed: Jun. 12, 2009

(65) Prior Publication Data
US 2009/0253701 A1 Oct. 8, 2009

Related U.S. Application Data

(63) Continuation of application No. 10/579,427, filed as application No. PCT/EP2004/013412 on Nov. 25, 2004, now Pat. No. 7,582,782.

(60) Provisional application No. 60/525,374, filed on Nov. 26, 2003.

(51) Int. Cl.
C07C 233/05 (2006.01)
A61K 31/65 (2006.01)

(52) U.S. Cl. .............. 554/35; 554/61; 554/65; 564/155; 564/164; 514/558; 514/563; 514/616; 514/620

(58) Field of Classification Search .......... 514/558, 514/563, 616, 620; 564/155, 164; 554/35, 554/61, 65
See application file for complete search history.

(56) References Cited

U.S. PATENT DOCUMENTS

| | | | | |
|---|---|---|---|---|
| 5,559,111 A * | 9/1996 | Goschke et al. | ......... | 514/227.5 |
| 5,606,078 A | 2/1997 | Goschke et al. | | |
| 5,627,182 A | 5/1997 | Goschke et al. | | |
| 5,646,143 A | 7/1997 | Goschke et al. | | |
| 5,705,658 A | 1/1998 | Goschke et al. | | |
| 7,582,782 B2 * | 9/2009 | Baeschlin et al. | ............. | 554/35 |

FOREIGN PATENT DOCUMENTS

WO 02/40007 A 5/2002
WO 03/103653 A 12/2003

OTHER PUBLICATIONS

Wood et al, Biochemical and Biophysical Research Communications 308, pp. 698-705, Structure-based design of aliskiren, a novel orally effective rennin inhibitor. (2003).
Goeschke et al. Bioorganic 8 Medicinal Chemistry Letters, vol. 7, No. 21, pp. 2735-2740, Design and Synthesis of Novel 2.7-Dialkyl. Substituted 5(S)-Amino-4(S)-H-y~--8-Phenyl-Octanecarboxamides as in Vitro Potent Peptidomeimetic inhibitors of Human Renin, (1997).
Rahuel et al, Chemistry & Biology, 2000, vol. 7, No. 7, pp. 493-504.

* cited by examiner

*Primary Examiner*—Shailendra Kumar
(74) *Attorney, Agent, or Firm*—Sophie Binet Cross

(57) ABSTRACT

Disclosed are δ-amino-γ-hydroxy-ω-aryl-alkanoic acid amide compounds of formula (I)

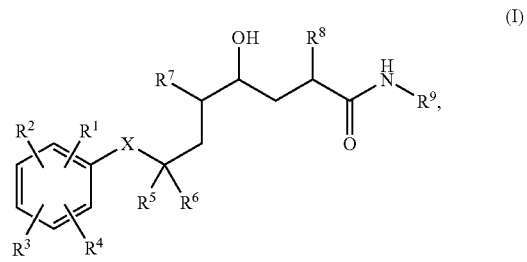

and the salts thereof, having renin-inhibiting properties. Also disclosed are pharmaceutical compositions comprising these compounds and methods of administering them for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

21 Claims, No Drawings

δ-AMINO-γ-HYDROXY-ω-ARYL-ALKANOIC ACID AMIDE COMPOUND

This application is a Continuation of U.S. application Ser. No. 10/579,427 filed May 12, 2006 which is a National Stage Entry of International Application PCT/EP04/13412 filed Nov. 25, 2004 which claims priority to U.S. Provisional Application No. 60/525,374 filed Nov. 26, 2003.

The invention relates to novel δ-amino-γ-hydroxy-ω-aryl-alkanoic acid amides of formula (I)

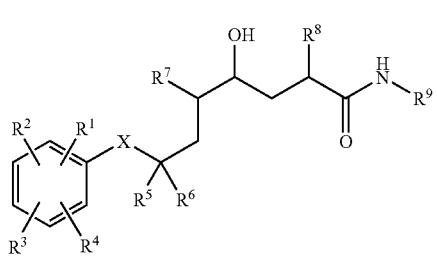

wherein
- $R^1$ is hydrogen, halogen, optionally halogenated alkyl, cycloalkyl, hydroxy, optionally halogenated alkoxy, cycloalkoxy, lower alkoxy-lower alkoxy or free or esterified or amidated carboxy-lower alkoxy or lower alkyl;
- $R^2$ is hydrogen, halogen, optionally halogenated lower alkyl, hydroxy, cycloalkyl, cycloalkoxy, optionally halogenated lower alkoxy-lower alkyl, optionally substituted lower alkoxy-lower alkyl, cycloalkoxy-lower alkyl; optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl, optionally hydrogenated heteroaryl-lower alkyl, amino-lower alkoxy that is substituted by lower alkyl, by lower alkanoyl and/or by lower alkoxycarbonyl; oxo-lower alkoxy, lower alkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl lower alkoxy, optionally S-oxidised lower alkylthio-lower alkoxy, lower alkylthio-(hydroxy)-lower alkoxy, aryl-lower alkoxy, aryl-lower alkyl, aryl-lower alkoxy, optionally hydrogenated heteroaryl-lower alkoxy, optionally hydrogenated heteroaryl-lower alkyl, cyano-lower alkoxy, cyano-lower alkyl, free or esterified or amidated carboxy-lower alkoxy or free or esterified or amidated carboxy-lower alkyl;
- $R^3$ and $R^4$ are independently hydrogen, halogen, optionally halogenated lower alkyl, hydroxy, optionally halogenated lower alkoxy or cycloalkoxy, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene, cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene, cyano-lower alkoxy or free or esterified or amidated carboxy-lower alkoxy; or
- $R^4$ together with $R_3$ is lower alkeneoxy, lower alkylenedioxy or a fused-on aryl, optionally hydrogenated heteroaryl or cycloalkyl ring;
- X is methylene, hydroxymethylene, oxygen, optionally lower alkyl substituted nitrogen, optionally oxidized sulfur;
- $R^5$ is lower alkyl or cycloalkyl;
- $R^6$ is hydrogen, lower alkyl, hydroxy, alkoxy or halogen;
- $R^7$ is unsubstituted or N-mono- or N,N-di-lower alkylated or N-lower alkanoylated amino;
- $R^8$ is lower alkyl, lower alkenyl, cycloalkyl or aryl-lower alkyl;
- $R^9$ is optionally substituted lower alkyl, optionally substituted cycloalkyl, optionally substituted cycloalkyl-alkyl, cycloalkyl carboxamides, N-mono or N,N-dialkyl substituted cycloalkyl carboxamides, optionally substituted aryl-alkyl, optionally substituted aryloxy-aryl, optionally substituted heteroaryloxy-alkyl, free or aliphatically esterified or etherified hydroxy-lower alkyl; amino-lower alkyl that is unsubstituted or N-lower alkanoylated or N-mono- or N,N-di-lower alkylated or N,N-di-substituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene, free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted;

and to pharmaceutically acceptable salts thereof, to processes for the preparation of the compounds according to the invention, to pharmaceutical compositions containing them and to their use as medicinal active ingredients.

The compounds of the present invention exhibit inhibitory activity on the natural enzyme renin. Thus, compounds of formula (I) may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Listed below are definitions of various terms used to describe the compounds of the present invention. These definitions apply to the terms as they are used throughout the specification unless they are otherwise limited in specific instances either individually or as part of a larger group.

Aryl and aryl in aryl-alkyl, aryl-lower alkoxy, aryl-lower alkyl and the like is, e.g., phenyl or naphthyl that is unsubstituted or mono-, di- or tri-substituted by lower alkyl, lower alkoxy optionally substituted with halogens, hydroxy, lower alkylamino, di-lower alkylamino, halogen and/or by trifluoromethyl.

Cycloalkoxy and cycloalkoxy in cycloalkoxy-lower alkoxy is, e.g., 3- to 8-membered, preferably 3-, 5- or 6-membered, cycloalkoxy, such as cyclopropyloxy, cyclopentyloxy, cyclohexyloxy, also cyclobutyloxy, cycloheptyloxy or cyclooctyloxy.

Cycloalkyl and cycloalkyl in cycloalkyl-alkyl refers, e.g., to optionally substituted monocyclic, bicyclic or tricyclic hydrocarbon groups of 3-12 carbon atoms, each of which may be optionally substituted by one or more substituents such as alkenyl, alkynyl, halo, hydroxy, alkoxy, alkoxy-alkoxy, alkylthio, arylthio, aryl-alkoxy, carbamoyl, sulfamoyl, sulfonyl, optionally substituted amino, cyano, carboxy, alkoxycarbonyl, aryl, aryloxy, heterocyclyl or alkyl optionally substituted by amino, halo, hydroxy, alkoxy, carboxy, carbamoyl or heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

Optionally substituted amino refers to a primary or secondary amino group which may optionally be substituted, e.g., by acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

Carbamoyl refers, e.g., to $H_2NC(O)-$, alkyl-NHC(O)—, $(alkyl)_2NC(O)-$, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

Sulfamoyl refers, e.g., to $H_2NS(O)_2-$, alkyl-NHS(O)$_2$—, $(alkyl)_2NS(O)_2-$, aryl-NHS(O)$_2$—, alkyl(aryl)-NS(O)$_2$—, $(aryl)_2NS(O)_2-$, heteroaryl-NHS(O)$_2$—, aralkyl-NHS(O)$_2$—, heteroaralkyl-NHS(O)$_2$— and the like.

Free or esterified or amidated carboxy-lower alkoxy is, e.g., carboxy-lower alkoxy, lower alkoxycarbonyl-lower alkoxy, carbamoyl-lower alkoxy or N-mono- or N,N-di-lower alkylcarbamoyl-lower alkoxy.

Optionally substituted lower alkanoylated, halogenated or sulfonylated hydroxy-lower alkoxy is, e.g., lower alkanoyloxy-lower alkyl, hydroxy-lower alkoxy, halo-(hydroxy)-lower alkoxy or lower alkanesulfonyl-(hydroxy)-lower alkoxy.

Amino-lower alkyl that is unsubstituted or substituted by lower alkyl, lower alkanoyl and/or by lower alkoxycarbonyl is, e.g., amino-lower alkyl, lower alkylamino-lower alkyl, di-lower alkylamino-lower alkyl, lower alkanoylamino-lower alkyl or lower alkoxycarbonylamino-lower alkyl.

Amino-lower alkoxy that is unsubstituted or substituted by lower alkyl, lower alkanoyl and/or by lower alkoxycarbonyl is, e.g., amino-lower alkoxy, lower alkylamino-lower alkoxy, di-lower alkylamino-lower alkoxy, lower alkanoylamino-lower alkoxy or lower alkoxycarbonylamino-lower alkoxy.

Optionally S-oxidised lower alkylthio-lower alkoxy is, e.g., lower alkylthio-lower alkoxy or lower alkanesulfonyl-lower alkoxy.

Optionally hydrogenated heteroaryl-lower alkoxy is, e.g., optionally partially hydrogenated or N-oxidised pyridyl-lower alkoxy, thiazolyl-lower alkoxy or especially morpholino-lower alkoxy.

Optionally hydrogenated heteroarylthio-lower alkoxy is, e.g., optionally partially or fully hydrogenareal heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy or pyrimidinylthio-lower alkoxy.

Free or esterified or amidated carboxy-lower alkyl is, e.g., carboxy-lower alkyl, lower alkoxycarbonyl-lower alkyl, carbamoyl-lower alkyl or N-mono- or N,N-di-lower alkylcarbamoyl-lower alkyl.

Optionally halogenated lower alkyl is, e.g., lower alkyl or polyhalo-lower alkyl.

Optionally halogenated lower alkoxy is, e.g., lower alkoxy or polyhalo-lower alkoxy.

Optionally S-oxidised lower alkylthio-lower alkyl is, e.g., lower alkylthio-lower alkyl or lower alkanesulfonyl-lower alkyl.

Optionally S-oxidised lower alkylthio-lower alkoxy is, e.g., lower alkylthio-lower alkoxy or lower alkanesulfonyl-lower alkoxy.

Optionally hydrogenated heteroaryl-lower alkyl is, e.g., optionally partially hydrogenated or N-oxidised pyridyl-lower alkyl.

Optionally hydrogenated heteroarylthio-lower alkyl is, e.g., thiazolylthio-lower alkyl or thiazolinylthio-lower alkyl, imidazolylthio-lower alkyl, optionally N-oxidised pyridylthio-lower alkyl or pyrimidinylthio-lower alkyl.

Amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N-lower alkanoylated aza-lower alkylene, by oxa-lower alkylene; or by optionally S-oxidised thia-lower alkylene is, e.g., amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl.

Optionally S-oxidised lower alkylthio-lower alkoxy is, e.g., lower alkylthio-lower alkoxy or lower alkanesulfonyl-lower alkoxy.

Amino-lower alkoxy that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene is, e.g., amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothio-morpholino-lower alkoxy.

Unsubstituted or N-mono- or N,N-di-lower alkylated or N-lower alkanoylated amino is, e.g., amino, lower alkylamino, di-lower alkylamino or lower alkanoylamino.

Free or aliphatically esterified or etherified hydroxy-lower alkyl is, e.g., hydroxy-lower alkyl, lower alkanoyloxy-lower alkyl, lower alkoxy-lower alkyl or lower alkenyloxy-lower alkyl.

Amino-lower alkyl that is unsubstituted or N-lower alkanoylated, N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated aza-lower alkylene, by oxa-lower alkylene; or by optionally S-oxidised thia-lower alkylene is, e.g., amino-lower alkyl, lower alkanoylamino-lower alkyl, N-mono- or N,N-di-lower alkylamino-lower alkyl, optionally hydroxylated or lower alkoxylated piperidino-lower alkyl, such as piperidino-lower alkyl, hydroxypiperidino-lower alkyl or lower alkoxy-piperidino-lower alkyl, piperazino-, W-lower alkylpiperazino-; or N'-lower alkanoyl-piperazino-lower alkyl, unsubstituted or lower alkylated morpholino-lower alkyl, such as morpholino-lower alkyl or dimethylmorpholino-lower alkyl; or optionally S-oxidised thiomorpholino-lower alkyl, such as thiomorpholino-lower alkyl or S,S-dioxothiomorpholino-lower alkyl.

Free or esterified or amidated dicarboxy-lower alkyl is, e.g., dicarboxy-lower alkyl, di-lower alkoxycarbonyl-lower alkyl, dicarbamoyl-lower alkyl or di-(N-mono- or N,N-di-lower alkylcarbamoyl)-lower alkyl.

Free or esterified or amidated carboxy-(hydroxy)-lower alkyl is, e.g., carboxy-(hydroxy)-lower alkyl, lower alkoxycarbonyl-(hydroxy)-lower alkyl or carbamoyl-(hydroxy)-lower alkyl.

Free or esterified or amidated carboxycycloalkyl-lower alkyl is, e.g., 5- or 6-membered carboxycycloalkyl-lower alkyl, lower alkoxycarbonylcycloalkyl-lower alkyl, carbamoylcycloalkyl-lower alkyl or N-mono- or N,N-di-lower alkylcarbamoylcyclo-alkyl-lower alkyl.

Unsubstituted or N-mono- or N,N-di-lower alkylated sulfamoyl-lower alkyl is, e.g., sulfamoyl-lower alkyl, lower alkylsulfamoyl-lower alkyl or di-lower alkyl-sulfamoyl-lower alkyl.

Unsubstituted or N-mono- or N,N-di-lower alkylated thiocarbamoyl-lower alkyl is, e.g., thiocarbamoyl-lower alkyl, lower alkylthiocarbamoyl-lower alkyl; or di-lower alkylthiocarbamoyl-lower alkyl, such as N,N-dimethylthiocarbamoyl-methyl.

Hereinbefore and hereinafter, lower radicals and compounds are to be understood as being, e.g., those having up to and including 7 carbon atoms, preferably up to and including 4 carbon atoms.

Five- or 6-membered carboxycycloalkyl-lower alkyl, lower alkoxycarbonylcycloalkyl-lower alkyl, carbamoylcycloalkyl-lower alkyl, N-mono- or N,N-di-lower alkylcarbamoylcyclo-alkyl-lower alkyl is, e.g., ω-(1-carboxycycloalkyl)-$C_1$-$C_4$alkyl, ω-(1-lower alkoxycarbonylcycloalkyl)-$C_1$-$C_4$alkyl, ω-(1-carbamoylcycloalkyl)-$C_1$-$C_4$alkyl, ω-(1-lower alkylcarbamoylcycloalkyl)-$C_1$-$C_4$alkyl or ω-(1-di-lower alkylcarbamoylcycloalkyl)-$C_1$-$C_4$alkyl, wherein cycloalkyl is, e.g., cyclopentyl or cyclohexyl; lower alkoxycarbonyl is, e.g., $C_1$-$C_4$alkoxycarbonyl, such as methoxy- or ethoxycarbonyl; lower alkylcarbamoyl is, e.g., $C_1$-$C_4$alkylcarbamoyl, such as methylcarbamoyl; di-lower alkylcarbamoyl is, e.g., di-$C_1$-$C_4$alkylcarbamoyl, such as dimethylcarbamoyl; and lower alkyl is, e.g., $C_1$-$C_4$alkyl, such as methyl, ethyl, propyl or butyl, especially (1-carboxycyclopentyl)methyl.

Five- or 6-membered cycloalkoxy-lower alkoxy is, e.g., cyclopentyloxy- or cyclohexyloxy-$C_1$-$C_4$alkoxy, such as cyclopentyloxy- or cyclohexyloxy-methoxy, 2-cyclopentyloxy- or 2-cyclohexyloxy-ethoxy, 2- or 3-cyclopentyloxy- or 2- or 3-cyclohexyloxy-propyloxy or 4-cyclopentyloxy- or 4-cyclohexyloxy-butyloxy, especially cyclopentyloxy- or cyclohexyloxy-methoxy.

Five- or 6-membered cycloalkoxy-lower alkyl is, e.g., cyclopentyloxy- or cyclohexyloxy-$C_1$-$C_4$alkyl, such as cyclopentyloxy- or cyclohexyloxy-methyl, 2-cyclopentyloxy- or 2-cyclohexyloxy-ethyl, 2- or 3-cyclopentyloxy- or 2- or 3-cyclohexyloxy-propyl, 2-cyclopentyloxy- or 2-cyclohexyloxy-2-methyl-propyl, 2-cyclopentyloxy- or 2-cyclohexyloxy-2-ethyl-butyl or 4-cyclopentyloxy- or 4-cyclohexyloxy-butyl, especially cyclopentyloxy- or cyclohexyloxy-methyl.

Amino-lower alkoxy is, e.g., amino-$C_1$-$C_4$alkoxy, such as 2-aminoethoxy or 5-aminopentyloxy, also 3-aminopropyloxy or 4-aminobutyloxy.

Amino-lower alkyl is, e.g., amino-$C_1$-$C_4$alkyl, such as 2-aminoethyl, 3-aminopropyl or 4-aminobutyl.

Carbamoyl-(hydroxy)-lower alkyl is, e.g., carbamoyl-$C_1$-$C_7$(hydroxy)alkyl, such as 1-carbamoyl-2-hydroxyethyl.

Carbamoyl-lower alkoxy is, e.g., carbamoyl-$C_1$-$C_4$alkoxy, such as carbamoylmethoxy, 2-carbamoylethoxy, 3-carbamoylpropyloxy or 4-carbamoylbutyloxy, especially carbamoylmethoxy.

Carbamoyl-lower alkyl is, e.g., carbamoyl-$C_1$-$C_7$alkyl, such as carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-(carbamoyl-2-methyl)propyl, 4-carbamoylbutyl, 1-carbamoylbutyl, 1-(1-carbamoyl-2-methyl)butyl or 3-(4-carbamoyl-2-methyl)butyl.

Carboxy-(hydroxy)-lower alkyl is, e.g., carboxy-$C_1$-$C_7$(hydroxy)alkyl, such as 1-carboxy-2-hydroxy-ethyl.

Carboxy-lower alkoxy is, e.g., carboxy-$C_1$-$C_4$alkoxy, such as carboxymethoxy, 2-carboxyethoxy, 2- or 3-carboxypropyloxy or 4-carboxybutyloxy, especially carboxy-methoxy.

Carboxy-lower alkyl is, e.g., carboxy-$C_1$-$C_4$alkyl, such as carboxymethyl, 2-carboxyethyl, 2- or 3-carboxypropyl, 2-carboxy-2-methyl-propyl, 2-carboxy-2-ethyl-butyl or 4-carboxybutyl, especially carboxymethyl.

Cyano-lower alkoxy is, e.g., cyano-$C_1$-$C_4$alkoxy, such as cyanomethoxy, 2-cyano-ethoxy, 2- or 3-cyanopropyloxy or 4-cyanobutyloxy, especially cyanomethoxy.

Cyano-lower alkyl is, e.g., cyano-$C_1$-$C_4$alkyl, such as cyanomethyl, 2-cyanoethyl, 2- or 3-cyanopropyl, 2-cyano-2-methyl-propyl, 2-cyano-2-ethyl-butyl or 4-cyanobutyl, especially cyanomethyl.

Di-(N-mono- or N,N-di-lower alkylcarbamoyl)-lower alkyl is, e.g., di-(N-mono- or N,N-di-$C_1$-$C_4$alkylcarbamoyl)-$C_1$-$C_4$alkyl, such as 1,2-di-(N-mono- or N,N-di-$C_1$-$C_4$alkylcarbamoyl)ethyl or 1,3-di-(N-mono- or N,N-di-$C_1$-$C_4$alkylcarbamoyl)propyl.

Dicarbamoyl-lower alkyl is, e.g., dicarbamoyl-$C_1$-$C_4$alkyl, such as 1,2-dicarbamoylethyl or 1,3-dicarbamoylpropyl.

Dicarboxy-lower alkyl is, e.g., dicarboxy-$C_1$-$C_4$alkyl, such as 1,2-dicarboxyethyl or 1,3-dicarboxypropyl.

Dimethylmorpholino-lower alkoxy can be N-oxidised and is, e.g., 2,6-dimethylmorpholino- or 3,5-dimethylmorpholino-$C_1$-$C_4$alkoxy, such as 2,6-dimethylmorpholino- or 3,5-dimethylmorpholino-methoxy, 2-(2,6-dimethylmorpholino- or 3,5-dimethylmorpholino)-ethoxy, 3-(2,6-dimethylmorpholino- or 3,5-dimethylmorpholino)-propyloxy, 2-(2,6-dimethylmorpholino- or 3,5-dimethylmorpholino-3-methyl)propyloxy, or 1- or 2-[4-(2,6-dimethylmorpholino- or 3,5-dimethylmorpholino)]-butyloxy.

Dimethylmorpholino-lower alkyl can be N-oxidised and is, e.g., 2,6-dimethylmorpholino- or 3,5-dimethylmorpholino-$C_1$-$C_4$alkyl, such as 2,6-dimethylmorpholino- or 3,5-dimethylmorpholino-methoxy, 2-(2,6-dimethylmorpholino- or 3,5-dimethylmorpholino)-ethoxy, 3-(2,6-dimethylmorpholino- or 3,5-dimethylmorpholino)-propyl, 2-(2,6-dimethylmorpholino- or 3,5-dimethylmorpholino-3-methyl)-propyl, or 1- or 2-[4-(2,6-dimethylmorpholino- or 3,5-dimethylmorpholino)]-butyl.

Di-lower alkoxycarbonyl-lower alkyl is, e.g., di-lower alkoxycarbonyl-$C_1$-$C_4$alkyl, such as 1,2-dimethoxycarbonyl-ethyl, 1,3-dimethoxycarbonylpropyl, 1,2-dimethoxycarbonylethyl or 1,3-diethoxycarbonylpropyl.

Di-lower alkylamino is, e.g., di-$C_1$-$C_4$alkylamino, such as dimethylamino, N-methyl-N-ethylamino, diethylamino, N-methyl-N-propylamino or N-butyl-N-methylamino.

Di-lower alkylamino-lower alkoxy is, e.g., N,N-di-$C_1$-$C_4$alkylamino-$C_1$-$C_4$alkoxy, such as 2-dimethylaminoethoxy, 3-dimethylaminopropyloxy, 4-dimethylaminobutyloxy, 2-diethylaminoethoxy, 2-(N-methyl-N-ethyl-amino)ethoxy or 2-(N-butyl-N-methyl-amino)ethoxy.

Di-lower alkylamino-lower alkyl is, e.g., N,N-di-$C_1$-$C_4$alkylamino-$C_1$-$C_4$alkyl, such as 2-dimethylaminoethyl, 3-dimethylaminopropyl, 4-dimethylaminobutyl, 2-diethylaminoethyl, 2-(N-methyl-N-ethyl-amino)ethyl or 2-(N-butyl-N-methyl-amino)ethyl.

Di-lower alkylcarbamoyl-lower alkoxy is, e.g., N,N-di-$C_1$-$C_4$alkylcarbamoyl-$C_1$-$C_4$alkoxy, such as methyl- or dimethyl-carbamoyl-$C_1$-$C_4$alkoxy, such as N-methyl-, N-butyl- or N,N-dimethyl-carbamoylmethoxy, 2-(N-methylcarbamoyl)ethoxy, 2-(N-butylcarbamoyl)ethoxy, 2-(N,N-dimethylcarbamoyl)ethoxy, 3-(N-methylcarbamoyl)propyloxy, 3-(N-butylcarbamoyl)propyloxy, 3-(N,N-dimethylcarbamoyl) propyloxy or 4-(N-methylcarbamoyl)butyloxy, 4-(N-butylcarbamoyl)butyloxy or 4-(N,N-dimethylcarbamoyl) butyloxy, especially N-methyl-, N-butyl- or N,N-dimethyl-carbamoylmethoxy.

Di-lower alkylcarbamoyl-lower alkyl is, e.g., N,N-di-$C_1$-$C_4$alkylcarbamoyl-$C_1$-$C_4$alkyl, such as 2-dimethylcarbamoylethyl, 3-dimethylcarbamoylpropyl, 2-dimethylcarbamoylpropyl, 2-(dimethylcarbamoyl-2-methyl)propyl or 2-(1-dimethylcarbamoyl-3-methyl)butyl.

Di-lower alkylsulfamoyl-lower alkyl is, e.g., N,N-di-$C_1$-$C_4$alkylsulfamoyl-$C_1$-$C_4$alkyl, N,N-dimethylsulfamoyl-$C_1$-$C_4$alkyl, such as N,N-dimethylsulfamoylmethyl, 2-(N,N-dimethylcarbamoyl)ethyl, 3-(N,N-dimethylcarbamoyl) propyl or 4-(N,N-dimethylcarbamoyl)butyl, especially N,N-dimethylcarbamoylmethyl.

Unsubstituted or N-lower alkanoylated piperidyl-lower alkyl is, e.g., 1-$C_1$-$C_7$-lower alkanoylpiperidin-4-yl-$C_1$-$C_4$alkyl, such as 1-acetylpiperidinylmethyl or 2-(1-acetylpiperidinyl)ethyl.

Optionally partially hydrogenated or N-oxidised pyridyl-lower alkoxy is, e.g., optionally partially hydrogenated pyridyl- or N-oxidopyridyl-$C_1$-$C_4$alkoxy, such as pyridyl- or N-oxidopyridyl-methoxy, 2-pyridylethoxy, 2- or 3-pyridylpropyloxy or 4-pyridylbutyloxy, especially 3- or 4-pyridylmethoxy.

Optionally partially hydrogenated or N-oxidised pyridyl-lower alkyl is, e.g., optionally partially hydrogenated pyridyl- or N-oxidopyridyl-$C_1$-$C_4$alkyl, such as pyridyl- or N-oxidopyridyl-methyl, 2-pyridylethyl, 2- or 3-pyridylpropyl or 4-pyridylbutyl, especially 3- or 4-pyridyl methyl.

Halo-(hydroxy)-lower alkoxy is, e.g., halo-$C_2$-$C_7$(hydroxy)alkoxy, especially halo-$C_2$-$C_4$(hydroxy)alkoxy, such as 3-halo-, such as 3-chloro-2-hydroxy-propyloxy.

Hydroxy-lower alkoxy is, e.g., hydroxy-$C_2$-$C_7$alkoxy, especially hydroxy-$C_2$-$C_4$alkoxy, such as 2-hydroxybutyloxy, 3-hydroxypropyloxy or 4-hydroxybutyloxy.

Hydroxy-lower alkyl is, e.g., hydroxy-$C_2$-$C_7$alkyl, especially hydroxy-$C_2$-$C_4$alkyl, such as 2-hydroxyethyl, 3-hydroxypropyl or 4-hydroxybutyl.

Hydroxypiperidino-lower alkyl is, e.g., 3- or 4-hydroxypiperidino-$C_1$-$C_4$alkoxy, such as 3- or 4-hydroxypiperidinomethoxy, 2-(3- or 4-hydroxypiperidino)ethoxy, 3-(3- or 4-hydroxypiperidino)propyloxy or 4-(3- or 4-hydroxypiperidino)butyloxy.

Imidazolyl-lower alkyl is, e.g., imidazolyl-$C_1$-$C_4$alkyl, such as imidazol-4-yl-methyl, 2-(imidazol-4-yl)ethyl, 3-(imidazol-4-yl)propyl or 4-(imidazol-4-yl)butyl.

Imidazolyl-lower alkoxy is, e.g., imidazolyl-$C_1$-$C_4$alkoxy, such as imidazol-4-yl-methoxy, 2-(imidazol-4-yl)ethoxy, 3-(imidazol-4-yl)propyloxy or 4-(imidazol-4-yl)butyloxy.

Imidazolyl-lower alkyl is, e.g., imidazolyl-$C_1$-$C_4$alkyl, such as imidazol-4-yl-methyl, 2-(imidazol-4-yl)ethyl, 3-(imidazol-4-yl)propyl or 4-(imidazol-4-yl)butyl.

Morpholinocarbonyl-lower alkyl is, e.g., morpholinocarbonyl-$C_1$-$C_4$alkyl, such as 1-morpholinocarbonylethyl, 3-morpholinocarbonylpropyl or 1-(morpholinocarbonyl-2-methyl)propyl.

Morpholino-lower alkoxy can be N-oxidised and is, e.g., morpholino-$C_1$-$C_4$alkoxy, such as 1-morpholinoethoxy, 3-morpholinopropyloxy or 1-(morpholino-2-methyl)propyloxy.

Morpholino-lower alkyl can be N-oxidised and is, e.g., morpholino-$C_1$-$C_4$alkyl, such as morpholinomethyl, 2-morpholinoethyl, 3-morpholinopropyl or 1- or 2-(4-morpholino) butyl.

Lower alkanoyl is, e.g., $C_1$-$C_7$alkanoyl, especially $C_2$-$C_6$alkanoyl, such as acetyl, propionyl, butyryl, isobutyryl or pivaloyl.

Lower alkanoylamino is, e.g., N—$C_1$-$C_7$alkanoylamino, such as acetylamino or pivaloylamino.

Lower alkanoylamino is, e.g., N—$C_1$-$C_7$alkanoylamino, such as acetylamino or pivaloylamino.

Lower alkanoylamino-lower alkyl is, e.g., N—$C_1$-$C_4$alkanoylamino-$C_1$-$C_4$alkyl, such as 2-acetoxyaminoethyl.

Lower alkanoylamino-lower alkyl is, e.g., N—$C_1$-$C_4$alkanoylamino-$C_1$-$C_4$alkyl, such as 2-acetoxyaminoethyl.

Lower alkanoyl-lower alkoxy (oxo-lower alkoxy) carries the lower alkanoyl group in a position higher than the α-position and is, e.g., $C_1$-$C_7$alkanoyl-$C_1$-$C_4$alkoxy, such as 4-acetyl butoxy.

Lower alkanoyloxy-lower alkyl carries the lower alkanoyloxy group in a position higher than the α-position and is, e.g., $C_1$-$C_7$alkanoyloxy-$C_1$-$C_4$alkyl, such as 4-acetoxy-butyl.

Lower alkanesulfonyl-(hydroxy)-lower alkoxy is, e.g., $C_1$-$C_7$alkanesulfonyl-$C_1$-$C_4$(hydroxy)alkoxy, such as 3-methanesulfonyl-2-hydroxy-propyloxy.

Lower alkanesulfonyl-lower alkoxy is, e.g., $C_1$-$C_7$alkanesulfonyl-$C_1$-$C_4$alkoxy, such as methanesulfonylmethoxy or 3-methanesulfonyl-2-hydroxy-propyloxy.

Lower alkanesulfonylamino-lower alkoxy is, e.g., $C_1$-$C_7$alkanesulfonylamino-$C_1$-$C_4$alkoxy, such as ethanesulfonylaminomethoxy, 2-ethanesulfonylaminoethoxy, 3-ethanesulfonylaminopropyloxy or 3-(1,1-dimethylethanesulfonylamino)propyloxy.

Lower alkanesulfonylamino-lower alkyl is, e.g., $C_1$-$C_7$alkanesulfonylamino-$C_1$-$C_4$alkyl, such as ethanesulfonylaminomethyl, 2-ethanesulfonylaminoethyl, 3-ethanesulfonylaminopropyl or 3-(1,1-dimethylethanesulfonylamino)propyl.

Lower alkanesulfonyl-lower alkyl is, e.g., $C_1$-$C_7$alkanesulfonyl-$C_1$-$C_4$alkyl, such as ethanesulfonylmethyl, 2-ethanesulfonylethyl, 3-ethanesulfonylpropyl or 3-(1,1-dimethylethanesulfonyl)propyl.

Lower alkenyl is, e.g., $C_1$-$C_7$alkenyl, such as vinyl or allyl.

Lower alkenyloxy is, e.g., $C_1$-$C_7$alkenyloxy, such as allyloxy.

Lower alkenyloxy-lower alkoxy is, e.g., $C_1$-$C_7$alkenyloxy-$C_1$-$C_4$alkoxy, such as allyloxymethoxy.

Lower alkenyloxy-lower alkyl is, e.g., $C_1$-$C_7$alkenyloxy-$C_1$-$C_4$alkyl, such as allyloxymethyl.

Lower alkoxy is, e.g., $C_1$-$C_7$alkoxy, preferably $C_1$-$C_5$alkoxy, such as methoxy, ethoxy, propyloxy, isopropyloxy, butyloxy, isobutyloxy, secondary butyloxy, tertiary butyloxy, pentyloxy or a hexyloxy or heptyloxy group.

Lower alkoxycarbonyl is, e.g., $C_1$-$C_7$alkoxycarbonyl, preferably $C_1$-$C_5$alkoxycarbonyl, such as methoxycarbonyl, ethoxycarbonyl, propyloxycarbonyl, isopropyloxycarbonyl, butyloxycarbonyl, isobutyloxycarbonyl, secondary butyloxycarbonyl, tertiary butyloxy, pentyloxycarbonyl or a hexyloxycarbonyl or heptyloxycarbonyl group.

Lower alkoxycarbonyl-(hydroxy)-lower alkyl is, e.g., $C_1$-$C_4$alkoxycarbonyl-$C_1$-$C_7$(hydroxy)alkyl, such as 1-methoxycarbonyl- or 1-ethoxycarbonyl-2-hydroxy-ethyl.

Lower alkoxycarbonylamino-lower alkoxy is, e.g., $C_1$-$C_7$alkoxycarbonylamino-$C_2$-$C_7$alkoxy, preferably $C_2$-$C_5$alkoxycarbonylamino-$C_2$-$C_7$alkoxy, such as methoxycarbonylamino-$C_2$-$C_7$alkoxy, ethoxycarbonylamino-$C_2$-$C_7$alkoxy, propyl oxycarbonylamino-$C_2$-$C_7$alkoxy, isobutyl oxycarbonylamino-$C_2$-$C_7$alkoxy, butyloxycarbonylamino-$C_2$-$C_7$alkoxy, isobutyl oxycarbonylamino-$C_2$-$C_7$alkoxy, secondary butyloxycarbonylamino-$C_2$-$C_7$alkoxy or tertiary butyloxyamino-$C_2$-$C_7$alkoxy, wherein $C_2$-$C_7$alkoxy is, e.g., methoxy, ethoxy, propyloxy, butyloxy, pentyloxy or hexyloxy.

Lower alkoxycarbonylamino-lower alkyl is, e.g., $C_1$-$C_7$alkoxycarbonylamino-$C_2$-$C_7$alkyl, preferably $C_2$-$C_5$alkoxycarbonylamino-$C_2$-$C_7$alkyl, such as methoxycarbonyl-$C_2$-$C_7$alkyl, ethoxycarbonylamino-$C_2$-$C_7$alkyl, propyl oxycarbonylamino-$C_2$-$C_7$alkyl isopropyloxycarbonylamino-$C_2$-$C_7$alkyl, butyloxycarbonylamino-$C_2$-$C_7$alkyl, isobutyloxycarbonylamino-$C_2$-$C_7$alkyl, secondary butyloxycarbonylamino-$C_2$-$C_7$alkyl or tertiary butyloxyamino-$C_2$-$C_7$alkyl, wherein $C_2$-$C_7$alkyl is, e.g., methyl, ethyl, propyl, butyl, pentyl or hexyl.

Lower alkoxycarbonyl-lower alkoxy is, e.g., $C_1$-$C_4$alkoxycarbonyl-$C_1$-$C_4$alkoxy, such as methoxycarbonyl- or ethoxycarbonyl-methoxy, 2-methoxycarbonyl- or 2-ethoxycarbonyl-ethoxy, 2- or 3-methoxycarbonyl- or 2- or 3-ethoxycarbonyl-propyloxy or 4-methoxycarbonyl- or 4-ethoxycarbonyl-butyloxy, especially methoxycarbonyl- or ethoxycarbonyl-methoxy or 3-methoxycarbonyl- or 3-ethoxycarbonyl-propyloxy.

Lower alkoxycarbonyl-lower alkyl is, e.g., $C_1$-$C_4$alkoxycarbonyl-$C_1$-$C_4$alkyl, such as methoxycarbonyl- or ethoxycarbonyl-methoxy, 2-methoxycarbonyl- or 2-ethoxycarbonyl-ethoxy, 3-methoxycarbonyl- or 3-ethoxycarbonyl-propyloxy or 4-ethoxycarbonylbutyloxy.

Lower alkoxy-lower alkenyl is, e.g., $C_1$-$C_4$alkoxy-$C_2$-$C_4$alkenyl, such as 4-methoxybut-2-enyl.

Lower alkoxy-lower alkoxy is, e.g., $C_1$-$C_4$alkoxy-$C_2$-$C_4$alkoxy, such as 2-methoxy-, 2-ethoxy- or 2-propyloxy-ethoxy, 3-methoxy- or 3-ethoxy-propyloxy or 4-methoxybutyloxy, especially 3-methoxypropyloxy or 4-methoxybutyloxy.

Lower alkoxy-lower alkoxy-lower alkyl is, e.g., $C_1$-$C_4$alkoxy-$C_1$-$C_4$alkoxy-$C_1$-$C_4$alkyl, such as 2-methoxy-, 2-ethoxy- or 2-propyloxy-ethoxymethyl, 2-(2-methoxy-, 2-ethoxy- or 2-propyloxy-ethoxy)ethyl, 3-(3-methoxy- or 3-ethoxy-propyloxy)propyl or 4-(2-methoxybutyloxy)butyl, especially 2-(3-methoxypropyloxy)ethyl or 2-(4-methoxybutyloxy)ethyl.

Lower alkoxy-lower alkyl is, e.g., $C_1$-$C_4$alkoxy-$C_1$-$C_4$alkyl, such as ethoxymethyl, propyloxymethyl, butyloxymethyl, 2-methoxy-, 2-ethoxy- or 2-propyloxy-ethyl, 3-methoxy- or 3-ethoxy-propyl or 4-methoxybutyl, especially 3-methoxypropyl or 4-methoxybutyl.

Lower alkoxypiperidino-lower alkyl is, e.g., piperidino-, hydroxypiperidino- or lower alkoxypiperidino-$C_1$-$C_4$alkyl, such as piperidinomethyl, 4-hydroxypiperidinomethyl or 4-$C_1$-$C_4$alkoxy-, such as 4-methoxy-piperidinomethyl.

Lower alkoxypiperidino-lower alkyl is, e.g., $C_1$-$C_4$alkoxypiperidino-$C_1$-$C_4$alkyl, such as 4-$C_1$-$C_4$alkoxypiperidinomethyl, especially 4-methoxypiperidinomethyl.

Lower alkyl may be straight-chained or branched and/or bridged and is, e.g., corresponding $C_1$-$C_7$alkyl, such as methyl, ethyl, propyl, isopropyl, butyl, isobutyl, secondary butyl or tertiary butyl, or a pentyl, hexyl or heptyl group. Lower alkyl $R_2$ or $R_3$ is especially $C_2$-$C_7$alkyl, lower alkyl $R_5$ or $R_7$ is especially branched $C_3$-$C_7$alkyl and lower alkyl $R_8$ or $R_3$ is, e.g., straight-chained, branched or bridged $C_3$-$C_7$alkyl.

Lower alkylamino is, e.g., $C_1$-$C_4$alkylamino, such as methylamino, ethylamino, propylamino, butylamino, isobutylamino, secondary butylamino or tertiary butylamino.

Lower alkylamino-lower alkoxy is, e.g., $C_1$-$C_4$alkylamino-$C_1$-$C_4$alkoxy, such as propylaminomethoxy, 2-methylamino-, 2-ethylamino-, 2-propylamino- or 2-butylamino-ethoxy, 3-ethylamino- or 3-propylamino-propyloxy or 4-methylaminobutoxy.

Lower alkylamino-lower alkyl is, e.g., $C_1$-$C_4$alkylamino-$C_1$-$C_4$alkyl, such as propylaminomethyl, 2-methylamino-, 2-ethylamino-, 2-propylamino- or 2-butylamino-ethyl, 3-ethylamino- or 3-propylamino-propyl or 4-methylaminobutyl.

Lower alkylcarbamoyl-lower alkoxy is, e.g., N—$C_1$-$C_7$alkylcarbamoyl-$C_1$-$C_4$alkoxy, such as methyl- or dimethyl-carbamoyl-$C_1$-$C_4$alkoxy, e.g. methylcarbamoylmethoxy, 2-methylcarbamoylethoxy or 3-methylcarbamoylpropyloxy.

Lower alkylenedioxy is, e.g., methylenedioxy or ethylenedioxy, but can also be 1,3- or 1,2-propylenedioxy.

Lower alkylsulfamoyl-lower alkyl is, e.g., N—$C_1$-$C_7$alkylsulfamoyl-$C_1$-$C_4$alkyl, such as N-methyl-, N-ethyl-, N-propyl- or N-butyl-sulfamoyl-$C_1$-$C_4$alkyl, such as N-methyl-, N-ethyl-, N-propyl- or N-butyl-sulfamoylmethyl, 2-(N-methylsulfamoyl)ethyl, 2-(N-butylsulfamoyl)ethyl, 3-(N-methylsulfamoyl)propyl, 3-(N-butylsulfamoyl)propyl or 4-(N-methylsulfamoyl)butyl, 4-(N-butylsulfamoyl)butyl or 4-(N,N-dimethylsulfamoyl)butyl, especially N-methyl-, N-butyl- or N,N-dimethyl-sulfamoylmethyl.

Lower alkylthio-(hydroxy)-lower alkoxy is, e.g., N—$C_1$-$C_4$alkylthio-$C_1$-$C_4$(hydroxy)alkoxy, such as 2-hydroxy-3-methylthiopropyloxy.

Oxazolyl-lower alkyl is, e.g., oxazolyl-$C_1$-$C_4$alkyl, such as 2-(1,2,4-oxadiazol-5-yl)ethyl, 3-(1,2,4-oxadiazol-5-yl)propyl or 4-(1,2,4-oxadiazol-5-yl)butyl.

Lower alkylthio-lower alkoxy is, e.g., N—$C_1$-$C_4$alkylthio-$C_1$-$C_4$alkoxy, such as methylthio-$C_1$-$C_4$alkoxy, e.g., methylthiomethoxy, 2-methylthioethoxy or 3-methylthiopropyloxy.

Lower alkylthio-lower alkyl is, e.g., N—$C_1$-$C_4$alkylthio-$C_1$-$C_4$alkyl, such as methylthio-$C_1$-$C_4$alkyl, e.g., methylthiomethyl, 2-methylthioethyl or 3-methylthiopropyl.

N'-Lower alkanoylpiperazino-lower alkoxy is, e.g., N'-lower alkanoylpiperazino-$C_1$-$C_4$alkoxy, such as 4-acetylpiperazinomethoxy.

N'-Lower alkanoylpiperazino-lower alkyl is, e.g., N'—$C_2$-$C_7$-lower alkanoylpiperazino-$C_1$-$C_4$alkyl, such as 4-acetylpiperazinomethyl.

N'-Lower alkylpiperazino-lower alkyl is, e.g., N'—$C_1$-$C_4$alkylpiperazino-$C_1$-$C_4$alkyl, such as 4-methylpiperazinomethyl.

Oxo-lower alkoxy is, e.g., oxo-$C_1$-$C_4$alkoxy, such as 3,3-dimethyl-2-oxo-butyloxy.

Piperazino-lower alkyl is, e.g., piperazino-$C_1$-$C_4$alkyl, such as piperazinomethyl, 2-piperazinoethyl or 3-piperazinopropyl.

Piperidino-lower alkoxy is, e.g., piperidino-$C_1$-$C_4$alkoxy, such as piperidinomethoxy, 2-piperidinoethoxy or 3-piperidinopropyloxy.

Piperidino-lower alkyl is, e.g., piperidino-$C_1$-$C_4$alkyl, such as piperidinomethyl, 2-piperidinoethyl or 3-piperidinopropyl.

Polyhalo-lower alkanesulfonylamino-lower alkoxy is, e.g., trifluoro-$C_1$-$C_7$alkanesulfonyl-$C_1$-$C_4$alkoxy, such as trifluoromethanesulfonylaminobutyloxy.

Polyhalo-lower alkanesulfonylamino-lower alkyl is, e.g., trifluoro-$C_1$-$C_7$alkanesulfonyl-$C_1$-$C_4$alkyl, such as trifluoromethanesulfonylaminobutyl.

Pyrimidinyl-lower alkoxy is, e.g., pyrimidinyl-$C_1$-$C_4$alkoxy, such as pyrimidinylmethoxy, 2-pyrimidinylethoxy or 3-pyrimidinylpropyloxy.

Pyrimidinyl-lower alkyl is, e.g., pyrimidinyl-$C_1$-$C_4$alkyl, such as pyrimidinylmethyl, 2-pyrimidinylethyl or 3-pyrimidinylpropyl.

Pyrrolidino-lower alkoxy is, e.g., pyrrolidino-$C_2$-$C_4$alkoxy, such as 2-pyrrolidinoethoxy or 3-pyrrolidinopropyloxy.

Pyrrolidino-lower alkyl is, e.g., pyrrolidino-$C_1$-$C_4$alkyl, such as pyrrolidinomethyl, 2-pyrrolidinoethyl or 3-pyrrolidinopropyl.

S,S-Dioxothiomorpholino-lower alkyl is, e.g., S,S-dioxothiomorpholino-$C_1$-$C_4$alkyl, such as S,S-dioxothiomorpholinomethyl or 2-(S,S-dioxo)thiomorpholinoethyl.

S-Oxothiomorpholino-lower alkyl is, e.g., S-oxothiomorpholino-$C_1$-$C_4$alkyl, such as S-oxothiomorpholinomethyl or 2-(S-oxo)thiomorpholinoethyl.

Sulfamoyl-lower alkyl is, e.g., sulfamoyl-$C_1$-$C_4$alkyl, such as sulfamoyl-$C_1$-$C_4$alkyl, such as sulfamoylmethyl, 2-sulfamoylethyl, 3-sulfamoylpropyl or 4-sulfamoylbutyl.

Tetrazolyl-lower alkyl is, e.g., tetrazolyl-$C_1$-$C_4$alkyl, such as tetrazol-5-ylmethyl, 2-(tetrazol-5-yl)ethyl, 3-(tetrazol-5-yl)propyl or 4-(tetrazol-4-yl)butyl.

Thiazolinyl-lower alkoxy is, e.g., thiazolinyl-$C_1$-$C_4$alkoxy, such as thiazolinylmethoxy, 2-thiazolinylmethoxy or 3-thiazolinylpropyloxy.

Thiazolinyl-lower alkyl is, e.g., thiazolinyl-$C_1$-$C_4$alkyl, such as thiazolinylmethyl, 2-thiazolinylethyl or 3-thiazolinylpropyl.

Thiazolyl-lower alkoxy is, e.g., thiazolyl-$C_1$-$C_4$alkoxy, such as thiazolylmethoxy, 2-thiazolylethoxy or 3-thiazolylpropyloxy.

Thiazolyl-lower alkyl is, e.g., thiazolyl-$C_1$-$C_4$alkyl, such as thiazolylmethyl, 2-thiazolylethyl or 3-thiazolylpropyl.

Thiomorpholino-lower alkyl or S,S-dioxothiomorpholino-lower alkyl is, e.g., thiomorpholino-$C_1$-$C_4$alkyl, such as -methyl or -ethyl, or S,S-dioxothiomorpholino-$C_1$-$C_4$alkyl, such as -methyl or -ethyl.

Depending on whether asymmetric carbon atoms are present, the compounds of the invention can be present as mixtures of isomers, especially as racemates, or in the form of pure isomers, especially optical antipodes.

Salts of compounds having salt-forming groups are especially acid addition salts, salts with bases or, where several salt-forming groups are present, can also be mixed salts or internal salts.

Salts are especially the pharmaceutically acceptable or non-toxic salts of compounds of formula (I).

Such salts are formed, e.g., by compounds of formula (I) having an acid group, e.g., a carboxy group or a sulfo group, and are, e.g., salts thereof with suitable bases, such as non-toxic metal salts derived from metals of groups Ia, Ib, IIa and IIb of the Periodic Table of the Elements, e.g., alkali metal salts, especially lithium, sodium or potassium salts; or alkaline earth metal salts, e.g., magnesium or calcium salts; also zinc salts or ammonium salts, as well as salts formed with organic amines, such as unsubstituted or hydroxy-substituted mono-, di- or tri-alkylamines, especially mono-, di- or tri-lower alkylamines; or with quaternary ammonium bases, e.g., with methyl-, ethyl-, diethyl- or triethyl-amine; mono-, his- or tris-(2-hydroxy-lower alkyl)-amines, such as ethanol-, diethanol- or triethanol-amine; tris-(hydroxymethyl)-methylamine or 2-hydroxy-tert-butylamines; N,N-di-lower alkyl-N-(hydroxy-lower alkyl)-amines, such as N,N-dimethyl-N-(2-hydroxyethyl)-amine or N-methyl-D-glucamine; or quaternary ammonium hydroxides, such as tetrabutylammonium hydroxide. The compounds of formula (I) having a basic group, e.g., an amino group, can form acid addition salts, e.g., with suitable inorganic acids, e.g., hydrohalic acids, such as hydrochloric acid or hydrobromic acid; or sulfuric acid with replacement of one or both protons; phosphoric acid with replacement of one or more protons, e.g., orthophosphoric acid or metaphosphoric acid; or pyrophosphoric acid with replacement of one or more protons; or with organic carboxylic, sulfonic, sulfo or phosphonic acids; or N-substituted sulfamic acids, e.g., acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, such as the α-amino acids mentioned hereinbefore; and with methanesulfonic acid, ethanesulfonic acid, 2-hydroxyethanesulfonic acid, ethane-1,2-disulfonic acid, benzenesulfonic acid, 4-toluenesulfonic acid, naphthalene-2-sulfonic acid, 2- or 3-phosphoglycerate, glucose-6-phosphate or N-cyclohexylsulfamic acid (forming cyclamates); or with other acidic organic compounds, such as ascorbic acid. Compounds of formula (I) having acid and basic groups can also form internal salts.

For isolation and purification purposes it is also possible to use pharmaceutically unacceptable salts.

The compounds of the present invention have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the lungs, the kidneys and other organs to form the octapeptide angiotensinogen II. The octapeptide increases blood pressure both directly by arterial vasoconstriction and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

Thus, the compounds of the present invention may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

The groups of compounds mentioned below are not to be regarded as exclusive; rather, e.g., in order to replace general definitions with more specific definitions, parts of those groups of compounds can be interchanged or exchanged for the definitions given above, or omitted, as appropriate.

Preferred are the compounds of formula (I), designated as the A group, wherein
  $R^9$ is lower alkyl, optionally substituted cycloalkyl (alkyl, OH, alkoxy, alkoxy-alkyl, halogens), optionally substituted cycloalkyl-alkyl (OH, alkoxy, alkoxy-alkyl, halogens on cycloalkyl), cycloalkyl carboxamides, N-mono or N,N-dialkyl substituted cycloalkyl carboxamides, optionally substituted aryl-alkyl, free or aliphatically esterified or etherified hydroxy-lower alkyl; amino-lower alkyl that is unsubstituted or N-lower alkanoylated or N-mono- or N,N-di-lower alkylated or N,N-di-substituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene, free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted;

or a pharmaceutically acceptable salt thereof.
  Preferred are the compounds in the A group wherein
  $R^1$ and $R^4$ are hydrogen;
  $R^2$ is lower alkoxy-lower alkoxy;
  $R^3$ is halogen or mono, di or tri-halo-substituted alkyl;

or a pharmaceutically acceptable salt thereof.
  Further preferred are the compounds in the A group wherein the halogen/halo is fluorine or chlorine;

or a pharmaceutically acceptable salt thereof.
  More preferred are the compounds in the A group wherein $R^3$ is fluorine or trifluoromethyl;

or a pharmaceutically acceptable salt thereof.
  Most preferred are the compounds in the A group wherein $R^2$ is in the meta position and $R^3$ is in the para position;

or a pharmaceutically acceptable salt thereof.
  Most preferred are also the compounds in the A group wherein $R^3$ is in the ortho position;

or a pharmaceutically acceptable salt thereof.
  Most preferred are also the compounds in the A group wherein $R^3$ is in the meta position;

or a pharmaceutically acceptable salt thereof.
  Preferred are also the compounds in the A group, designated as the B group, wherein $R^2$ is in the meta position and is lower alkoxy-lower alkoxy optionally substituted by halogen(s);

or a pharmaceutically acceptable salt thereof.
  Further preferred are the compounds in the B group wherein the halogen(s) is fluorine or chlorine;

or a pharmaceutically acceptable salt thereof.
  More preferred are the compounds in the B group wherein the halogen(s) is fluorine;

or a pharmaceutically acceptable salt thereof.
  Preferred are also the compounds in the B group, designated as the C group, wherein $R^3$ is lower alkoxy substituted by halogen(s);

or a pharmaceutically acceptable salt thereof.
  Preferred are the compounds in the C group wherein the halogen(s) is fluorine or chlorine;

or a pharmaceutically acceptable salt thereof.
  Further preferred are the compounds in the C group wherein the halogen(s) is fluorine;

or a pharmaceutically acceptable salt thereof.
  Preferred are also the compounds in the B group, designated as the D group, wherein $R^3$ is in the para position;

or a pharmaceutically acceptable salt thereof.
  Further preferred are the compounds in the D group wherein $R^3$ is methoxy;

or a pharmaceutically acceptable salt thereof.
  Further preferred are also the compounds in the D group wherein $R^3$ is trifluoro-methoxy;

or a pharmaceutically acceptable salt thereof.
  Preferred are also the compounds of formula (I) wherein
  $R^3$ is located at the para position and is halogen;

or a pharmaceutically acceptable salt thereof.
  Preferred are also the δ-amino-γ-hydroxy-ω-aryl-alkanoic acid amide compounds of formula (I), designated as the E group, having formula (Ia)

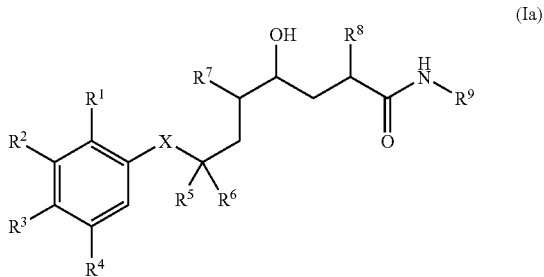

(Ia)

wherein
- $R^1$ is hydrogen, halogen, optionally halogenated alkyl, cycloalkyl, hydroxy, optionally halogenated alkoxy, cycloalkoxy, lower alkoxy-lower alkoxy or free or esterified or amidated carboxy-lower alkoxy or lower alkyl;
- $R^2$ is hydrogen, halogen, optionally halogenated lower alkyl, hydroxy, cycloalkyl, cycloalkoxy, optionally halogenated lower alkoxy-lower alkyl, optionally substituted lower alkoxy-lower alkoxy, cycloalkoxy-lower alkyl; optionally lower alkanoylated, halogenated or sulfonylated hydroxy-lower alkoxy; amino-lower alkyl that is unsubstituted or substituted by lower alkyl, by lower alkanoyl and/or by lower alkoxy-carbonyl; optionally hydrogenated heteroaryl-lower alkyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkenyl, lower alkenyloxy-lower alkoxy, lower alkoxy-lower alkenyl-oxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, aryl-lower alkyl, aryl-lower alkoxy, optionally hydrogenated heteroaryl-lower alkoxy, optionally hydrogenated heteroaryl-lower alkyl, cyano-lower alkoxy, cyano-lower alkyl, free or esterified or amidated carboxy-lower alkoxy or free or esterified or amidated carboxy-lower alkyl;
- $R^3$ and $R^4$ are independently hydrogen, halogen, optionally halogenated lower alkyl, hydroxy, optionally halogenated lower alkoxy or cycloalkoxy, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated hetero-arylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxalower alkylene or by optionally S-oxidised thia-lower alkylene; cyano-lower alkoxy or free or esterified or amidated carboxy-lower alkoxy; or
- $R^4$ together with $R_3$ is lower alkeneoxy, alkylenedioxy or a fused-on aryl, optionally hydrogenated heteroaryl or cycloalkyl ring;
- X is methylene, hydroxymethylene, oxygen, optionally lower alkyl substituted nitrogen or optionally oxidized sulfur;
- $R^5$ is lower alkyl or cycloalkyl;
- $R^6$ is hydrogen, lower alkyl, hydroxy, alkoxy or halogen;
- $R^7$ is unsubstituted or N-mono- or N,N-di-lower alkylated or N-lower alkanoylated amino;
- $R^8$ is lower alkyl, lower alkenyl, cycloalkyl or aryl-lower alkyl;
- $R^9$ is optionally substituted lower alkyl, optionally substituted cycloalkyl, optionally substituted cycloalkyl-alkyl, cycloalkyl carboxamides, N-mono or N,N-dialkyl substituted cycloalkyl carboxamides, optionally substituted aryl-alkyl, optionally substituted aryloxy-aryl, optionally substituted heteroaryloxy-alkyl, free or aliphatically esterified or etherified hydroxy-lower alkyl; amino-lower alkyl that is unsubstituted or N-lower alkanoylated or N-mono- or N,N-di-lower alkylated or N,N-di-substituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene, free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted;

or a pharmaceutically acceptable salt thereof.

Preferred are the compounds in the E group wherein
- $R^9$ is cycloalkyl substituted with alkyl, hydroxy, alkoxy, alkoxy-alkoxy or halogens; cycloalkyl-alkyl optionally substituted with alkyl, hydroxy, alkoxy, alkoxy-alkoxy or halogens on cycloalkyl or halogens on alkyl or halogens on alkoxy; cycloalkyl carboxamides; N-mono or N,N-dialkyl substituted cycloalkyl carboxamides; or optionally substituted aryl-alkyl;

or a pharmaceutically acceptable salt thereof.

Preferred are also the compounds in the E group, designated as the F group, wherein
- $R^9$ is hydrogen; halogenated alkyl; optionally substituted aryl-alkyl, optionally substituted aryloxy-alkyl, cycloalkyl substituted by 1 to 3 substituents selected from the group consisting of alkenyl, alkynyl, halo, hydroxy, alkoxy, alkoxy-alkoxy, alkylthio, arylthio, aryl-alkoxy, carbamoyl, sulfamoyl, sulfonyl, optionally substituted amino, cyano, carboxy, alkoxycarbonyl, aryl, aryloxy, heterocyclyl or alkyl optionally substituted by amino, halo, hydroxy, alkoxy, carboxy, alkoxycarbonyl, carbamoyl or heterocyclyl; or optionally substituted cycloalkyl-alkyl;

or a pharmaceutically acceptable salt thereof.

Preferred are the compounds in the F group wherein
$R^1$ is hydrogen;
$R^2$ is $C_1$-$C_4$ alkoxy—$C_1$-$C_4$ alkoxy or $C_1$-$C_4$ alkoxy—$C_1$-$C_4$ alkyl;
$R^3$ is $C_1$-$C_4$ alkyl or $C_1$-$C_4$ alkoxy;
$R^4$ is hydrogen;
X is methylene;
$R^5$ is lower alkyl;
$R^6$ is hydrogen;
$R^7$ is unsubstituted amino;
$R^8$ is branched $C_3$-$C_4$ alkyl;
$R^9$ is optionally substituted cycloalkyl-alkyl;

or a pharmaceutically acceptable salt thereof.

Further preferred are the compounds in the F group wherein
$R^2$ is 3-methoxypropyloxy;
$R^3$ is methoxy;
$R^5$ is isopropyl;
$R^8$ is isopropyl;

or a pharmaceutically acceptable salt thereof.

Preferred are also the compounds in the F group, designated as the G group, wherein
$R^1$ is hydrogen;
$R^2$ is $C_1$-$C_4$ alkoxy—$C_1$-$C_4$ alkoxy or $C_1$-$C_4$ alkoxy—$C_1$-$C_4$ alkyl;
$R^3$ is $C_1$-$C_4$ alkyl or $C_1$-$C_4$ alkoxy;
$R^4$ is hydrogen;
X is methylene;
$R^5$ is lower alkyl;
$R^6$ is hydrogen;
$R^7$ is unsubstituted amino;
$R^8$ is branched $C_3$-$C_4$ alkyl;
$R^9$ is optionally substituted aryl-alkyl; or a pharmaceutically acceptable salt thereof.

Preferred are the compounds in the G group wherein
$R^2$ is 3-methoxypropyloxy;
$R^3$ is methoxy;
$R^5$ is isopropyl;
$R^8$ is isopropyl;

or a pharmaceutically acceptable salt thereof.

Preferred are also the compounds in the G group wherein aryl-alkyl is alkyl substituted with phenyl;

or a pharmaceutically acceptable salt thereof.

Further preferred are the compounds in the G group wherein aryl-alkyl is methyl substituted with phenyl.

More preferred are the compounds in the G group wherein
$R^2$ is 3-methoxypropyloxy;
$R^3$ is methoxy;
$R^5$ is isopropyl;
$R^8$ is isopropyl;

or a pharmaceutically acceptable salt thereof.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

The compounds of the present invention may generally be prepared by those methods disclosed in U.S. Pat. No. 5,559,111, incorporated herein by reference in its entirety as if set forth in full herein.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the present invention are those suitable for enteral, such as oral or rectal, transdermal and parenteral administration to mammals, including man, to inhibit renin activity, and for the treatment of conditions associated with renin activity. Such conditions include hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) anti-obesity agents such as orlistat; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics, anti-hypertensive agents or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Thus, the present invention also relates to a compound of formula (I) for use as a medicament, to the use of a compound of formula (I) for the preparation of a pharmaceutical composition for the prevention and/or treatment of conditions mediated by renin activity, and to a pharmaceutical composition for use in conditions mediated by renin activity comprising a compound of formula (I), or a pharmaceutically acceptable salt thereof, in association with a pharmaceutically acceptable diluent or carrier therefor.

The present invention further provides a method for the prevention and/or treatment of conditions mediated by renin activity, which comprises administering a therapeutically effective amount of a compound of the present invention.

A unit dosage for a mammal of about 50-70 kg may contain between about 1 mg and 1000 mg, advantageously between about 5-600 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of renin activity.

Preferably, the condition associated with renin activity is selected from hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of onset and/or progression, and palliative treatment.

The above-cited properties are demonstrable in vitro and in vivo tests using advantageously mammals, e.g., mice, rats, rabbits, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-10}$ molar concentrations. A therapeutically effective amount in vivo may range depending on the route of administration, between about 0.001 and 500 mg/kg, preferably between about 0.1 and 100 mg/kg.

As described above, the compounds of the present invention have enzyme-inhibiting properties. In particular, they inhibit the action of the natural enzyme renin. Renin passes from the kidneys into the blood where it effects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is the direct cause of the hypotensive effect of renin inhibitors.

The action of renin inhibitors may be demonstrated inter alia experimentally by means of in vitro tests, the reduction in the formation of angiotensin I being measured in various systems (human plasma, purified human renin together with synthetic or natural renin substrate).

Inter alia the following in vitro tests may be used:

An extract of human renin from the kidney (0.5 mGU [milli-Goldblatt units]/mL) is incubated for one h at 37° C. and pH 7.2 in 1M aqueous 2-N-(tris-hydroxymethylmethyl)-amino-ethanesulfonic acid buffer solution with 23 μg/mL of synthetic renin substrate, the tetradecapeptide H-Asp-Arg-Val-Tyr-Ile-His-ProPhe-His-Leu-Leu-Val-Tyr-Ser-OH. The amount of angiotensin I formed is determined by radioimmunoassay. Each of the inhibitors according to the invention is added to the incubation mixture at different concentrations. The $IC_{50}$ is defined as the concentration of a particular inhibitor that reduces the formation of angiotensin I by 50%.

Recombinant human renin (expressed in Chinese Hamster Ovary cells and purified using standard methods) at 4 nM concentration is incubated with test compound at various concentrations for 1 h at RT in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 2 μM and increase in fluorescence is recorded at an excitation wave-length of 340 nm and at an emission wave-length of 485 nm in a microplate spectro-fluorimeter. $IC_{50}$ values are calculated from percentage of inhibition of renin activity as a function of test compound concentration (Fluorescence Resonance Energy Transfer, FRET, assay).

Recombinant human renin (expressed in Chinese Hamster Ovary cells and purified using standard methods) at 1 nM concentration is incubated with test compound at various concentrations for 1.5 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 5 μM. The enzyme reaction is stopped by adding 6 μL of 1.0% TFA. The product of the reaction is separated by HPLC and quantified by spectrophotometric measurement at 505 nM wave-length. $IC_{50}$ values are calculated from percentage of inhibition of renin activity as a function of test compound concentration.

Recombinant human renin (expressed in Chinese Hamster Ovary cells and purified using standard methods) at 3.3 nM concentration, 125I-NVP-AJ1891-NX-1 (0.27 μCi/mL) and streptavidin-SPA (0.67 mg/mL) beads are incubated with test compound at various concentrations for 2.0 h at RT in 0.1 M Tris/HCl pH 7.4 containing 0.5M NaCl and 0.5% (w/v) Brij35. At the end of the incubation time, the plates are centrifuged (55 g, 60 seconds) and counted in a Wallac Micro-Beta reader. $IC_{50}$ values are calculated from percentage of displacement of radioligand binding to renin as a function of test compound concentration.

In animals deficient in salt, renin inhibitors bring about a reduction in blood pressure. Human renin may differ from the renin of other species. In order to test inhibitors of human renin, primates, e.g., marmosets (*Callithrix jacchus*) may be used, because human renin and primate renin are substantially homologous in the enzymatically active region. Inter alia the following in vivo tests may be used:

The test compounds are tested on normotensive marmosets of both sexes having a body weight of approximately 350 g that are conscious, allowed to move freely and in their normal cages. The blood pressure and heart rate are measured via a catheter in the descending aorta and recorded radiometrically. The endogenous release of renin is stimulated by the combination of a 1-week low-salt diet and a single intramuscular injection of furosemide (5-(aminosulfonyl)-4-chloro-2-[(2-furanylmethyl)amino]benzoic acid) (5 mg/kg). 16 h after the injection of furosemide the test compounds are administered either directly into the femoral artery using an injection cannula or, in the form of a suspension or solution, via an oesophageal tube into the stomach, and their action on the blood pressure and heart rate are evaluated. In the in vivo test described, the compounds of the present invention have hypotensive action at doses of from approximately 0.003 to approximately 1 mg/kg i.v. and at doses of from approximately 0.3 to approximately 100 mg/kg p.o.

Alternatively, renin inhibitors may be tested on male normotensive marmosets weighing 250 to 500 g that are conscious, allowed to move freely and in their normal cages. The blood pressure, and heart rate are measured via a catheter placed in the descending aorta and recorded radiometrically. Electrocardiogram are obtained by placing electrodes of transmitter in lead II. The endogenous release of renin is stimulated by two intramuscular injection of furosemide (5-(aminosulfonyl)-4-chloro-2-[(2-furanylmethyl)amino]benzoic acid) (10 mg/kg) 43 and 19 hours prior compound application. Test compounds are administered either directly into the femoral artery using an injection cannula or, in the form of a suspension or solution, via an oesophageal tube into the stomach, and their action on the blood pressure, heart rate and ECG are evaluated. In the in vivo test described, compounds of the present invention have hypotensive action at doses of from approximately 0.003 to approximately 0.3 mg/kg i.v. and at doses of from approximately 0.31 to approximately 30 mg/kg p.o.

The compounds of the present invention also have the property of regulating, especially reducing, intra-ocular pressure.

The extent of the reduction in intra-ocular pressure after administration of a pharmaceutical active ingredient of formula (I) according to the present invention can be determined, for example, in animals, for example rabbits or monkeys. Two typical experimental procedures that illustrate the present invention, but are not limited to in any way, are described hereinafter.

The in vivo test on a rabbit of the "Fauve de Bourgogne" type to determine the intra-ocular-pressure-reducing activity of topically applied compositions can be designed, for example, as follows: The intra-ocular pressure (IOP) is measured using an aplanation tonometer both before the experiment and at regular intervals of time. After a local anaesthetic has been administered, the suitably formulated test compound is applied topically in a precisely defined concentration (e.g. 0.000001-5% by weight) to one eye of the animal in question. The contralateral eye is treated, for example, with physiological saline. The measured values thus obtained are evaluated statistically.

The in vivo tests on monkeys of the species *Macaca Fascicularis* to determine the intra-ocular-pressure-reducing activity of topically applied compositions can be carried out, e.g., as follows: The suitably formulated test compound is applied in a precisely defined concentration (e.g. 0.000001-5% by weight) to one eye of each monkey. The other eye of the monkey is treated correspondingly, for example with physiological saline. Before the start of the test the animals are anaesthetised with intramuscular injections of, for example, ketamine. At regular intervals of time, the intra-ocular pressure (IOP) is measured. The test is carried out and evaluated in accordance with the rules of "good laboratory practice" (GLP).

Illustrative of the invention, the compound of Example 29 demonstrates inhibition of renin activity with an $IC_{50}$ value of about 0.3 nM in the FRET assay.

The following Examples are intended to illustrate the invention and are not to be construed as being limitations thereon. If not mentioned otherwise, all evaporations are performed under reduced pressure, preferably between about 10 and 100 mmHg (=20-133 mbar). The structure of final products, intermediates and starting materials is confirmed by standard analytical methods, e.g., microanalysis, melting point (m.p.) and spectroscopic characteristics, e.g., MS, LC/MS, IR, NMR. In general, abbreviations used are those conventional in the art.

EXAMPLE 1

General Procedure (I)

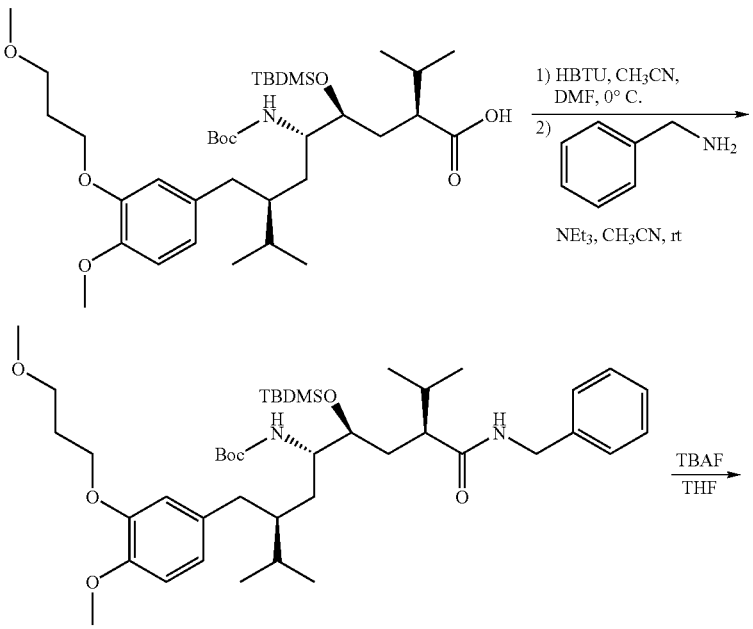

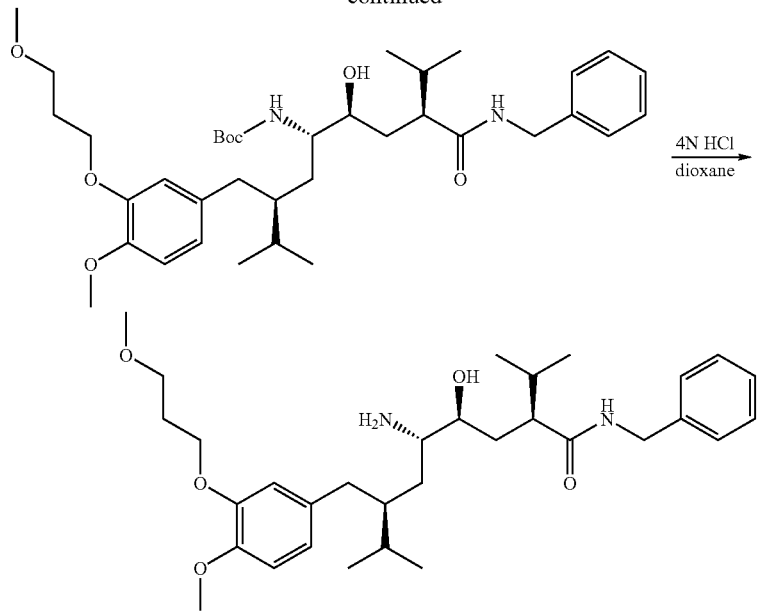

Preparation of the Starting Acid:

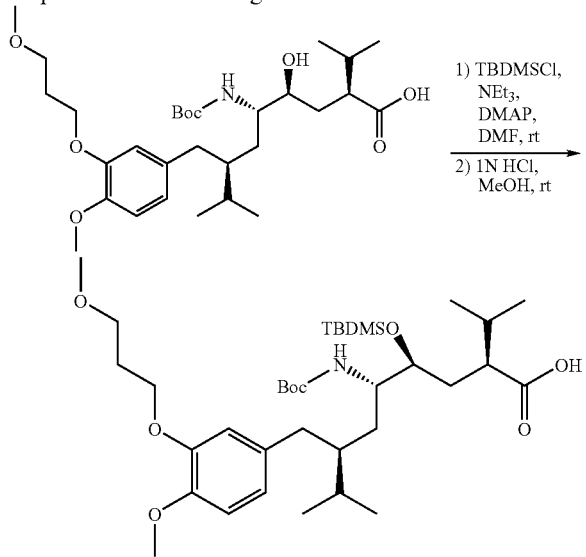

a) (2S,4S,5S,7S)-5-tert-Butoxycarbonylamino-4-(tert-butyl-dimethyl-silanyloxy)-2-isopropyl-7-[4-methoxy-3-(3-methoxy-propoxy)-benzyl]-8-methyl-nonanoic acid

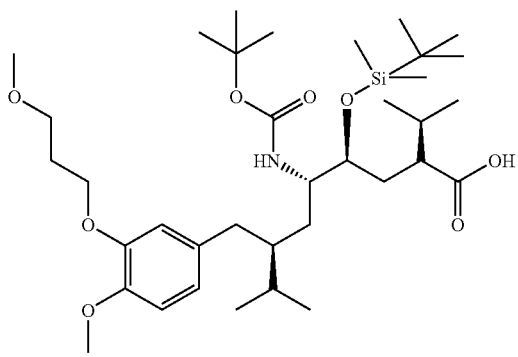

Triethylamine (NEt$_3$) (7.2 mL, 51.6 mmol, 3.0 equiv.) followed by dimethylamino-pyridine (DMAP) (640 mg, 5.2 mmol, 0.3 equiv.) is added to a solution of (2S,4S,5S,7S)-5-tert-butoxycarbonyl amino-4-hydroxy-2-isopropyl-7-[4-methoxy-3-(3-methoxy-propoxy)-benzyl]-8-methyl-nonanoic acid (9.53 g, 17.2 mmol, 1.0 equiv.) and TBDMSCl (10.3 g, 68.7 mmol, 4.0 equiv.) in dimethylformamide (DMF) (100 mL) at room temperature (RT). The reaction mixture is stirred at RT for 16 hours before water (H$_2$O) is added. Extraction with ethyl acetate (EtOAc), drying [sodium sulphate (Na$_2$SO$_4$)] and evaporation of the solvent affords the crude product. Flash column chromatography [600 g silicon dioxide (SiO$_2$), hexane:EtOAc 5:1] yields the double TBDMS-protected product as a colorless oil.

A portion thereof (904 mg, 1.24 mmol, 1.0 equiv.) is dissolved in methyl alcohol (MeOH) (20 mL) and 1 M HCl (2 mL, 2 mmol, 1.6 equiv.) is added. The mixture is stirred at RT for 10 minutes before 1 M sodium hydroxide (NaOH) (2 mL) followed by H$_2$O and a 10% citric acid solution are added for workup. Extraction with EtOAc, drying (Na$_2$SO$_4$) of the combined organic extracts and evaporation of the solvent give the crude product which is purified by flash column chromatography [50 g SiO$_2$, CH$_2$Cl$_2$:MeOH (9:1)] to afford the desired product as a colorless oil. MS (LC-MS): 691.3 [M+Na]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 7.63 minutes.

b) ((1S,2S,4S)-4-Benzylcarbamoyl-2-(tert-butyl-dimethyl-silanyloxy)-1-{(S)-2-[4-methoxy-3-(3-methoxy-propoxy)-benzyl]-3-methyl-butyl}-5-methyl-hexyl)-carbamic acid tert-butyl ester

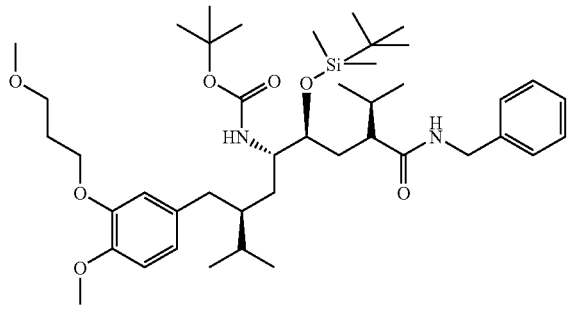

HBTU (400 mg, 1.03 mmol, 1.2 equiv.) is added to a solution of (2S,4S,5S,7S)-5-tert-butoxycarbonylamino-4-(tert-butyl-dimethyl-silanyloxy)-2-isopropyl-7-[4-methoxy-3-(3-methoxy-propoxy)-benzyl]-8-methyl-nonanoic acid (575 mg, 0.86 mmol, 1.0 equiv.) in acetonitrile ($CH_3CN$) (15 mL) and DMF (1 mL) at 0° C. After 5 minutes, a solution of benzylamine (94 μL, 0.86 mmol, 1.0 equiv.) and $Net_3$ (1.2 mL, 8.6 mmol, 10 equiv.) in $CH_3CN$ (3 mL) is added and the reaction mixture is stirred at room temperature for 5 minutes. For workup EtOAc is added and the organic layer is washed with 1 N HCl, a saturated solution of sodium bicarbonate ($NaHCO_3$) and brine. Drying ($Na_2SO_4$) of the organic phase and evaporation of the solvent affords the crude product which is purified by flash column chromatography [50 g $SiO_2$, hexane:EtOAc (4:1)] to afford the desired product as a colorless foam. MS (LC-MS): 780.4 $[M+Na]^+$; $R_f$ [hexane: EtOAc (1:1)]: 0.65 minutes.

c) ((1S,2S,4S)-4-Benzylcarbamoyl-2-hydroxy-1-{(S)-2-[4-methoxy-3-(3-methoxy-propoxy)-benzyl]-3-methyl-butyl}-5-methyl-hexyl)-carbamic acid tert-butyl ester

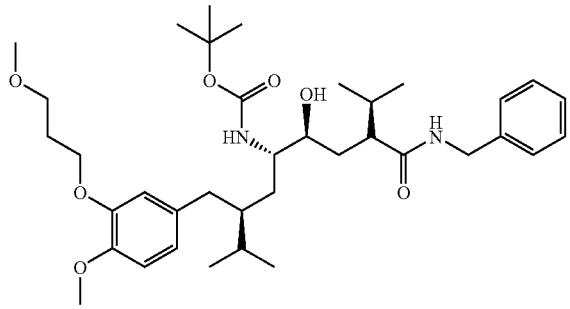

TBAF.$3H_2O$ (302 mg, 0.96 mmol, 1.5 equiv.) is added to a solution of ((1S,2S,4S)-4-benzylcarbamoyl-2-(tert-butyl-dimethyl-silanyloxy)-1-{(S)-2-[4-methoxy-3-(3-methoxy-propoxy)-benzyl]-3-methyl-butyl}-5-methyl-hexyl)-carbamic acid tert-butyl ester (485 mg, 0.64 mmol, 1.0 equiv.) in tetrahydrofuran (THF) (6 mL) at RT. After 1 hour, $H_2O$ is added and the mixture is extracted with EtOAc. The combined extracts are dried ($Na_2SO_4$) and the solvent is evaporated. Flash column chromatography [50 g $SiO_2$, hexane: EtOAc (3:1)] yields the desired product as a colorless foam. MS (LC-MS): 665.3 $[M+Na]^+$; $R_f$ [hexane:EtOAc (1:1)]: 0.33 minutes.

d) (2S,4S,5S,7S)-5-Amino-4-hydroxy-2-isopropyl-7-[4-methoxy-3-(3-methoxy-propoxy)-benzyl]-8-methyl-nonanoic acid benzylamide

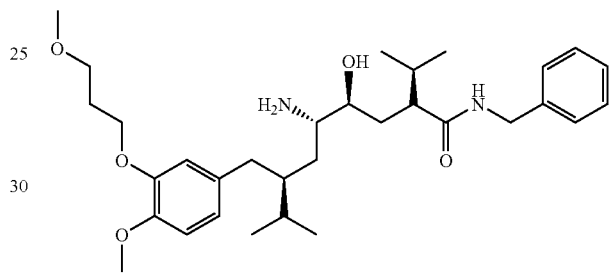

At 0° C. 4 N HCl/dioxane (7 mL, 28 mmol) is added to ((1S,2S,4S)-4-benzylcarbamoyl-2-hydroxy-1-{(S)-2-[4-methoxy-3-(3-methoxy-propoxy)-benzyl]-3-methyl-butyl}-5-methyl-hexyl)-carbamic acid tert-butyl ester (214 mg, 0.34 mmol, 1.0 equiv.). The resulting solution is stirred at RT for 15 minutes whereupon a saturated solution of $NaHCO_3$ is carefully added. The mixture is extracted with EtOAc, the combined extracts are dried ($Na_2SO_4$) and the solvent is evaporated. Flash column chromatography [20 g $SiO_2$, $CH_2Cl_2$:MeOH (9:1) to $CH_2Cl_2$:MeOH (9:1)+1% $NEt_3$] affords the product as a colorless oil. MS (LC-MS): 544.3 $[M+H]^+$; $R_f$[$CH_2Cl_2$:MeOH (9:1)]: 0.19 minutes.

EXAMPLE 2

General Procedure (II)

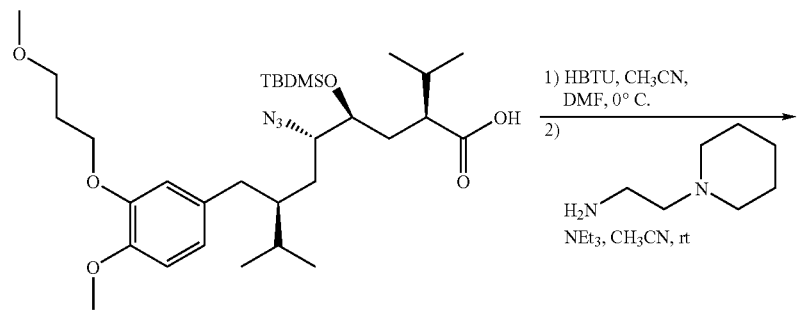

-continued

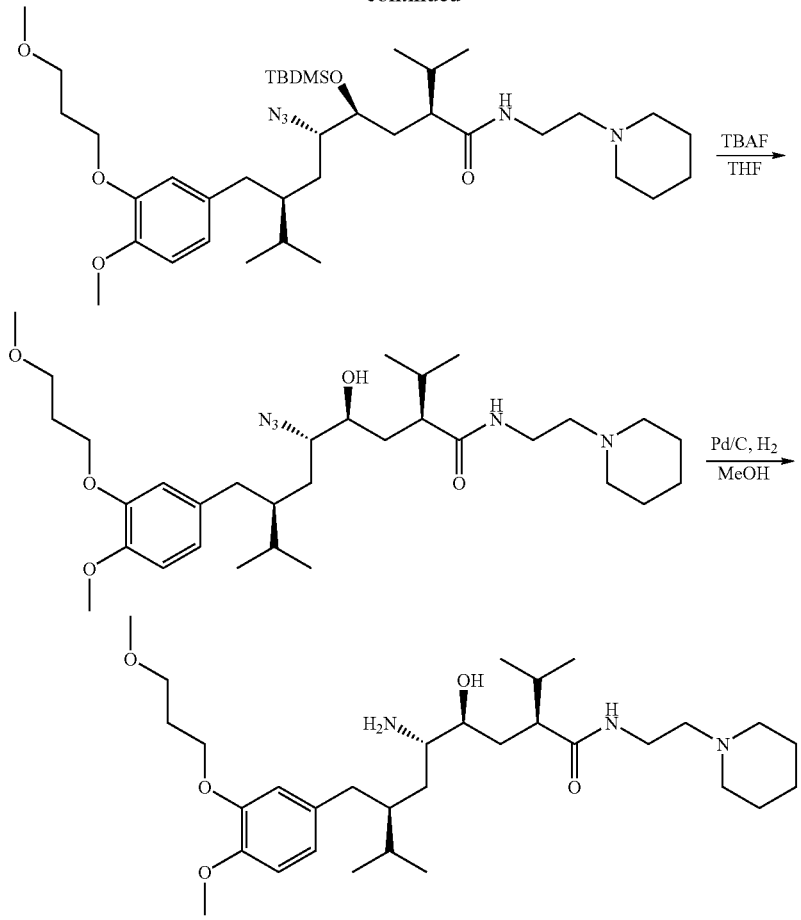

Preparation of the Starting Acid:

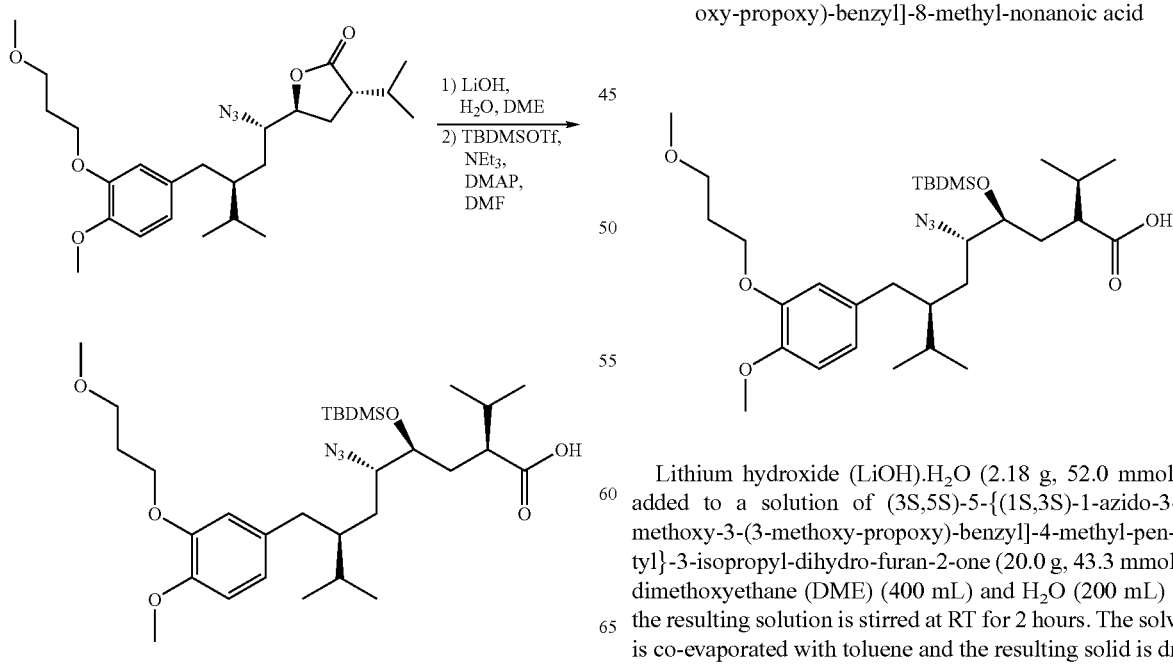

a) (2S,4S,5S,7S)-5-Azido-4-(tert-butyl-dimethyl-silanyloxy)-2-isopropyl-7-[4-methoxy-3-(3-methoxy-propoxy)-benzyl]-8-methyl-nonanoic acid Lithium hydroxide (LiOH).H$_2$O (2.18 g, 52.0 mmol) is added to a solution of (3S,5S)-5-{(1S,3S)-1-azido-3-[4-methoxy-3-(3-methoxy-propoxy)-benzyl]-4-methyl-pentyl}-3-isopropyl-dihydro-furan-2-one (20.0 g, 43.3 mmol) in dimethoxyethane (DME) (400 mL) and H$_2$O (200 mL) and the resulting solution is stirred at RT for 2 hours. The solvent is co-evaporated with toluene and the resulting solid is dried under high vacuum.

This residue is dissolved in DMF (160 mL) and NEt$_3$ (32 mL, 227.6 mmol), TBDMSOTf (41.8 mL, 182.1 mmol) and DMAP (556 mg, 4.6 mmol) are added sequentially. The mixture is stirred at RT for 16 hours. For workup, EtOAc is added and the mixture is quenched by addition of a saturated solution of NaHCO$_3$. The organic phase is separated and the aqueous phase is extracted with EtOAc. Evaporation of the solvent of the combined organic extracts affords bis-TBDMS protected product (32.4 g) while acidification of the basic aqueous layer with 1 N HCl followed by extraction with EtOAc and evaporation of the solvent yields the corresponding mono-silylated free acid (8.8 g). Both isolated products are combined and subjected to flash column chromatography [hexane:EtOAc (4:1) to hexane:EtOAc (1:1)] to give the desired mono-silylated acid as a viscous oil (complete desilylation of the silyl-protected acid during chromatography). MS (LC-MS): 616.0 [M+Na]$^+$; $t_R$ (HPLC, C8 column, 20-95% CH$_3$CN/H$_2$O/3.5 minute, 95% CH$_3$CN/1 minute, flow: 0.8 mL/min.): 3.93 minutes.

b) (2S,4S,5S,7S)-5-Azido-4-(tert-butyl-dimethyl-silanyloxy)-2-isopropyl-7-[4-methoxy-3-(3-methoxy-propoxy)-benzyl]-8-methyl-nonanoic acid (2-piperidin-1-yl-ethyl)-amide

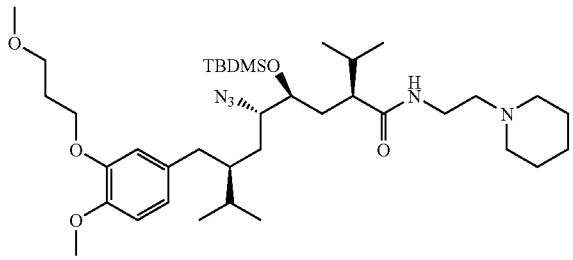

HBTU (1.20 g, 3.0 mmol) was added to a solution of (2S,4S,5S,7S)-5-azido-4-(tert-butyl-dimethyl-silanyloxy)-2-isopropyl-7-[4-methoxy-3-(3-methoxy-propoxy)-benzyl]-8-methyl-nonanoic acid (1.50 g, 2.5 mmol) in CH$_3$CN (50 mL). Then 2-aminoethylpiperidine (324 mg, 2.5 mmol) and NEt$_3$ (3.9 mL) were added and the resulting solution was stirred at RT for 2.5 hours. For workup, EtOAc was added and the organic phase was washed with 1 N HCl, saturated NaHCO$_3$ solution and brine. Drying of the organic phase (Na$_2$SO$_4$) and evaporation of the solvent affords the crude product which is purified by flash column chromatography [CH$_2$Cl$_2$:MeOH (95:5)] to give the desired product as a colorless oil. MS (LC-MS): 705.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 6.82 minutes.

c) (2S,4S,5S,7S)-5-Azido-4-hydroxy-2-isopropyl-7-[4-methoxy-3-(3-methoxy-propoxy)-benzyl]-8-methyl-nonanoic acid (2-piperidin-1-yl-ethyl)-amide

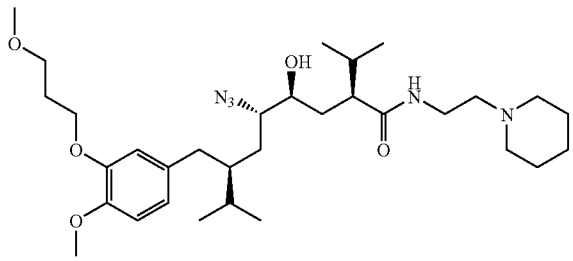

TBAF.3H$_2$O (1.73 g, 5.5 mmol) is added to a solution of (2S,4S,5S,7S)-5-azido-4-(tert-butyl-dimethyl-silanyloxy)-2-isopropyl-7-[4-methoxy-3-(3-methoxy-propoxy)-benzyl]-8-methyl-nonanoic acid (2-piperidin-1-yl-ethyl)-amide (1.54 g, 2.2 mmol) in THF (15 mL). The reaction mixture is stirred at RT for 72 hours. For workup, H$_2$O is added and the mixture is extracted with CH$_2$Cl$_2$. The combined organic extracts are dried (Na$_2$SO$_4$) and the solvent is evaporated. Flash column chromatography [CH$_2$Cl$_2$:MeOH (9:1)] yields the desired product as a yellowish oil. MS (LC-MS): 590.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.24 minutes.

d) (2S,4S,5S,7S)-5-Amino-4-hydroxy-2-isopropyl-7-[4-methoxy-3-(3-methoxy-propoxy)-benzyl]-8-methyl-nonanoic acid (2-piperidin-1-yl-ethyl)-amide

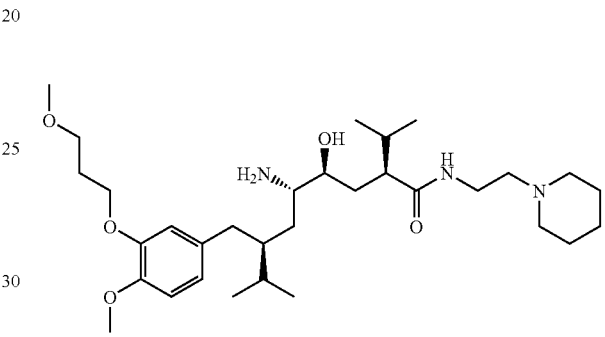

Palladium on carbon (Pd/C) 10% (200 mg) is added to a solution of (2S,4S,5S,7S)-5-azido-4-hydroxy-2-isopropyl-7-[4-methoxy-3-(3-methoxy-propoxy)-benzyl]-8-methyl-nonanoic acid (2-piperidin-1-yl-ethyl)-amide (780 mg, 1.32 mmol) in MeOH (40 mL) under Ar. Then the reaction suspension is stirred under a atmosphere of hydrogen (H$_2$) for 8 hours. The catalyst is filtered-off over Celite and washed with MeOH. Evaporation of the solvent gives the crude product which is pure according to analysis and used without further purification. MS (LC-MS): 564.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.31 minutes.

EXAMPLE 3

General Procedure (III)

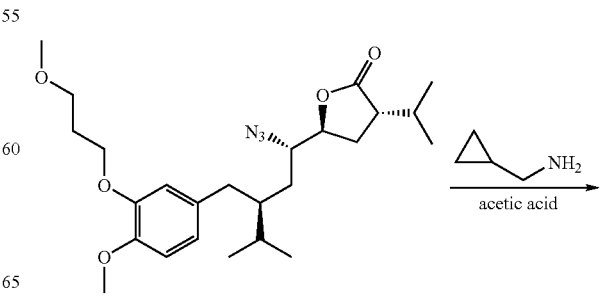

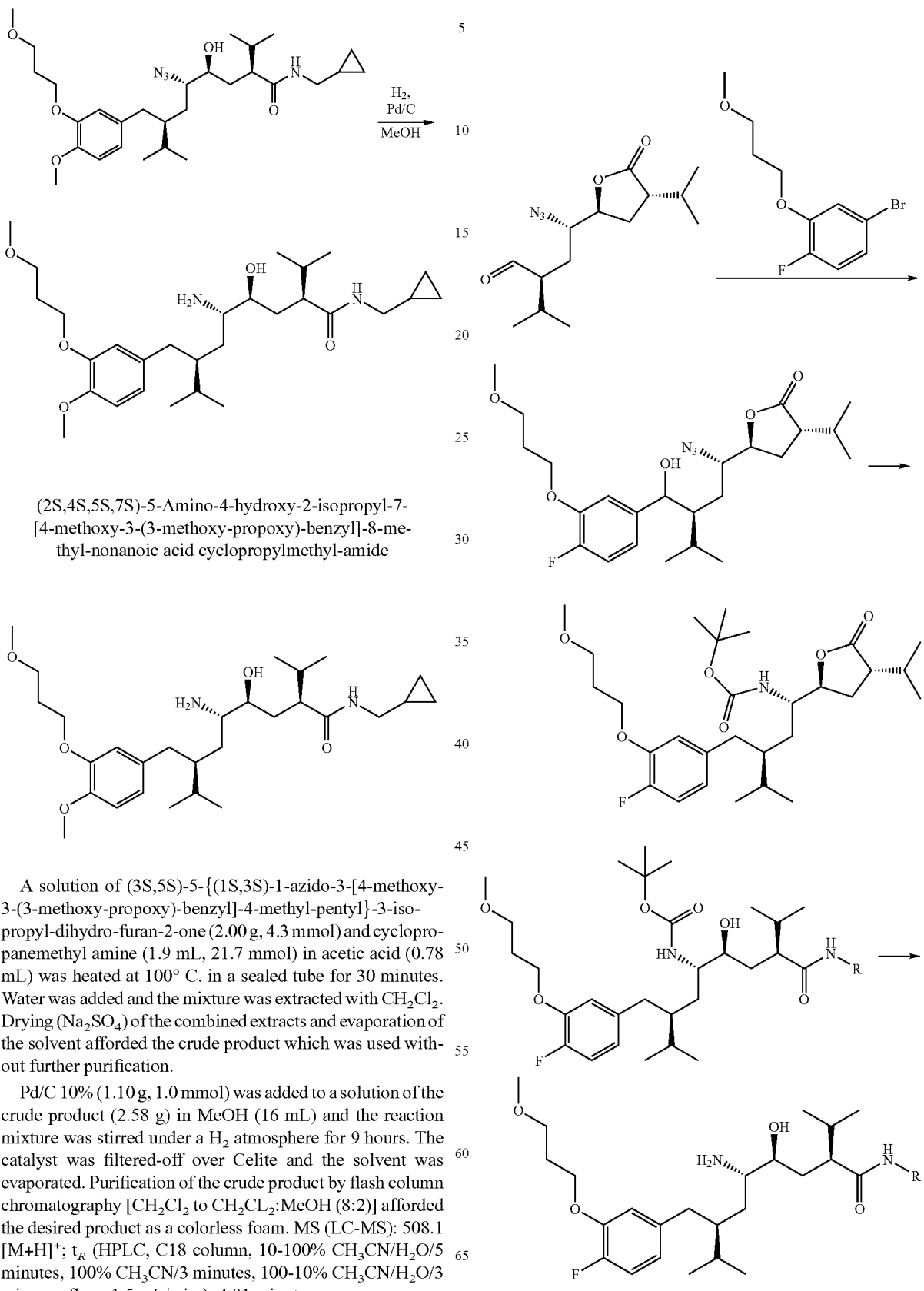

(2S,4S,5S,7S)-5-Amino-4-hydroxy-2-isopropyl-7-[4-methoxy-3-(3-methoxy-propoxy)-benzyl]-8-methyl-nonanoic acid cyclopropylmethyl-amide A solution of (3S,5S)-5-{(1S,3S)-1-azido-3-[4-methoxy-3-(3-methoxy-propoxy)-benzyl]-4-methyl-pentyl}-3-isopropyl-dihydro-furan-2-one (2.00 g, 4.3 mmol) and cyclopropanemethyl amine (1.9 mL, 21.7 mmol) in acetic acid (0.78 mL) was heated at 100° C. in a sealed tube for 30 minutes. Water was added and the mixture was extracted with $CH_2Cl_2$. Drying ($Na_2SO_4$) of the combined extracts and evaporation of the solvent afforded the crude product which was used without further purification.

Pd/C 10% (1.10 g, 1.0 mmol) was added to a solution of the crude product (2.58 g) in MeOH (16 mL) and the reaction mixture was stirred under a $H_2$ atmosphere for 9 hours. The catalyst was filtered-off over Celite and the solvent was evaporated. Purification of the crude product by flash column chromatography [$CH_2Cl_2$ to $CH_2CL_2$:MeOH (8:2)] afforded the desired product as a colorless foam. MS (LC-MS): 508.1 [M+H]$^+$; $t_R$ (HPLC, C18 column, 10-100% $CH_3CN/H_2O$/5 minutes, 100% $CH_3CN$/3 minutes, 100-10% $CH_3CN/H_2O$/3 minutes, flow: 1.5 mL/min.): 4.91 minutes.

EXAMPLE 4

General Procedure (IV)

a) 4-Bromo-1-fluoro-2-(3-methoxy-propoxy)-benzene

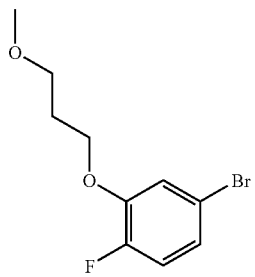

Azodicarbonic acid diisopropylester is added to a solution of 4-bromo-1-fluoro-2-hydroxy-benzene [see Maleczak, Jr., Shi, Holmes and Smith, *J Am Chem Soc*, Vol. 125, No. 26, pp. 7792-7793 (2003)] (5.52 g, 28.9 mmol, 1 equiv.), triphenylphosphine (8.4 g, 31.8 mmol, 1.1 equiv.) in THF (20 mL) and 3-methoxypropanol (3 mL, 31.8 mmol, 1.1 equiv.) in THF at RT and the solution is stirred for 16 hours, before the solvents are evaporated. Flash column chromatography [hexane:EtOAc (9:1) to hexane:EtOAc (4:1)] affords the product as a light yellow oil. MS (LC-MS): 264.9 [M+H]$^+$; $R_f$ [to hexane:EtOAc (4:1)]: 0.6 minutes.

b) (3S,5S)-5-((1S,3S)-1-Azido-3-{[4-fluoro-3-(3-methoxy-propoxy)-phenyl]-hydroxy-methyl}-4-methyl-pentyl)-3-isopropyl-dihydro-furan-2-one

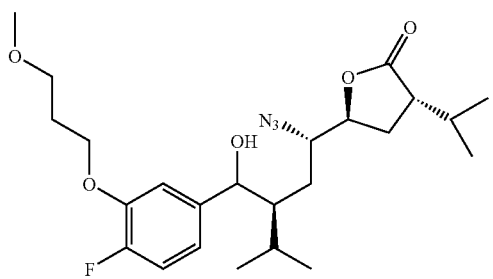

To a solution of 4-bromo-1-fluoro-2-(3-methoxy-propoxy)-benzene (1.94 g, 13.3 mmol, 1.4 equiv.) and N-methylmorpholine (1.6 mL, 14.7 mmol, 3 equiv.) in THF (20 mL) n-butyl lithium in hexane (1.6 M, 5.5 mL, 8.8 mmol, 1.8 equiv.) is added dropwise at −78° C. The solution is stirred at −78° C. for 1 hour, when a solution of MgBr$_2$ (14.7 mmol) in THF (50 mL), freshly prepared from magnesium (0.36 g, 14.7 mmol, 3 equiv.) and 1,2-dibromoethane (1.3 mL, 14.7 mmol, 3 equiv.), is added dropwise at −78° C. The reaction is stirred at the same temperature for 45 minutes, when (S)-2-[(S)-2-azido-2-((2S,4S)-4-isopropyl-5-oxo-tetrahydro-furan-2-yl)-ethyl]-3-methyl-butyraldehyde (1.4 g, 4.9 mmol, 1 equiv.) in THF (14 mL) is added dropwise at −78° C. The reaction mixture is stirred for an additional hour at the same temperature, before it is quenched with saturated aqueous NH$_4$Cl (20 mL) and warmed to RT. The mixture is extracted with EtOAc, the combined extracts are washed with brine, dried over Na$_2$SO$_4$ and the solvent is evaporated. Flash column chromatography [CH$_2$Cl$_2$ to CH$_2$Cl$_2$:acetone (9:1)] affords the product as a light yellow oil. MS (LC-MS): 488 [M+Na]$^+$; $R_f$ [CH$_2$Cl$_2$:acetone (98:2)]: 0.25 minutes.

The starting material (S)-2-[(S)-2-azido-2-((2S,4S)-4-isopropyl-5-oxo-tetrahydro-furan-2-yl)-ethyl]-3-methyl-butyraldehyde is prepared according to the methods described in EP 0 678 503 B1 and EP 0 678 514 A1.

c) (3S,5S)-5-{(1S,3S)-1-Amino-3-[4-fluoro-3-(3-methoxy-propoxy)-benzyl]-4-methyl-pentyl}-3-isopropyl-dihydro-furan-2-one

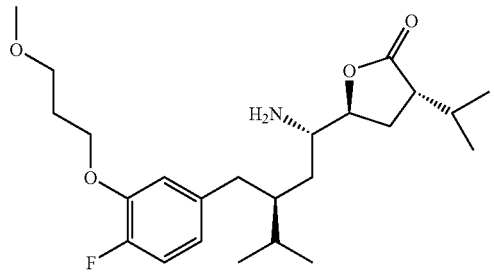

A solution of isobutyric acid (S)-2-[(S)-2-azido-2-((2S,4S)-4-isopropyl-5-oxo-tetrahydro-furan-2-yl)-ethyl]-1-[4-fluoro-3-(3-methoxy-propoxy)-phenyl]-3-methyl-butyl ester (1.45 g, 2.7 mmol, 1 equiv.), Pd/C (10%, 2.9 g) and ethanolamine (0.17 mL, 2.7 mmol, 1 equiv.) in ethanol (135 mL) were shaken under H$_2$ (1 atmosphere) for 24 hours. The reaction mixture is filtered, before the solvent is evaporated to afford the product as a light grey gum. MS (LC-MS): 424 [M+H]$^+$ d) [(1S,3S)-3-[4-Fluoro-3-(3-methoxy-propoxy)-benzyl]-1-((2S,4S)-4-isopropyl-5-oxo-tetrahydro-furan-2-yl)-4-methyl-pentyl]-carbamic acid tert-butyl ester

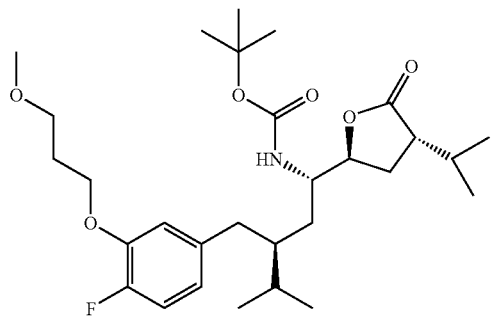

A solution of (3S,5S)-5-{(1S,3S)-1-amino-3-[4-fluoro-3-(3-methoxy-propoxy)-benzyl]-4-methyl-pentyl}-3-isopropyl-dihydro-furan-2-one (1.13 g, 2.7 mmol, 1 equiv.), di-tert-butyldicarbonate (2.1 g, 9.4 mmol) and diisopropylethylamine (1.83 mL, 10.7 mmol, 4 equiv.) in CH$_2$Cl$_2$ (20 mL) is stirred at RT for 164 hours. The solution is washed with aqueous HCl (1 M), saturated aqueous NaHCO$_3$ and brine, dried over Na$_2$SO$_4$ and the solvents are evaporated. Flash column chromatography [CH$_2$Cl$_2$ to CH$_2$Cl$_2$:acetone (95:5)] affords the product as a light yellow oil. MS (LC-MS): 546 [M+Na]$^+$; $R_f$(CH$_2$Cl$_2$:acetone (95:5)]: 0.71 minutes.

e) {(1S,2S,4S)-1-{(S)-2-[4-Fluoro-3-(3-methoxy-propoxy)-benzyl]-3-methyl-butyl}-2-hydroxy-4-[(1-hydroxymethyl-cyclopropylmethyl)-carbamoyl]-5-methyl-hexyl}-carbamic acid tert-butyl ester

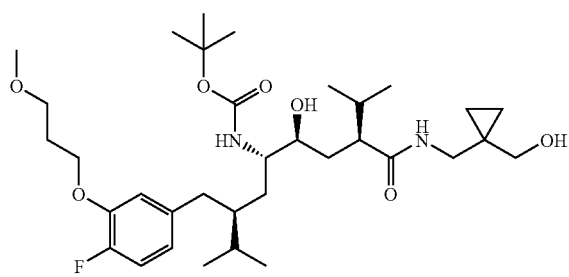

[(1S,3S)-3-[4-Fluoro-3-(3-methoxy-propoxy)-benzyl]-1-((2S,4S)-4-isopropyl-5-oxo-tetrahydro-furan-2-yl)-4-methyl-pentyl]-carbamic acid tert-butyl ester (100 g, 0.19 mmol, 1 eq), 3-amino-2,2-dimethylpropanol (0.3 g, 2.8 mmol, 15 eq) and acetic acid (0.11 μL, 0.002 mmol, 0.01 eq) are stirred at 60° C. during 24 hours, when the solvent is evaporated. Flash column chromatography (CH$_2$Cl$_2$/MeOH 95:5 to CH$_2$Cl$_2$/MeOH 9:1) affords the product as an light yellow solid. MS (LC-MS): 627 [M+H]$^+$; R$_f$ (CH$_2$Cl$_2$/MeOH 9:1): 0.25.

f) (2S,4S,5S,7S)-5-Amino-7-[4-fluoro-3-(3-methoxy-propoxy)-benzyl]-4-hydroxy-2-isopropyl-8-methyl-nonanoic acid (1-hydroxymethyl-cyclopropylmethyl)-amide

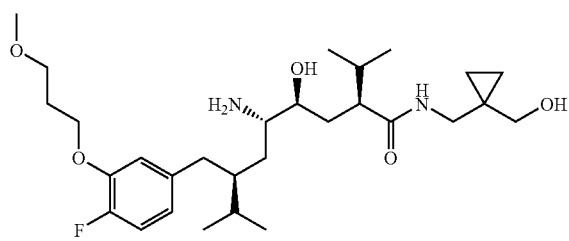

At 5° C. 4N HCl/dioxane (0.97 ml) is added to ((1S,2S,4S)-4-Cyclopropylcarbamoyl-1-{(S)-2-[4-fluoro-3-(3-methoxy-propoxy)-benzyl]-3-methyl-butyl}-2-hydroxy-5-methyl-hexyl)-carbamic acid tert-butyl ester (89 mg, 0.14 mmol, 1.0 eq) in dioxane (0.8 ml). The resulting solution is stirred at 5° C. for 1 h whereupon it is lyophilised. Flash column chromatography (CH$_2$Cl$_2$/MeOH (10% NH4OH) 95:5 to CH$_2$Cl$_2$/MeOH (10% NH4OH) 9:1) affords the product as a light yellow solid. MS (LC-MS): 527.1 [M+H]$^+$; R$_f$ (CH$_2$Cl$_2$/MeOH (10% NH4OH) 9:1): 0.16 minutes.

EXAMPLE 5

(2S,4S,5S,7S)-5-Amino-7-[4-fluoro-3-(3-methoxy-propoxy)-benzyl]-4-hydroxy-2-isopropyl-8-methyl-nonanoic acid (3-hydroxy-2,2-dimethyl-propyl)-amide The title compound prepared in accordance with General Procedure (IV).

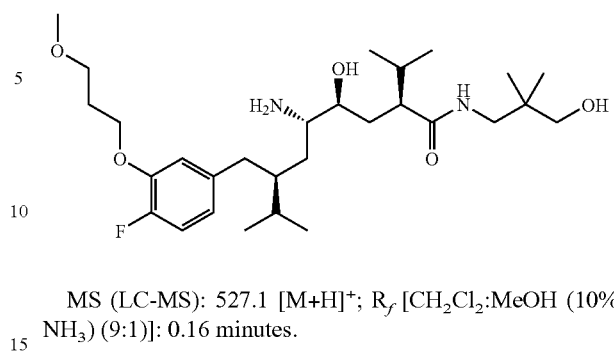

MS (LC-MS): 527.1 [M+H]$^+$; R$_f$ [CH$_2$Cl$_2$:MeOH (10% NH$_3$) (9:1)]: 0.16 minutes.

EXAMPLE 6

(2S,4S,5S,7S)-5-Amino-7-[4-fluoro-3-(3-methoxy-propoxy)-benzyl]-4-hydroxy-2-isopropyl-8-methyl-nonanoic acid (3-hydroxy-2,2-dimethyl-propyl)-amide The title compound prepared in accordance General Procedure (IV).

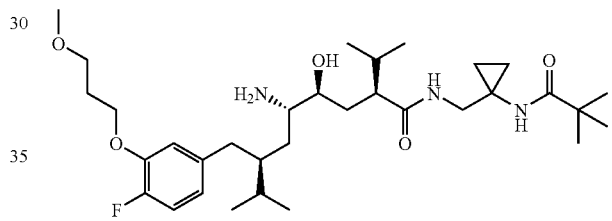

MS (LC-MS): 606.1 [M+H]$^+$; R$_f$ [CH$_2$Cl$_2$:MeOH (9:1)]: 0.16 minutes.

EXAMPLE 7

Cyclopropanecarboxylic acid [1-({(2S,4S,5S,7S)-5-amino-7-[4-fluoro-3-(3-methoxy-propoxy)-benzyl]-4-hydroxy-2-isopropyl-8-methyl-nonanoylamino}-methyl)-cyclopropyl]-amide The title compound prepared in accordance with General Procedure (II).

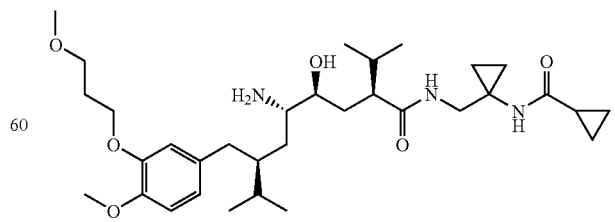

MS (LC-MS): 590.1 [M+H]$^+$; R$_f$ [CH$_2$Cl$_2$:MeOH (10% NH$_3$) (9:1)]: 0.16 minutes.

EXAMPLE 8

(2S,4S,5S,7S)-5-Amino-4-hydroxy-2-isopropyl-7-[4-methoxy-3-(3-methoxy-propoxy)-benzyl]-8-methyl-nonanoic acid (1-methoxymethyl-cyclopropylmethyl)-amide The title compound prepared in accordance with General Procedure (II).

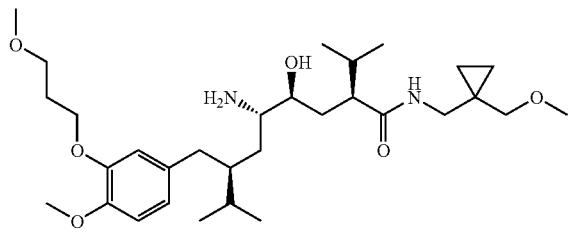

MS (LC-MS): 551 [M+H]$^+$; R$_f$[CH$_2$Cl$_2$:MeOH (9:1): 0.16 minutes.

EXAMPLE 9

(2S,4S,5S,7S)-5-Amino-4-hydroxy-2-isopropyl-7-[4-methoxy-3-(3-methoxy-propoxy)-benzyl]-8-methyl-nonanoic acid (1-hydroxymethyl-cyclopropylmethyl)-amide The title compound prepared in accordance with General Procedure (II).

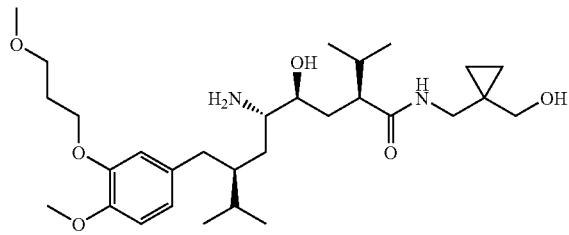

MS (LC-MS): 537 [M+H]$^+$; R$_f$[CH$_2$Cl$_2$:MeOH (9:1): 0.15 minutes.

EXAMPLE 10

(2S,4S,5S,7S)-5-Amino-4-hydroxy-2-isopropyl-7-[4-methoxy-3-(3-methoxy-propoxy)-benzyl]-8-methyl-nonanoic acid (2-fluoro-ethyl)-amide The title compound prepared in accordance with General Procedure (II).

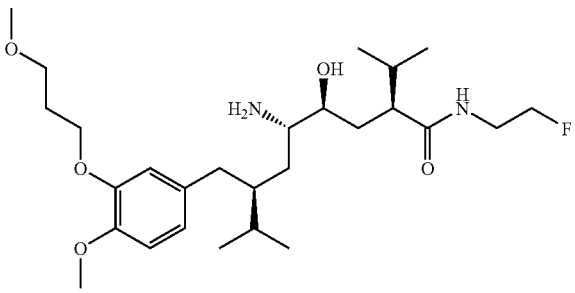

MS (LC-MS): 499.1 [M+H]$^+$; t$_R$ (HPLC, C8 column, 5-95% CH$_3$CN/H$_2$O/6.5 minutes, 95% CH$_3$CN/H$_2$O/1 minute, flow: 0.5 mL/min.): 4.63 minutes.

EXAMPLE 11

(2S,4S,5S,7S)-5-Amino-4-hydroxy-2-isopropyl-7-[4-methoxy-3-(3-methoxy-propoxy)-benzyl]-8-methyl-nonanoic acid (2,2-difluoro-ethyl)-amide The title compound prepared in accordance with General Procedure (I).

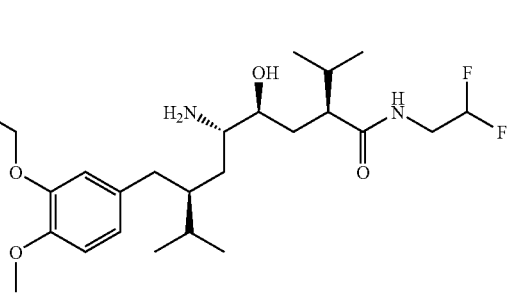

MS (LC-MS): 518.1 [M+H]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.75 minutes.

EXAMPLE 12

(2S,4S,5S,7S)-5-Amino-4-hydroxy-2-isopropyl-7-[4-methoxy-3-(3-methoxy-propoxy)-benzyl]-8-methyl-nonanoic acid (2,2,2-trifluoro-ethyl)-amide The title compound prepared in accordance with General Procedure (II).

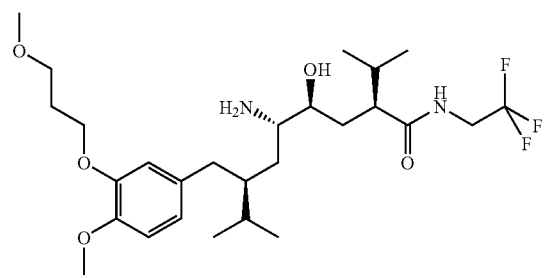

MS (LC-MS): 535.1 [M+H]$^+$; t$_R$ (HPLC, C8 column, 5-95% CH$_3$CN/H$_2$O/6.5 minutes, 95% CH$_3$CN/H$_2$O/1 minute, flow: 0.5 mL/min.): 4.9 minutes.

EXAMPLE 13

(2S,4S,5S,7S)-5-Amino-4-hydroxy-2-isopropyl-7-[4-methoxy-3-(3-methoxy-propoxy)-benzyl]-8-methyl-nonanoic acid cyclopropylmethyl-amide The title compound prepared in accordance with General Procedure (III).

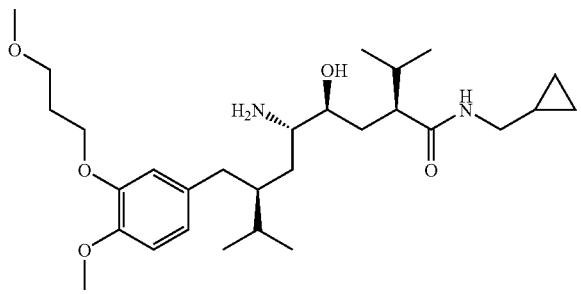

MS (LC-MS): 508.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.91 minutes.

EXAMPLE 14

(2S,4S,5S,7S)-5-Amino-4-hydroxy-2-isopropyl-7-[4-methoxy-3-(3-methoxy-propoxy)-benzyl]-8-methyl-nonanoic acid (1-cyclopropyl-1-methyl-ethyl)-amide The title compound prepared in accordance with General Procedure (I).

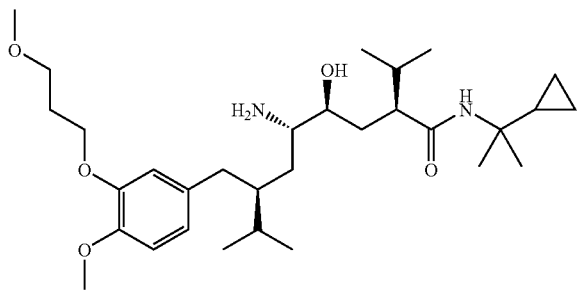

MS (LC-MS): 536.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.21 minutes.

EXAMPLE 15

(2S,4S,5S,7S)-5-Amino-4-hydroxy-2-isopropyl-7-[4-methoxy-3-(3-methoxy-propoxy)-benzyl]-8-methyl-nonanoic acid ((R)-1-cyclopropyl-ethyl)-amide The title compound prepared in accordance with General Procedure (I).

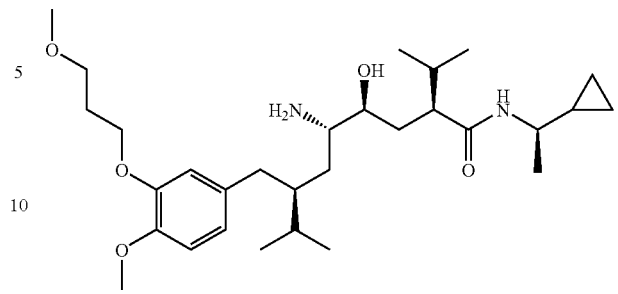

MS (LC-MS): 522.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.95 minutes.

EXAMPLE 16

(2S,4S,5S,7S)-5-Amino-4-hydroxy-2-isopropyl-7-[4-methoxy-3-(3-methoxy-propoxy)-benzyl]-8-methyl-nonanoic acid ((S)-1-cyclopropyl-ethyl)-amide The title compound prepared in accordance with General Procedure (I).

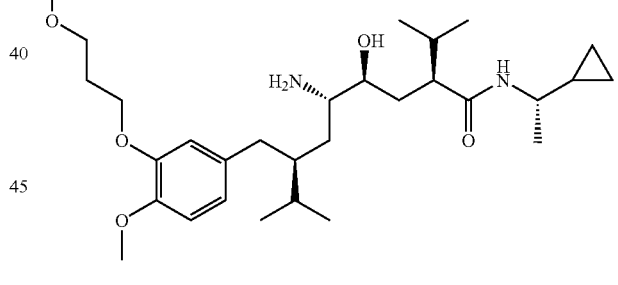

MS (LC-MS): 522.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.93 minutes.

EXAMPLE 17

(2S,4S,5S,7S)-5-Amino-4-hydroxy-2-isopropyl-7-[4-methoxy-3-(3-methoxy-propoxy)-benzyl]-8-methyl-nonanoic acid (2,2-dimethyl-cyclopropylmethyl)-amide The title compound prepared in accordance with General Procedure (I).

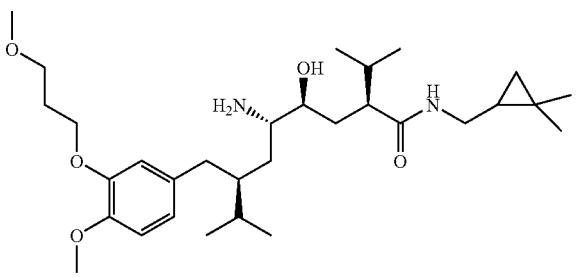

MS (LC-MS): 536.1 [M+H]⁺; $t_R$ (HPLC, C8 column, 5-95% CH₃CN/H₂O/6.5 minutes, 95% CH₃CN/H₂O/1 minute, flow: 0.5 mL/min.): 4.81 minutes.

EXAMPLE 18

(2S,4S,5S,7S)-5-Amino-4-hydroxy-2-isopropyl-7-[4-methoxy-3-(3-methoxy-propoxy)-benzyl]-8-methyl-nonanoic acid [(1R,3S)-2,2-dimethyl-3-(2-methyl-propenyl)-cyclopropylmethyl]-amide The title compound prepared in accordance with General Procedure (I).

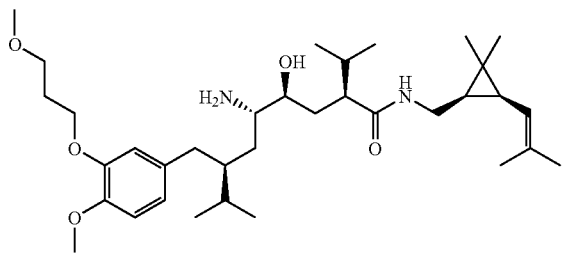

MS (LC-MS): 590.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.70 minutes.

EXAMPLE 19

(2S,4S,5S,7S)-5-Amino-4-hydroxy-2-isopropyl-7-[4-methoxy-3-(3-methoxy-propoxy)-benzyl]-8-methyl-nonanoic acid ((R)-1-cyclobutyl-ethyl)-amide The title compound prepared in accordance with General Procedure (I).

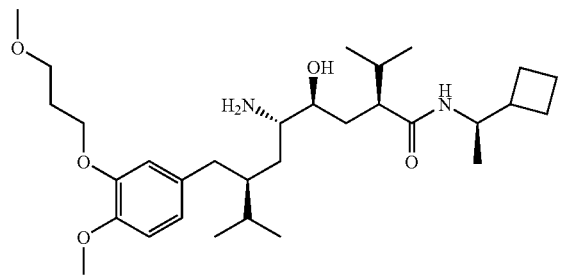

MS (LC-MS): 536.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.12 minutes.

EXAMPLE 20

(2S,4S,5S,7S)-5-Amino-4-hydroxy-2-isopropyl-7-[4-methoxy-3-(3-methoxy-propoxy)-benzyl]-8-methyl-nonanoic acid ((S)-1-cyclobutyl-ethyl)-amide The title compound prepared in accordance with General Procedure (I).

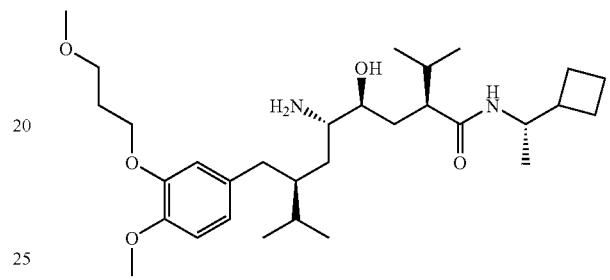

MS (LC-MS): 536.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.15 minutes.

EXAMPLE 21

(2S,4S,5S,7S)-5-Amino-4-hydroxy-2-isopropyl-7-[4-methoxy-3-(3-methoxy-propoxy)-benzyl]-8-methyl-nonanoic acid cyclopentylmethyl-amide The title compound prepared in accordance with General Procedure (I).

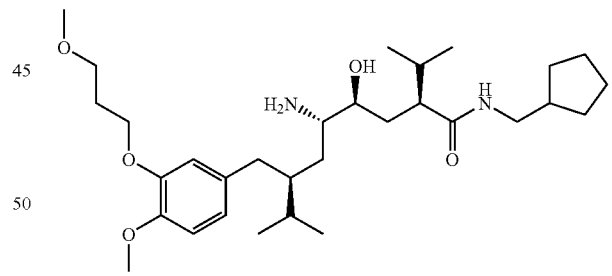

MS (LC-MS): 535.4 [M]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.15 minutes.

EXAMPLE 22

(2S,4S,5S,7S)-5-Amino-4-hydroxy-2-isopropyl-7-[4-methoxy-3-(3-methoxy-propoxy)-benzyl]-8-methyl-nonanoic acid ((S)-1-cyclopentyl-ethyl)-amide The title compound prepared in accordance with General Procedure (I).

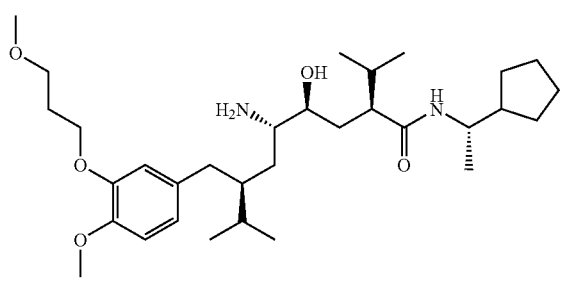

MS (LC-MS): 550.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.25 minutes.

EXAMPLE 23

(2S,4S,5S,7S)-5-Amino-4-hydroxy-2-isopropyl-7-[4-methoxy-3-(3-methoxy-propoxy)-benzyl]-8-methyl-nonanoic acid ((R)-1-cyclopentyl-ethyl)-amide The title compound prepared in accordance with General Procedure (I).

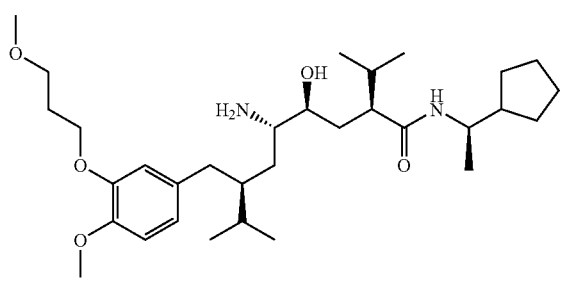

MS (LC-MS): 550.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.24 minutes.

EXAMPLE 24

(2S,4S,5S,7S)-5-Amino-4-hydroxy-2-isopropyl-7-[4-methoxy-3-(3-methoxy-propoxy)-benzyl]-8-methyl-nonanoic acid ((R)-2,2-dimethyl-cyclopentyl)-amide The title compound prepared in accordance with General Procedure (I).

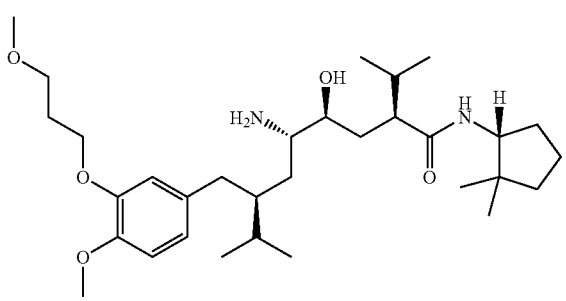

MS (LC-MS): 550.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.27 minutes.

EXAMPLE 25

(2S,4S,5S,7S)-5-Amino-4-hydroxy-2-isopropyl-7-[4-methoxy-3-(3-methoxy-propoxy)-benzyl]-8-methyl-nonanoic acid ((S)-2,2-dimethyl-cyclopentyl)-amide The title compound prepared in accordance with General Procedure (I).

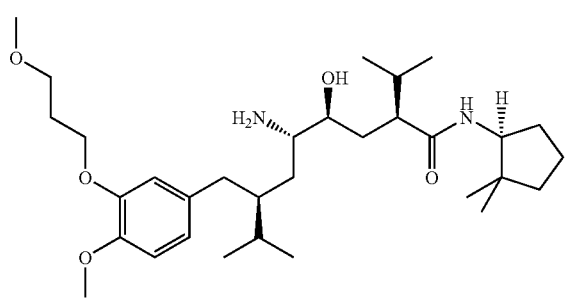

MS (LC-MS): 550.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.25 minutes.

EXAMPLE 26

(2S,4S,5S,7S)-5-Amino-4-hydroxy-2-isopropyl-7-[4-methoxy-3-(3-methoxy-propoxy)-benzyl]-8-methyl-nonanoic acid (1-methyl-cyclopentyl)-amide The title compound prepared in accordance with General Procedure (II).

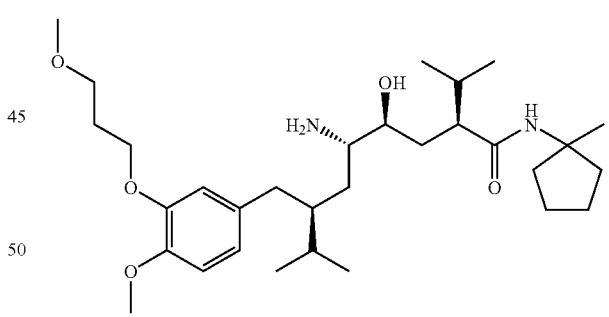

MS (LC-MS): 535.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.08 minutes.

EXAMPLE 27

(2S,4S,5S,7S)-5-amino-N-((1-fluorocyclopentyl)methyl)-4hydroxy-2isopropyl1-7-4-methoxy-3-(3-methoxypropoxy)benzyl)-8-methylnonanamide The title compound prepared in accordance with General Procedure (II).

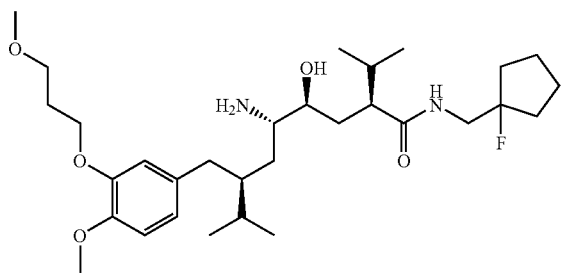

MS (LC-MS): 554 [M+H]⁺; $t_R$ (HPLC, C8 column, 5-95% CH$_3$CN/H$_2$O/ 6.5 minutes, 95% CH$_3$CN/H$_2$O/1 minute, flow: 0.5 mL/min.): 5.42 minutes.

EXAMPLE 28

(2S,4S,5S,7S)-5-Amino-4-hydroxy-2-isopropyl-7-[4-methoxy-3-(3-methoxy-propoxy)-benzyl]-8-methyl-nonanoic acid cyclohexylmethyl-amide The title compound prepared in accordance with General Procedure (I).

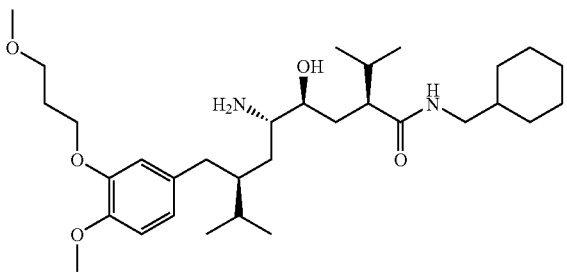

MS (LC-MS): 549.3 [M]⁺; $t_R$ (HPLC, C8 column, 5-95% CH$_3$CN/H$_2$O/6.5 minutes, 95% CH$_3$CN/H$_2$O/1 minute, flow: 0.5 mL/min.): 3.87 minutes.

EXAMPLE 29

(2S,4S,5S,7S)-5-Amino-4-hydroxy-2-isopropyl-7-[4-methoxy-3-(3-methoxy-propoxy)-benzyl]-8-methyl-nonanoic acid ((S)-1-cyclohexyl-ethyl)-amide The title compound prepared in accordance with General Procedure (I).

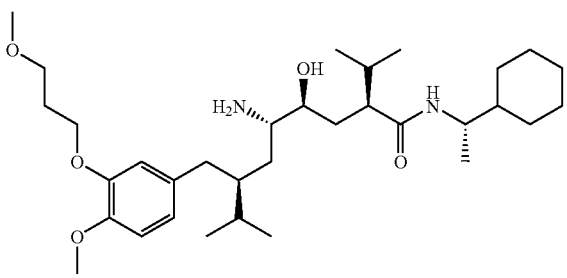

MS (LC-MS): 564.0 [M+H]⁺; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.36 minutes.

EXAMPLE 30

(2S,4S,5S,7S)-5-Amino-4-hydroxy-2-isopropyl-7-[4-methoxy-3-(3-methoxy-propoxy)-benzyl]-8-methyl-nonanoic acid ((R)-1-cyclohexyl-ethyl)-amide The title compound prepared in accordance with General Procedure (I).

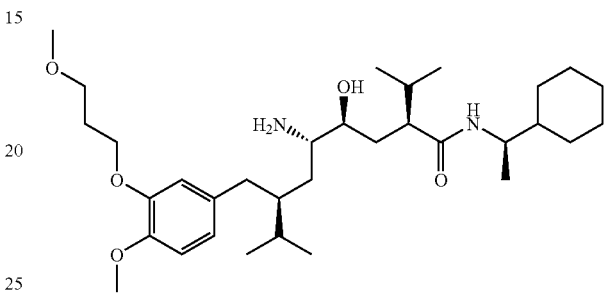

MS (LC-MS): 564.0 [M+H]⁺; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.38 minutes.

EXAMPLE 31

(2S,4S,5S,7S)-5-Amino-4-hydroxy-2-isopropyl-7-[4-methoxy-3-(3-methoxy-propoxy)-benzyl]-8-methyl-nonanoic acid cycloheptylmethyl-amide The title compound prepared in accordance with General Procedure (I).

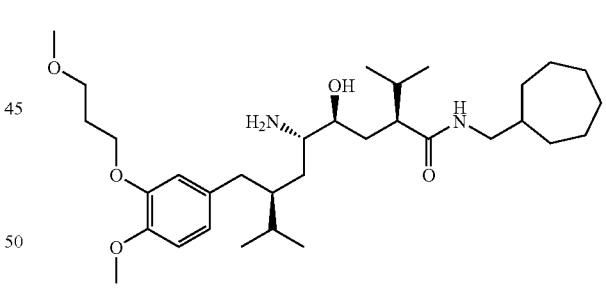

MS (LC-MS): 563.2 [M]⁺; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.62 minutes.

EXAMPLE 32

(2S,4S,5S,7S)-5-Amino-4-hydroxy-2-isopropyl-7-[4-methoxy-3-(3-methoxy-propoxy)-benzyl]-8-methyl-nonanoic acid (1,7,7-trimethyl-bicyclo[2.2.1]hept-2-yl)-amide The title compound prepared in accordance with General Procedure (I).

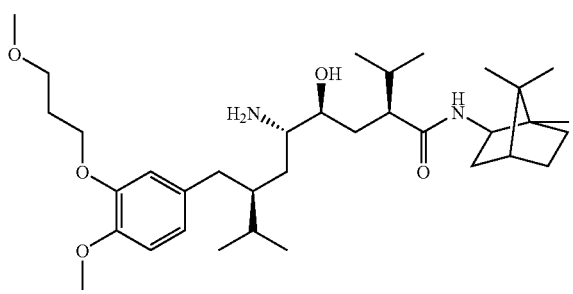

MS (LC-MS): 590.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.71 minutes.

EXAMPLE 33

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopropanecarboxylic acid methyl ester The title compound prepared in accordance with General Procedure (I).

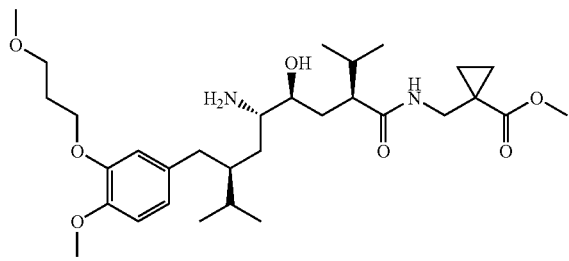

MS (LC-MS): 566.0 [M+H]$^+$; $t_R$ (HPLC, C8 column, 20-95% CH$_3$CN/H$_2$O/3.5 minutes, 95% CH$_3$CN/1 minute, flow: 0.8 mL/min.): 2.44 minutes.

EXAMPLE 34

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclobutanecarboxylic acid methyl ester The title compound prepared in accordance with General Procedure (I).

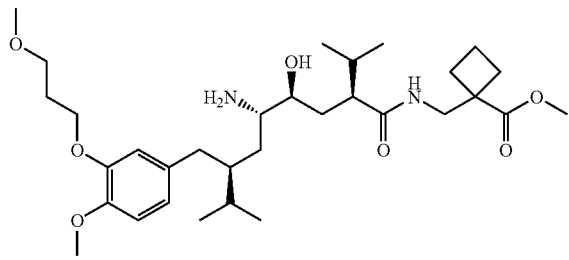

MS (LC-MS): 580.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.11 minutes.

EXAMPLE 35

1-{(2S,4S,5S,7S)-5-Amino-4-hydroxy-2-isopropyl-7-[4-methoxy-3-(3-methoxy-propoxy)-benzyl]-8-methyl-nonanoylamino}-cyclopentanecarboxylic acid methyl ester The title compound prepared in accordance with General Procedure (I).

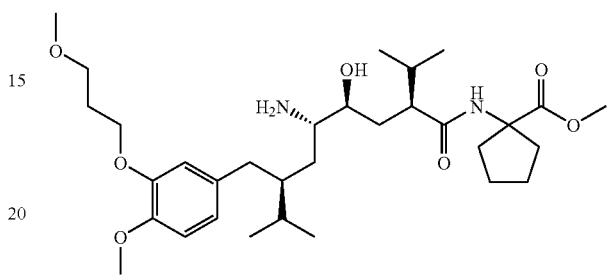

MS (LC-MS): 580.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.02 minutes.

EXAMPLE 36

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopentanecarboxylic acid methyl ester The title compound prepared in accordance with General Procedure (I).

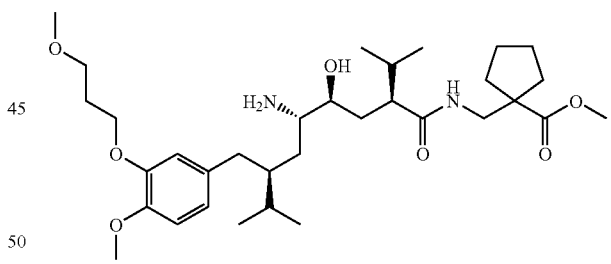

MS (LC-MS): 594.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.19 minutes.

EXAMPLE 37

1-{(2S,4S,5S,7S)-5-Amino-4-hydroxy-2-isopropyl-7-[4-methoxy-3-(3-methoxy-propoxy)-benzyl]-8-methyl-nonanoylamino}-cyclohexanecarboxylic acid methyl ester The title compound prepared in accordance with General Procedure (I).

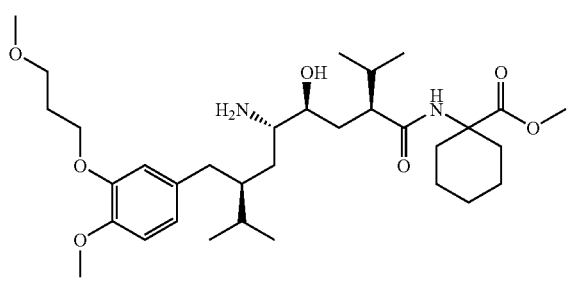

MS (LC-MS): 594.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.13 minutes.

EXAMPLE 38

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclohexanecarboxylic acid methyl ester The title compound prepared in accordance with General Procedure (I).

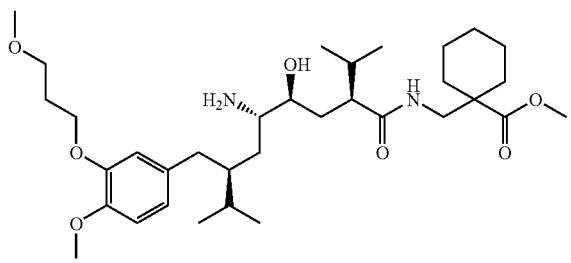

MS (LC-MS): 608.0 [M+H]$^+$; $t_R$ (HPLC, C8 column, 20-95% CH$_3$CN/H$_2$O/3.5 minutes, 95% CH$_3$CN/1 minute, flow: 0.8 mL/min.): 2.74 minutes.

EXAMPLE 39

(S)-{(2S,4S,5S,7S)-5-Amino-4-hydroxy-2-isopropyl-7-[4-methoxy-3-(3-methoxy-propoxy)-benzyl]-8-methyl-nonanoylamino}-cyclohexyl-acetic acid methyl ester The title compound prepared in accordance with General Procedure (I).

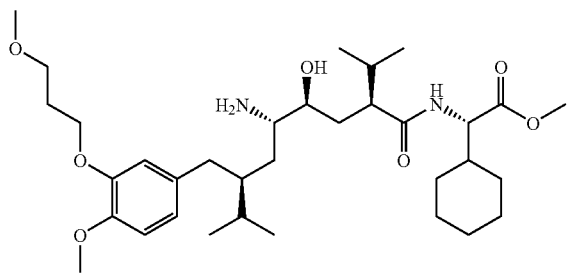

MS (LC-MS): 608.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.26 minutes.

EXAMPLE 40

(1S,3R)-3-{(2S,4S,5S,7S)-5-Amino-4-hydroxy-2-isopropyl-7-[4-methoxy-3-(3-methoxy-propoxy)-benzyl]-8-methyl-nonanoylamino}-cyclopentanecarboxylic acid methyl ester The title compound prepared in accordance with General Procedure (I).

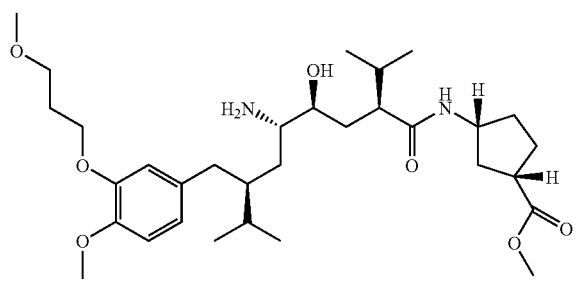

MS (LC-MS): 580.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.10 minutes.

EXAMPLE 41

(1S,3R)-3-{(2S,4S,5S,7S)-5-Amino-4-hydroxy-2-isopropyl-7-[4-methoxy-3-(3-methoxy-propoxy)-benzyl]-8-methyl-nonanoylamino}-cyclopentanecarboxylic acid methyl ester The title compound prepared in accordance with General Procedure (I).

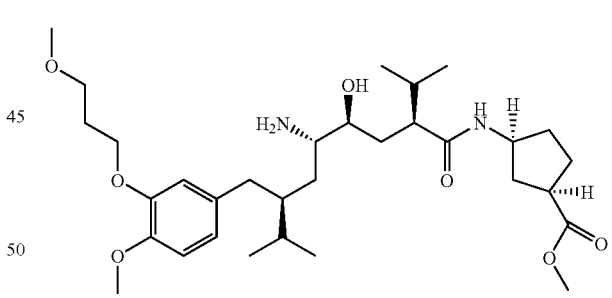

MS (LC-MS): 580.0 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.36 minutes.

EXAMPLE 42

4-{(2S,4S,5S,7S)-5-Amino-4-hydroxy-2-isopropyl-7-[4-methoxy-3-(3-methoxy-propoxy)-benzyl]-8-methyl-nonanoylamino}-cyclohexanecarboxylic acid methyl ester The title compound prepared in accordance with General Procedure (I).

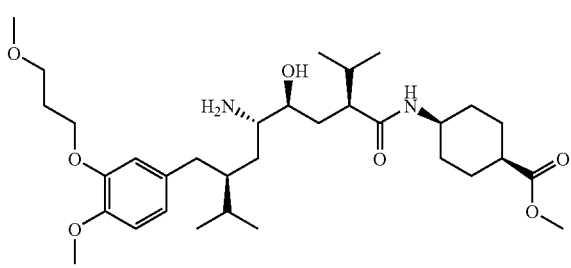

MS (LC-MS): 594.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.08 minutes.

EXAMPLE 43

4-{(2S,4S,5S,7S)-5-Amino-4-hydroxy-2-isopropyl-7-[4-methoxy-3-(3-methoxy-propoxy)-benzyl]-8-methyl-nonanoylamino}-cyclohexanecarboxylic acid methyl ester The title compound prepared in accordance with General Procedure (I).

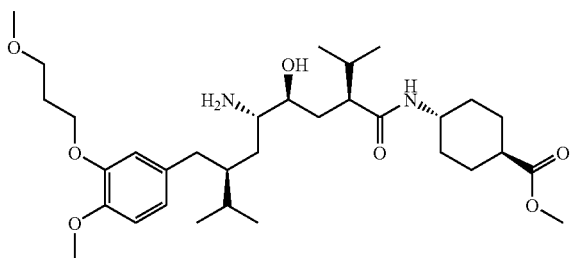

MS (LC-MS): 594.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.01 minutes.

EXAMPLE 44

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopentanecarboxylic acid The title compound prepared in accordance with General Procedure (I).

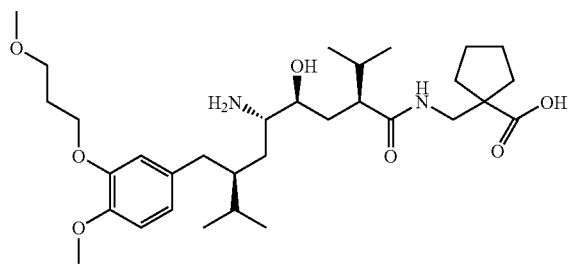

MS (LC-MS): 579.1 [M+H]$^+$; $t_R$ (HPLC, C8 column, 20-95% CH$_3$CN/H$_2$O/3.5 minutes, 95% CH$_3$CN/1 minutes, flow: 0.8 mL/min.): 2.48 minutes.

EXAMPLE 45

(2S,4S,5S,7S)-5-Amino-4-hydroxy-2-isopropyl-7-[4-methoxy-3-(3-methoxy-propoxy)-benzyl]-8-methyl-nonanoic acid amide The title compound prepared in accordance with General Procedure (I).

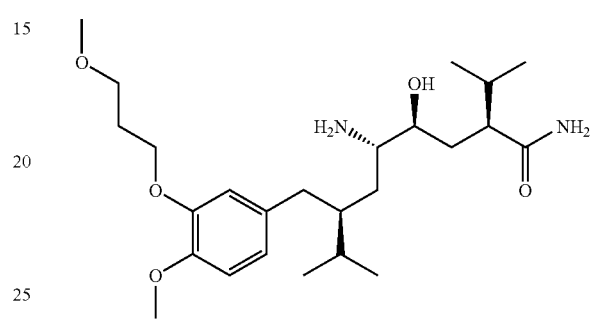

MS (LC-MS): 453.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.41 minutes.

EXAMPLE 46

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopropanecarboxylic acid amide The title compound prepared in accordance with General Procedure (I).

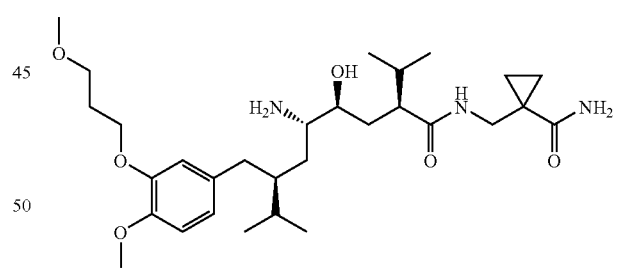

MS (LC-MS): 550.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.05 minutes.

EXAMPLE 47

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclobutanecarboxylic acid amide The title compound prepared in accordance with General Procedure (I).

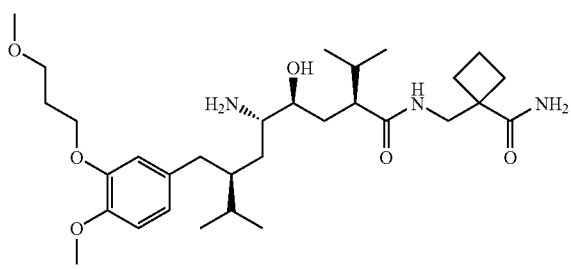

MS (LC-MS): 564.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.54 minutes.

EXAMPLE 48

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopentanecarboxylic acid amide The title compound prepared in accordance with General Procedure (I).

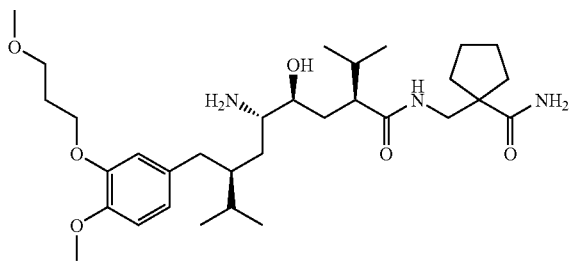

MS (LC-MS): 578.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.2 minutes.

EXAMPLE 49

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclohexanecarboxylic acid amide The title compound prepared in accordance with General Procedure (I).

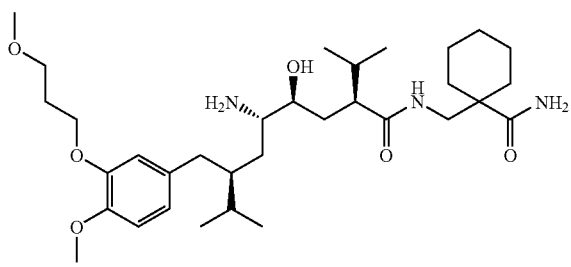

MS (LC-MS): 592.2 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.02 minutes.

EXAMPLE 50

1-{(2S,4S,5S,7S)-5-Amino-4-hydroxy-2-isopropyl-7-[4-methoxy-3-(3-methoxy-propoxy)-benzyl]-8-methyl-nonanoylamino}-cyclopentanecarboxylic acid amide The title compound prepared in accordance with General Procedure (II).

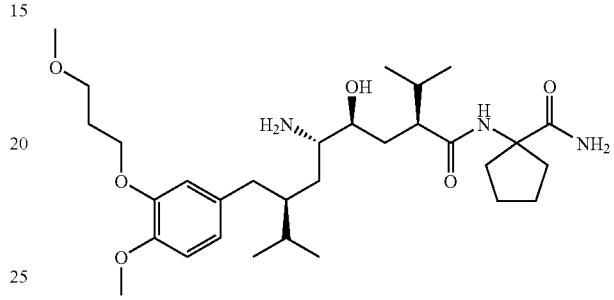

MS (LC-MS): 564.2 [M+H]$^+$; $t_R$ (HPLC, C8 column, 5-95% CH$_3$CN/H$_2$O/6.5 minutes, 95% CH$_3$CN/H$_2$O/1 minute, flow: 0.5 ml/min): 4.66 minutes.

EXAMPLE 51

2-{(2S,4S,5S,7S)-5-Amino-4-hydroxy-2-isopropyl-7-[4-methoxy-3-(3-methoxy-propoxy)-benzyl]-8-methyl-nonanoylamino}-cyclopentanecarboxylic acid amide The title compound prepared in accordance with General Procedure (I).

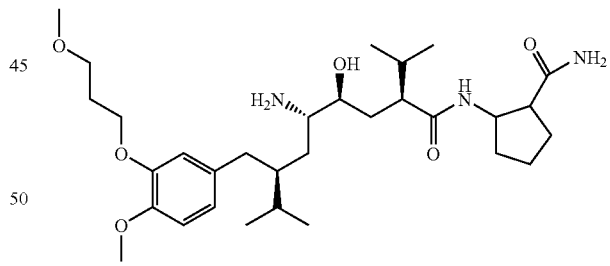

MS (LC-MS): 564.3 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.3 minutes.

EXAMPLE 52

2-{(2S,4S,5S,7S)-5-Amino-4-hydroxy-2-isopropyl-7-[4-methoxy-3-(3-methoxy-propoxy)-benzyl]-8-methyl-nonanoylamino}-cyclohexanecarboxylic acid amide The title compound prepared in accordance with General Procedure (I).

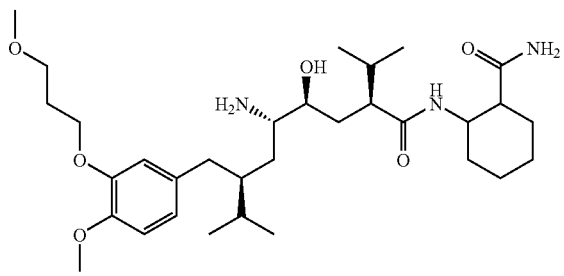

MS (LC-MS): 578.1 [M+H]⁺; $t_R$ (HPLC, C8 column, 5-95% CH₃CN/H₂O/6.5 minutes, 95% CH₃CN/H₂O/1 minute, flow: 0.5 mL/min.): 4.84 minutes.

EXAMPLE 53

1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopentanecarboxylic acid methylamide The title compound prepared in accordance with General Procedure (I).

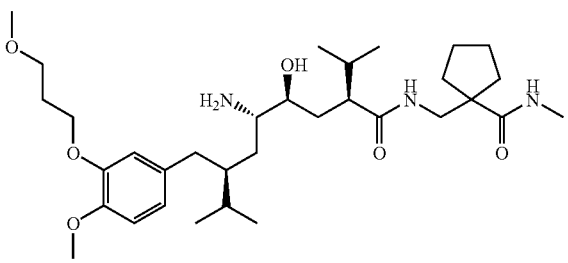

MS (LC-MS): 592.1 [M+H]⁺; $t_R$ (HPLC, C8 column, 5-95% CH₃CN/H₂O/6.5 minutes, 95% CH₃CN/H₂O/1 minute, flow: 0.5 mL/min.): 4.51 minutes.

EXAMPLE 54

(2S,4S,5S,7S)-5-Amino-4-hydroxy-2-isopropyl-7-[4-methoxy-3-(3-methoxy-propoxy)-benzyl]-8-methyl-nonanoic acid (1-formylamino-cyclopropylmethyl)-amide The title compound prepared in accordance with General Procedure (II).

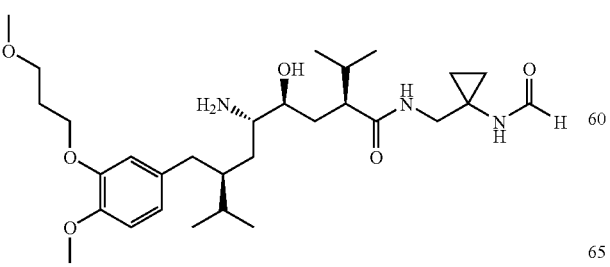

MS (LC-MS): 551 [M+H]⁺; $t_R$ (HPLC, C8 column, 5-95% CH₃CN/H₂O/6.5 minutes, 95% CH₃CN/H₂O/1 minute, flow: 0.5 mL/min.): 4.41 minutes.

EXAMPLE 55

(2S,4S,5S,7S)-5-Amino-4-hydroxy-2-isopropyl-7-[(4-methoxy-3-(3-methoxy-propoxy)-benzyl]-8-methyl-nonanoic acid (1-acetylamino-cyclopropylmethyl)-amide The title compound prepared in accordance with General Procedure (II).

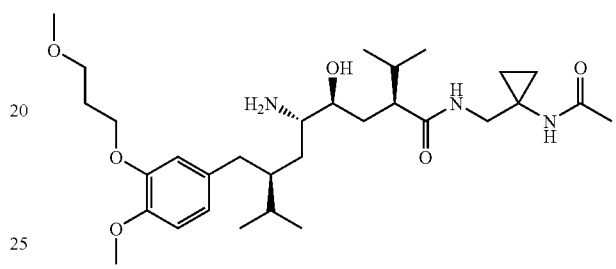

MS (LC-MS): 565.1 [M+H]⁺; $t_R$ (HPLC, C8 column, 5-95% CH₃CN/H₂O/6.5 minutes, 95% CH₃CN/H₂O/1 minute, flow: 0.5 mL/min.): 4.46 minutes.

EXAMPLE 56

(2S,4S,5S,7S)-5-Amino-4-hydroxy-2-isopropyl-7-[4-methoxy-3-(3-methoxy-propoxy)-benzyl]-8-methyl-nonanoic acid (1-formylamino-cyclopentylmethyl)-amide The title compound prepared in accordance with General Procedure (II).

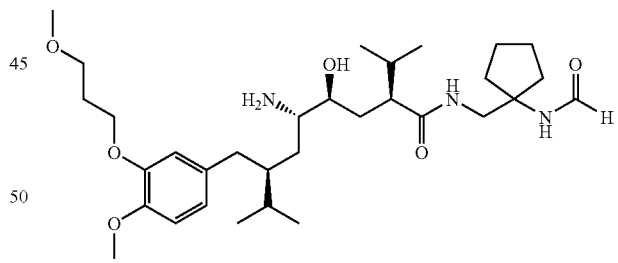

MS (LC-MS): 579.1 [M+H]⁺; $t_R$ (HPLC, C8 column, 5-95% CH₃CN/H₂O/6.5 minutes, 95% CH₃CN/H₂O/1 minute, flow: 0.5 mL/min.): 4.7 minutes.

EXAMPLE 57

(2S,4S,5S,7S)-5-Amino-4-hydroxy-2-isopropyl-7-[4-methoxy-3-(3-methoxy-propoxy)-benzyl]-8-methyl-nonanoic acid (1-formylamino-cyclopentylmethyl)-amide The title compound prepared in accordance with General Procedure (II).

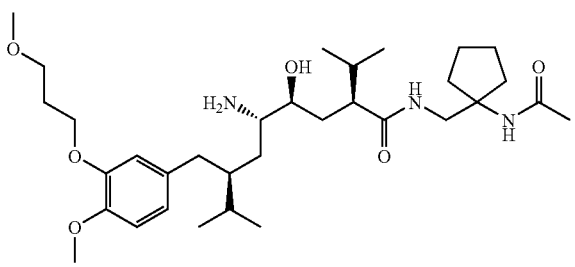

MS (LC-MS): 592.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.68 minutes.

EXAMPLE 58

(2S,4S,5S,7S)-5-Amino-4-hydroxy-2-isopropyl-7-[4-methoxy-3-(3-methoxy-propoxy)-benzyl]-8-methyl-nonanoic acid [1-(2,2-dimethyl-propionylamino)-cyclopentylmethyl]-amide The title compound prepared in accordance with General Procedure (II).

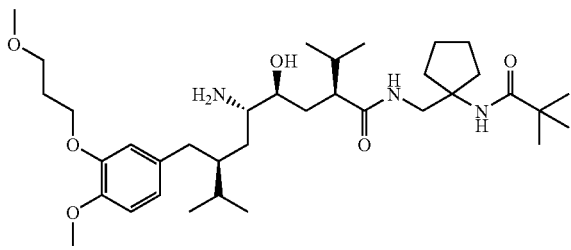

MS (LC-MS): 634.2 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.18 minutes.

EXAMPLE 59

(2S,4S,5S,7S)-5-Amino-4-hydroxy-2-isopropyl-7-[4-methoxy-3-(3-methoxy-propoxy)-benzyl]-8-methyl-nonanoic acid {1-[(2,2-dimethyl-propionylamino)-methyl]-cyclopentyl}-amide The title compound prepared in accordance with General Procedure (II).

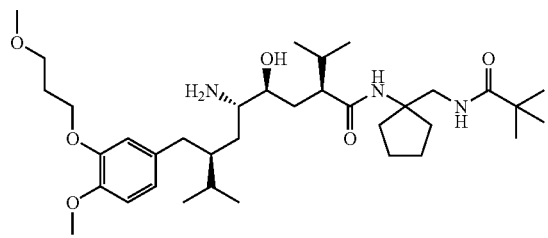

MS (LC-MS): 635.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.34 minutes.

EXAMPLE 60

Cyclopropanecarboxylic acid [1-({(2S,4S,5S,7S)-5-amino-4-hydroxy-2-isopropyl-7-[4-methoxy-3-(3-methoxy-propoxy)-benzyl]-8-methyl-nonanoylamino}-methyl)-cyclopentyl]-amide The title compound prepared in accordance with General Procedure (II).

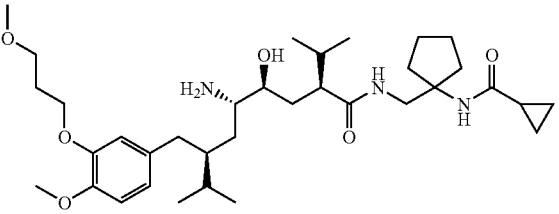

MS (LC-MS): [M+H]$^+$; $R_f$ [CH$_2$Cl$_2$:MeOH (9:1)]: 0.18 minutes.

EXAMPLE 61

[1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopropyl]-carbamic acid tert-butyl ester The title compound prepared in accordance with General Procedure (II).

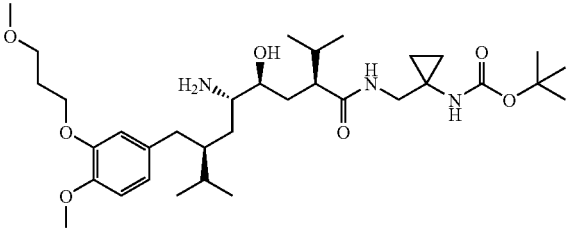

MS (LC-MS): 623.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.22 minutes.

EXAMPLE 62

[1-({(2S,4S,5S,7S)-5-Amino-4-hydroxy-2-isopropyl-7-[4-methoxy-3-(3-methoxy-propoxy)-benzyl]-8-methyl-nonanoylamino}-methyl)-cyclopentyl]-carbamic acid tert-butyl ester The title compound prepared in accordance with General Procedure (II).

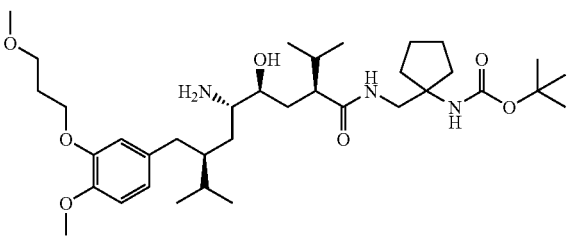

MS (LC-MS): 650.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.43 minutes.

EXAMPLE 63

(2S,4S,5S,7S)-5-Amino-4-hydroxy-2-isopropyl-7-[4-methoxy-3-(3-methoxy-propoxy)-benzyl]-8-methyl-nonanoic acid (1-amino-cyclopropylmethyl)-amide The title compound prepared in accordance with General Procedure (II).

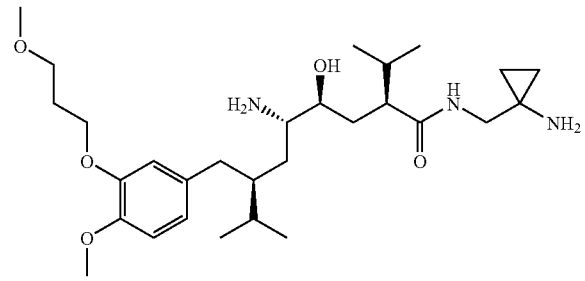

MS (LC-MS): 523.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.33 minutes.

EXAMPLE 64

(2S,4S,5S,7S)-5-Amino-4-hydroxy-2-isopropyl-7-[4-methoxy-3-(3-methoxy-propoxy)-benzyl]-8-methyl-nonanoic acid (1-amino-cyclopentylmethyl)-amide The title compound prepared in accordance with General Procedure (I).

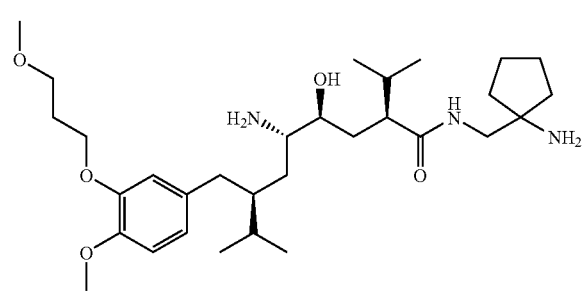

MS (LC-MS): 550.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.31 minutes.

EXAMPLE 65

(2S,4S,5S,7S)-5-Amino-4-hydroxy-2-isopropyl-7-[4-methoxy-3-(3-methoxy-propoxy)-benzyl]-8-methyl-nonanoic acid (4-amino-cyclohexyl)-amide The title compound prepared in accordance with General Procedure (I).

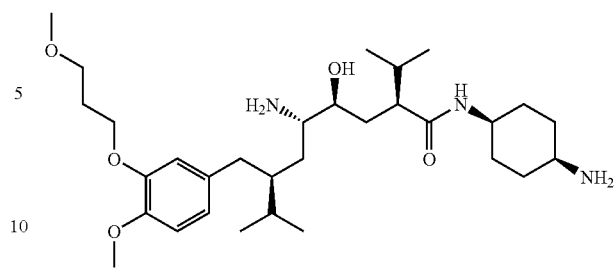

MS (LC-MS): 550.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.18 minutes.

EXAMPLE 66

(2S,4S,5S,7S)-5-Amino-4-hydroxy-2-isopropyl-7-[4-methoxy-3-(3-methoxy-propoxy)-benzyl]-8-methyl-nonanoic acid (4-amino-cyclohexyl)-amide The title compound prepared in accordance with General Procedure (I).

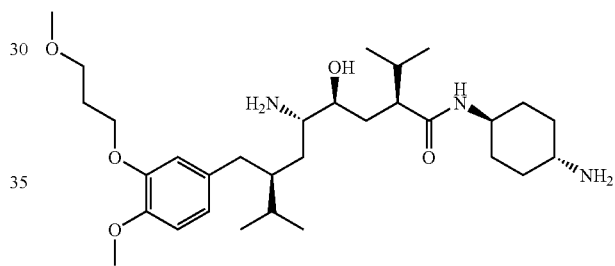

MS (LC-MS): 550.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.14 minutes.

EXAMPLE 67

(2S,4S,5S,7S)-5-Amino-4-hydroxy-2-isopropyl-7-[4-methoxy-3-(3-methoxy-propoxy)-benzyl]-8-methyl-nonanoic acid (1-dimethylamino-cyclopropylmethyl)-amide The title compound prepared in accordance with General Procedure (II).

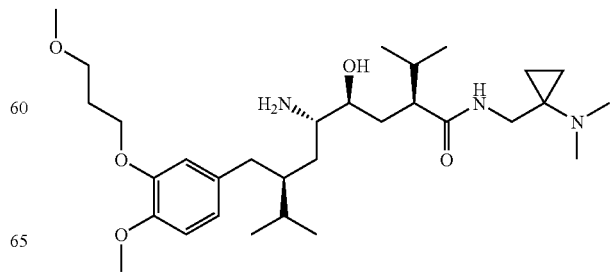

MS (LC-MS): 551.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.36 minutes.

EXAMPLE 68

(2S,4S,5S,7S)-5-Amino-4-hydroxy-2-isopropyl-7-[4-methoxy-3-(3-methoxy-propoxy)-benzyl]-8-methyl-nonanoic acid (1-dimethylamino-cyclopentylmethyl)-amide The title compound prepared in accordance with General Procedure (II).

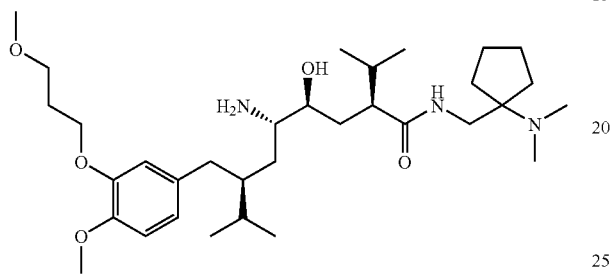

MS (LC-MS): 578.2 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.29 minutes.

EXAMPLE 69

(2S,4S,6S,7S)-6-Amino-4-hydroxy-2-isopropyl-7-[4-methoxy-3-(3-methoxy-propoxy)-benzyl]-8-methyl-nonanoic acid (1-methoxymethyl-cyclopentyl)-amide The title compound prepared in accordance with General Procedure (II).

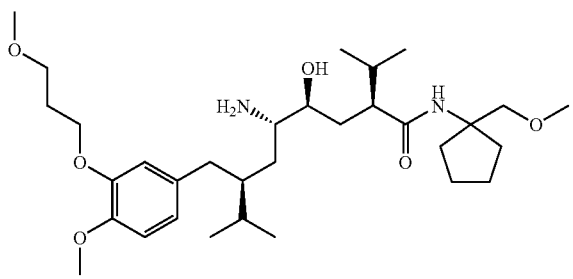

MS (LC-MS): 565.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.11 minutes.

EXAMPLE 70

(2S,4S,5S,7S)-5-Amino-4-hydroxy-2-isopropyl-7-[4-methoxy-3-(3-methoxy-propoxy)-benzyl]-8-methyl-nonanoic acid (1-methoxy-cyclopentylmethyl)-amide The title compound prepared in accordance with General Procedure (II).

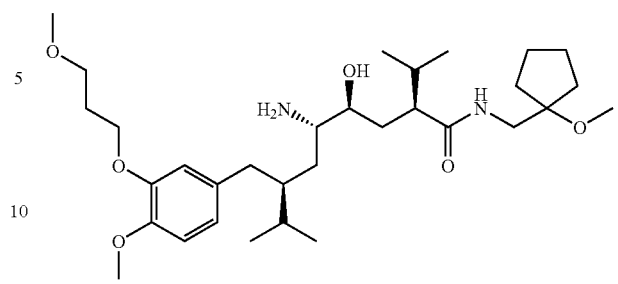

MS (LC-MS): 566 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 5.01 minutes.

EXAMPLE 71

(2S,4S,5S,7S)-5-Amino-4-hydroxy-2-isopropyl-7-[4-methoxy-3-(3-methoxy-propoxy)-benzyl]-8-methyl-nonanoic acid ((1S,2S)-2-benzyloxy-cyclopentyl)-amide The title compound prepared in accordance with General Procedure (I).

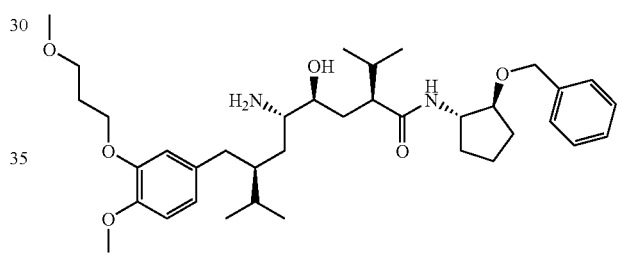

MS (LC-MS): 628.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.38 minutes.

EXAMPLE 72

(2S,4S,5S,7S)-5-Amino-4-hydroxy-2-isopropyl-7-[4-methoxy-3-(3-methoxy-propoxy)-benzyl]-8-methyl-nonanoic acid ((1R,2R)-2-benzyloxy-cyclopentyl)-amide The title compound prepared in accordance with General Procedure (I).

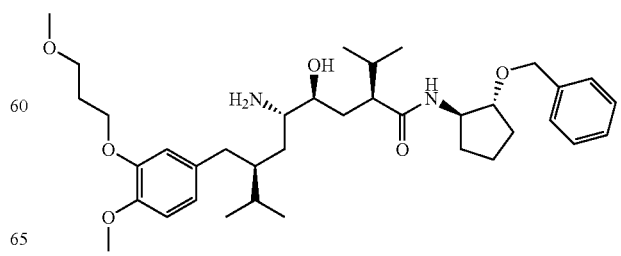

MS (LC-MS): 628.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.42 minutes.

EXAMPLE 73

(2S,4S,5S,7S)-5-Amino-4-hydroxy-2-isopropyl-7-[4-methoxy-3-(3-methoxy-propoxy)-benzyl]-8-methyl-nonanoic acid (4-methoxy-cyclohexyl)-amide The title compound prepared in accordance with General Procedure (II).

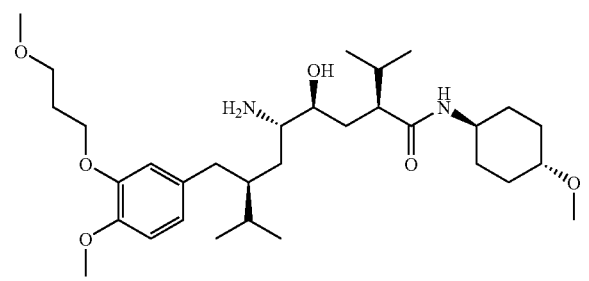

MS (LC-MS): 565.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.59 minutes.

EXAMPLE 74

(2S,4S,5S,7S)-5-Amino-4-hydroxy-2-isopropyl-7-[4-methoxy-3-(3-methoxy-propoxy)-benzyl]-8-methyl-nonanoic acid (4-methoxy-cyclohexyl)-amide

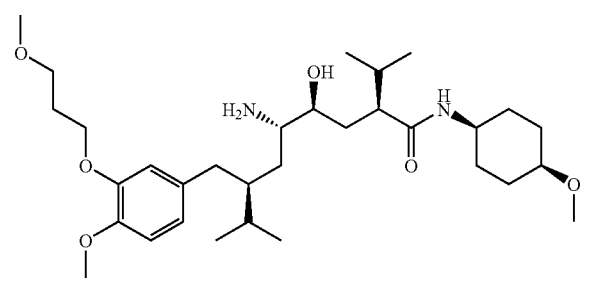

The title compound prepared in accordance with General Procedure (II).
MS (LC-MS): 565.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.67 minutes.

EXAMPLE 75

(2S,4S,5S,7S)-5-Amino-4-hydroxy-2-isopropyl-7-[4-methoxy-3-(3-methoxy-propoxy)-benzyl]-8-methyl-nonanoic acid ((1S,2S)-2-benzyloxy-cyclohexyl)-amide The title compound prepared in accordance with General Procedure (I).

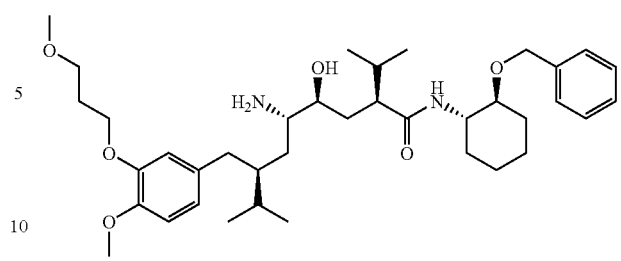

MS (LC-MS): 641.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 6.10 minutes.

EXAMPLE 76

(2S,4S,5S,7S)-5-Amino-4-hydroxy-2-isopropyl-7-[4-methoxy-3-(3-methoxy-propoxy)-benzyl]-8-methyl-nonanoic acid ((1R,2R)-2-benzyloxy-cyclohexyl)-amide The title compound prepared in accordance with General Procedure (I).

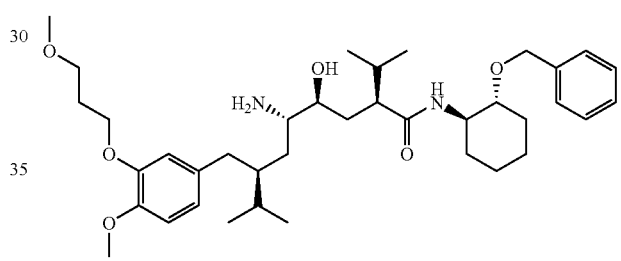

MS (LC-MS): 641.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 6.00 minutes.

EXAMPLE 77

(2S,4S,5S,7S)-5-Amino-4-hydroxy-2-isopropyl-7-[4-methoxy-3-(3-methoxy-propoxy)-benzyl]-8-methyl-nonanoic acid (1-hydroxy-cyclopropylmethyl)-amide The title compound prepared in accordance with General Procedure (II).

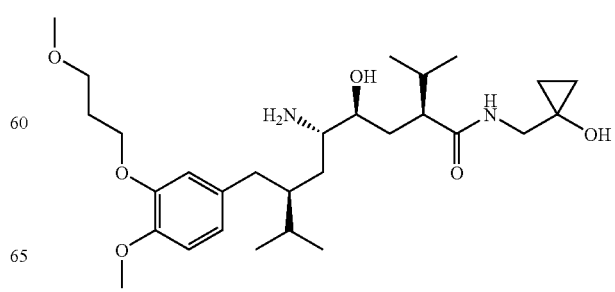

MS (LC-MS): 523.1 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.52 minutes.

EXAMPLE 78

(2S,4S,5S,7S)-5-Amino-4-hydroxy-2-isopropyl-7-[4-methoxy-3-(3-methoxy-propoxy)-benzyl]-8-methyl-nonanoic acid ((1R,2R)-2-hydroxy-cyclopentyl)-amide The title compound prepared in accordance with General Procedure (I).

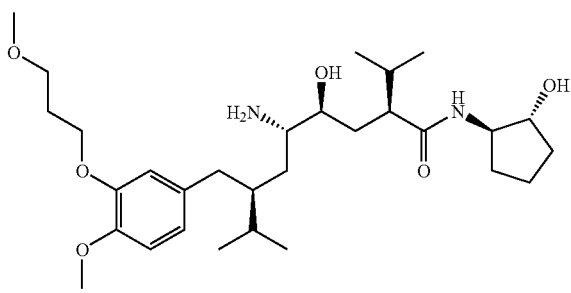

MS (LC-MS): 538.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.74 minutes.

EXAMPLE 79

(2S,4S,5S,7S)-5-Amino-4-hydroxy-2-isopropyl-7-[4-methoxy-3-(3-methoxy-propoxy)-benzyl]-8-methyl-nonanoic acid ((1S,2S)-2-hydroxy-cyclopentyl)-amide The title compound prepared in accordance with General Procedure (I).

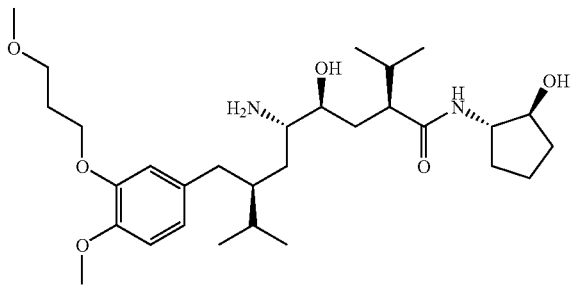

MS (LC-MS): 537.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.37 minutes.

EXAMPLE 80

(2S,4S,5S,7S)-5-Amino-4-hydroxy-2-isopropyl-7-[4-methoxy-3-(3-methoxy-propoxy)-benzyl]-8-methyl-nonanoic acid (1-hydroxymethyl-cyclopentyl)-amide The title compound prepared in accordance with General Procedure (II).

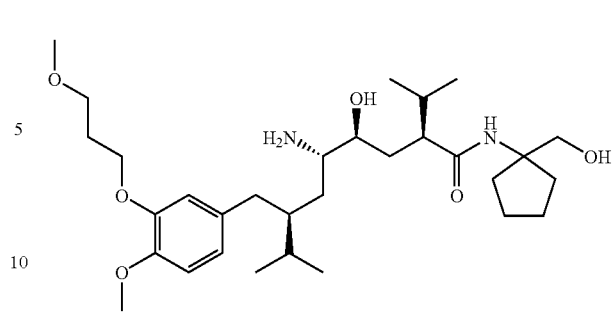

MS (LC-MS): 551.1 [M+H]$^{30}$ ; $t_R$ (HPLC, C8 column, 5-95% CH$_3$CN/H$_2$O/6.5 minutes, 95% CH$_3$CN/H$_2$O/1 minute, flow: 0.5 mL/min.): 4.77 minutes.

EXAMPLE 81

(2S,4S,5S,7S)-5-Amino-4-hydroxy-2-isopropyl-7-[4-methoxy-3-(3-methoxy-propoxy)-benzyl]-8-methyl-nonanoic acid (1-hydroxy-cyclopentylmethyl)-amide The title compound prepared in accordance with General Procedure (II).

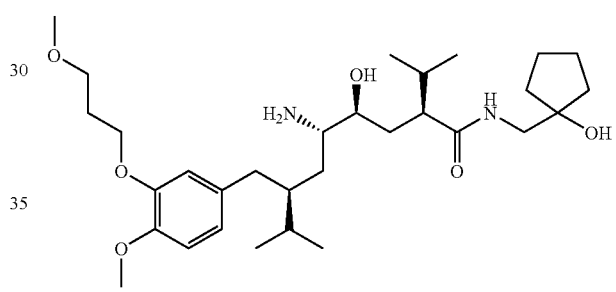

MS (LC-MS): 552 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.72 minutes.

EXAMPLE 82

(2S,4S,5S,7S)-5-Amino-4-hydroxy-2-isopropyl-7-[4-methoxy-3-(3-methoxy-propoxy)-benzyl]-8-methyl-nonanoic acid ((1R,2R)-2-hydroxy-cyclohexyl)-amide The title compound prepared in accordance with General Procedure (I).

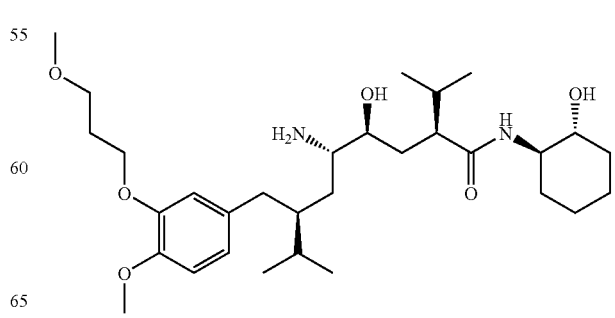

MS (LC-MS): 551.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 4.62 minutes.

EXAMPLE 83

(2S,4S,5S,7S)-5-Amino-4-hydroxy-2-isopropyl-7-[4-methoxy-3-(3-methoxy-propoxy)-benzyl]-8-methyl-nonanoic acid ((1S,2S)-2-hydroxy-cyclohexyl)-amide The title compound prepared in accordance with General Procedure (I).

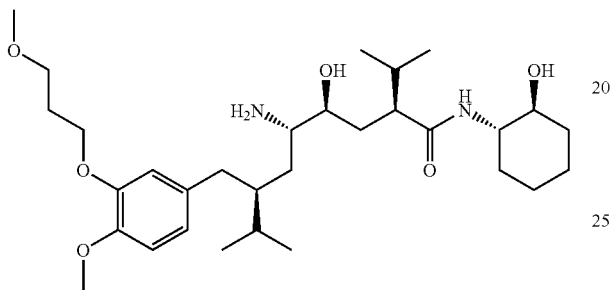

MS (LC-MS): 551.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 4.41 minutes.

EXAMPLE 84

(2S,4S,5S,7S)-5-Amino-4-hydroxy-2-isopropyl-7-[4-methoxy-3-(3-methoxy-propoxy)-benzyl]-8-methyl-nonanoic acid (4-hydroxy-cyclohexyl)-amide The title compound prepared in accordance with General Procedure (I).

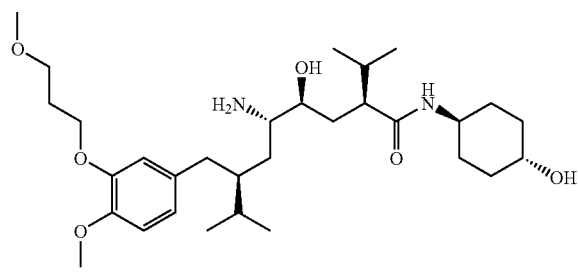

MS (LC-MS): 551.3 [M]⁺; $R_f$[CH₂Cl₂:MeOH (9:1)]: 0.61 minutes.

EXAMPLE 85

(2S,4S,5S,7S)-5-Amino-4-hydroxy-2-isopropyl-7-[4-methoxy-3-(3-methoxy-propoxy)-benzyl]-8-methyl-nonanoic acid (4-hydroxy-cyclohexyl)-amide The title compound prepared in accordance with General Procedure (I).

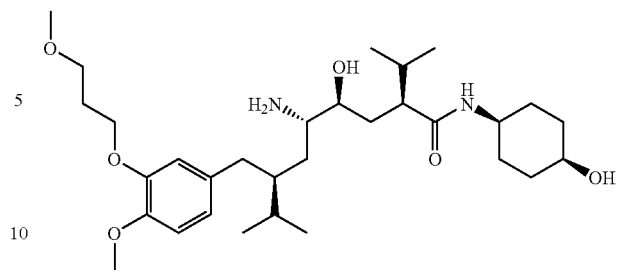

MS (LC-MS): 552.0 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.81 minutes.

EXAMPLE 86

(2S,4S,5S,7S)-5-Amino-4-hydroxy-2-isopropyl-7-[4-methoxy-3-(3-methoxy-propoxy)-benzyl]-8-methyl-nonanoic acid (1-hydroxy-cyclohexylmethyl)-amide The title compound prepared in accordance with General Procedure (III).

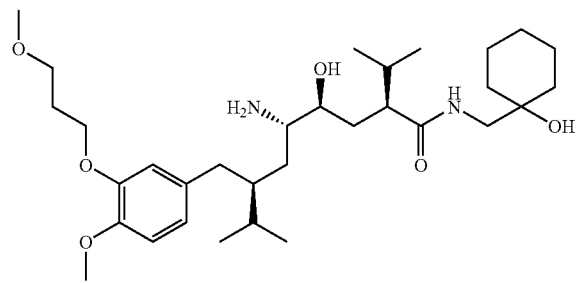

MS (LC-MS): 565.2 [M+H]⁺; $t_R$ (HPLC, C8 column, 5-95% CH₃CN/H₂O/6.5 minutes, 95% CH₃CN/H₂O/1 minute, flow: 0.5 mL/min.): 5.07 minutes.

EXAMPLE 87

(2S,4S,5S,7S)-5-Amino-4-hydroxy-2-isopropyl-7-[4-methoxy-3-(3-methoxy-propoxy)-benzyl]-8-methyl-nonanoic acid ((R)-1-phenyl-ethyl)-amide The title compound prepared in accordance with General Procedure (I).

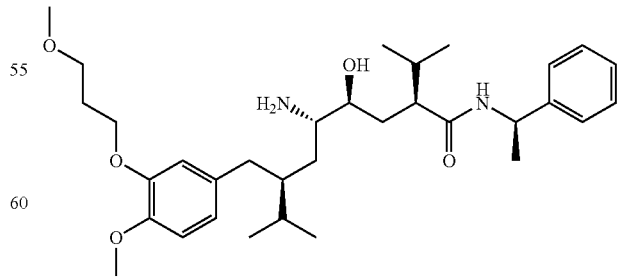

MS (LC-MS): 558.3 [M+H]⁺; $t_R$ (HPLC, C8 column, 5-95% CH₃CN/H₂O/6.5 minutes, 95% CH₃CN/H₂O/1 minute, flow: 0.5 mL/min.): 4.63 minutes.

EXAMPLE 88

(2S,4S,5S,7S)-5-Amino-4-hydroxy-2-isopropyl-7-[4-methoxy-3-(3-methoxy-propoxy)-benzyl]-8-methyl-nonanoic acid ((S)-1-phenyl-ethyl)-amide The title compound prepared in accordance with General Procedure (I).

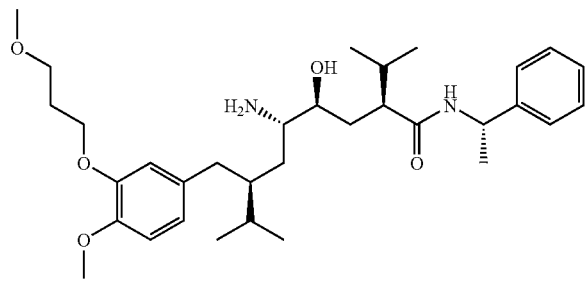

MS (LC-MS): 558.3 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.69 minutes.

EXAMPLE 89

(2S,4S,5S,7S)-5-Amino-4-hydroxy-2-isopropyl-7-[4-methoxy-3-(3-methoxy-propoxy)-benzyl]-8-methyl-nonanoic acid (1-methyl-1-phenyl-ethyl)-amide The title compound prepared in accordance with General Procedure (I).

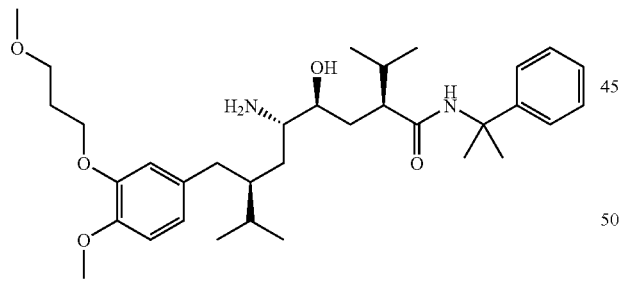

MS (LC-MS): 572.0 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 3.85 minutes.

EXAMPLE 90

(2S,4S,5S,7S)-5-Amino-4-hydroxy-2-isopropyl-7-[4-methoxy-3-(3-methoxy-propoxy)-benzyl]-8-methyl-nonanoic acid (naphthalen-1-ylmethyl)-amide The title compound prepared in accordance with General Procedure (I).

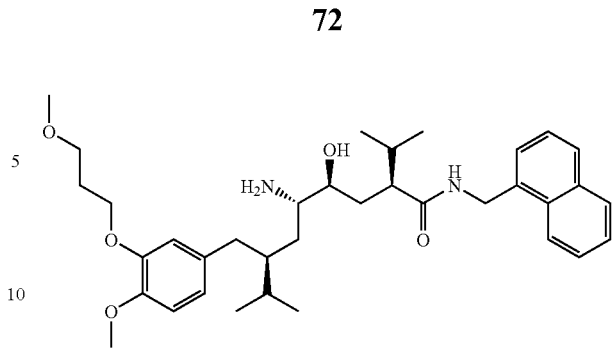

MS (LC-MS): 594.5 [M+H]$^+$; $R_f$ [CH$_2$Cl$_2$:MeOH (9:1)]: 0.21 minutes.

EXAMPLE 91

(2S,4S,5S,7S)-5-Amino-4-hydroxy-2-isopropyl-7-[4-methoxy-3-(3-methoxy-propoxy)-benzyl]-8-methyl-nonanoic acid indan-2-ylamide The title compound prepared in accordance with General Procedure (I).

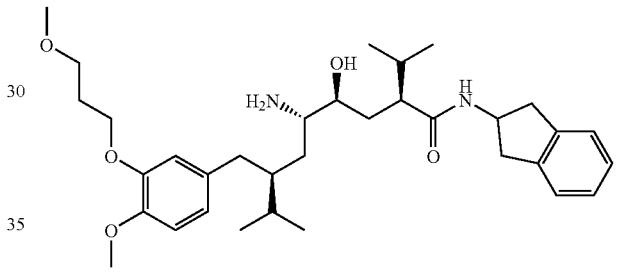

MS (LC-MS): 569.1 [M]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.16 minutes.

EXAMPLE 92

(2S,4S,5S,7S)-5-Amino-4-hydroxy-2-isopropyl-7-[4-methoxy-3-(3-methoxy-propoxy)-benzyl]-8-methyl-nonanoic acid 2-methyl-benzylamide The title compound prepared in accordance with General Procedure (I).

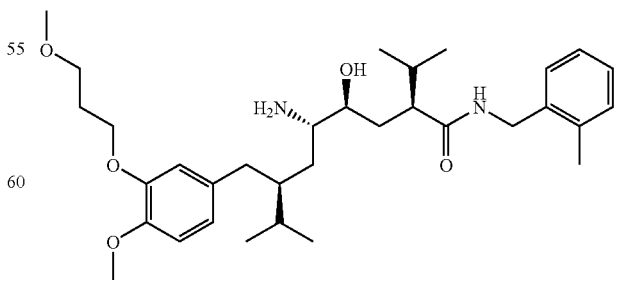

MS (LC-MS): 558.3 [M+H]$^+$; $R_f$ [CH$_2$Cl$_2$:MeOH (9:1)]: 0.17 minutes.

EXAMPLE 93

(2S,4S,5S,7S)-5-Amino-4-hydroxy-2-isopropyl-7-[4-methoxy-3-(3-methoxy-propoxy)-benzyl]-8-methyl-nonanoic acid 3-methyl-benzylamide The title compound prepared in accordance with General Procedure (I).

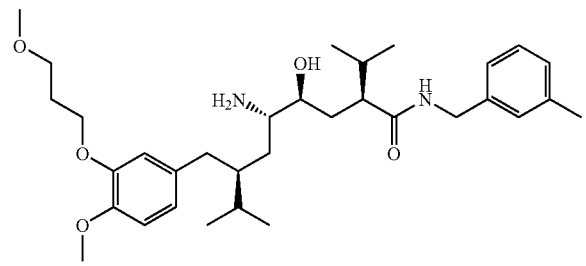

MS (LC-MS): 558.3 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.28 minutes.

EXAMPLE 94

(2S,4S,5S,7S))-5-Amino-4-hydroxy-2-isopropyl-7-[4-methoxy-3-(3-methoxy-propoxy)-benzyl]-8-methyl-nonanoic acid 4-methyl-benzylamide The title compound prepared in accordance with General Procedure (I).

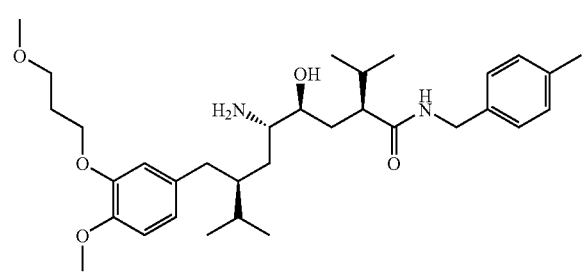

MS (LC-MS): 558.3 [M+H]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 3.76 minutes.

EXAMPLE 95

(2S,4S,5S,7S)-5-Amino-4-hydroxy-2-isopropyl-7-[4-methoxy-3-(3-methoxy-propoxy)-benzyl]-8-methyl-nonanoic acid ((R)-1-p-tolyl-ethyl)-amide The title compound prepared in accordance with General Procedure (I).

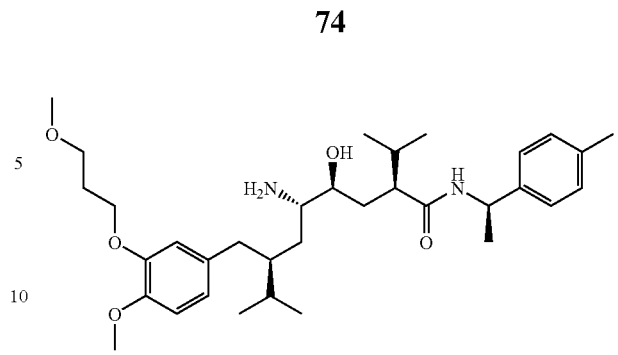

MS (LC-MS): 571.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.24 minutes.

EXAMPLE 96

(2S,4S,5S,7S))-5-Amino-4-hydroxy-2-isopropyl-7-[4-methoxy-3-(3-methoxy-propoxy)-benzyl]-8-methyl-nonanoic acid ((S)-1-p-tolyl-ethyl)-amide The title compound prepared in accordance with General Procedure (I).

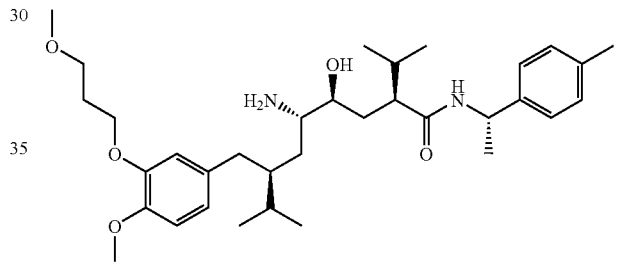

MS (LC-MS): 571.2 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.25 minutes.

EXAMPLE 97

(2S,4S,5S,7S))-5-Amino-4-hydroxy-2-isopropyl-7-[4-methoxy-3-(3-methoxy-propoxy)-benzyl]-8-methyl-nonanoic acid 4-isopropyl-benzylamide The title compound prepared in accordance with General Procedure (I).

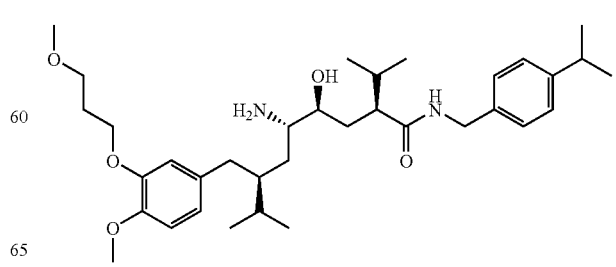

MS (LC-MS): 586.3 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 4.26 minutes.

EXAMPLE 98

(2S,4S,5S,7S)-5-Amino-4-hydroxy-2-isopropyl-7-[4-methoxy-3-(3-methoxy-propoxy)-benzyl]-8-methyl-nonanoic acid 2-methoxy-benzylamide The title compound prepared in accordance with General Procedure (I).

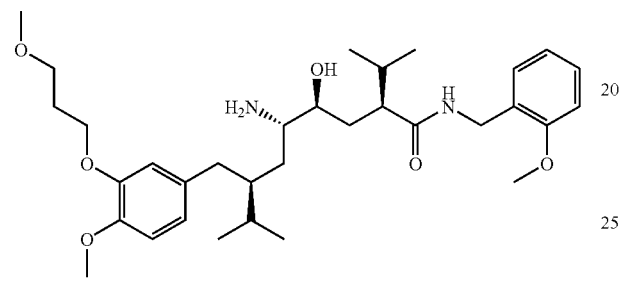

MS (LC-MS): 573.3 [M]⁺; $R_f$[CH₂Cl₂:MeOH (9:1)]: 0.15 minutes.

EXAMPLE 99

(2S,4S,5S,7S))-5-Amino-4-hydroxy-2-isopropyl-7-[4-methoxy-3-(3-methoxy-propoxy)-benzyl]-8-methyl-nonanoic acid 3-methoxy-benzylamide The title compound prepared in accordance with General Procedure (I).

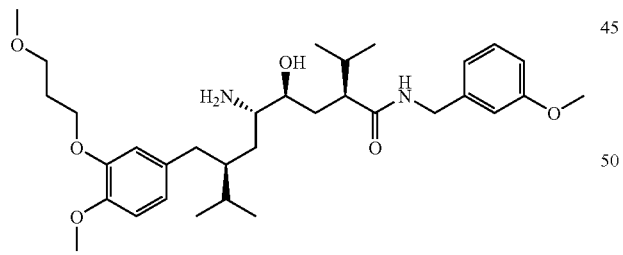

MS (LC-MS): 573.3 [M]⁺; $R_f$[CH₂Cl₂:MeOH (9:1)]: 0.17 minutes.

EXAMPLE 100

(2S,4S,5S,7S)-5-Amino-4-hydroxy-2-isopropyl-7-[4-methoxy-3-(3-methoxy-propoxy)-benzyl]-8-methyl-nonanoic acid 4-methoxy-benzylamide The title compound prepared in accordance with General Procedure (I).

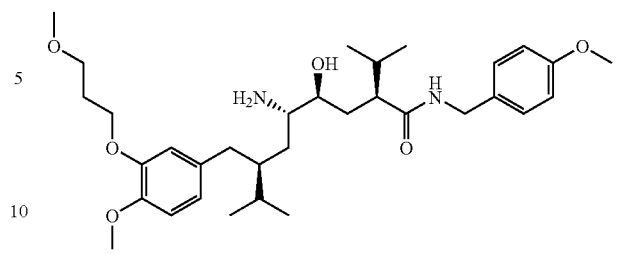

MS (LC-MS): 573.3 [M]⁺; $R_f$[CH₂Cl₂:MeOH (9:1)]: 0.14 minutes.

EXAMPLE 101

(2S,4S,5S,7S)-5-Amino-4-hydroxy-2-isopropyl-7-[4-methoxy-3-(3-methoxy-propoxy)-benzyl]-8-methyl-nonanoic acid [(S)-1-(3-methoxy-phenyl)-ethyl]-amide The title compound prepared in accordance with General Procedure (I).

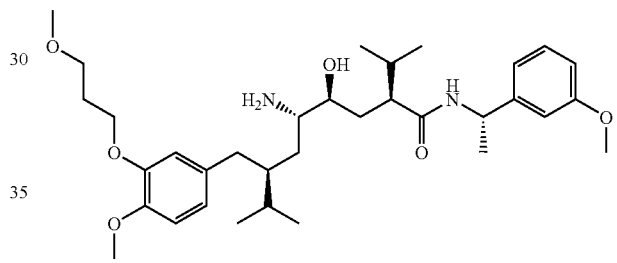

MS (LC-MS): 587.2 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.: 5.10 minutes.

EXAMPLE 102

(2S,4S,5S,7S)-5-Amino-4-hydroxy-2-isopropyl-7-[4-methoxy-3-(3-methoxy-propoxy)-benzyl]-8-methyl-nonanoic acid [(R)-1-(3-methoxy-phenyl)-ethyl]-amide The title compound prepared in accordance with General Procedure (I).

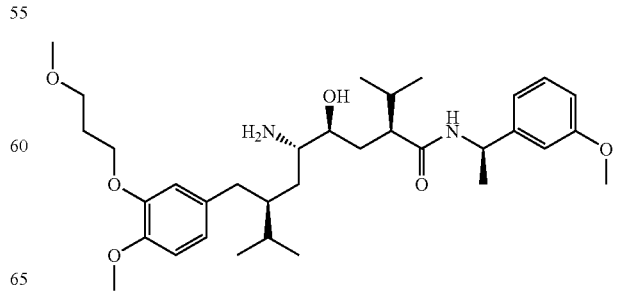

MS (LC-MS): 587.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.10 minutes.

EXAMPLE 103

(2S,4S,5S,7S)-5-Amino-4-hydroxy-2-isopropyl-7-[4-methoxy-3-(3-methoxy-propoxy)-benzyl]-8-methyl-nonanoic acid [(S)-1-(4-methoxy-phenyl)-ethyl]-amide The title compound prepared in accordance with General Procedure (I).

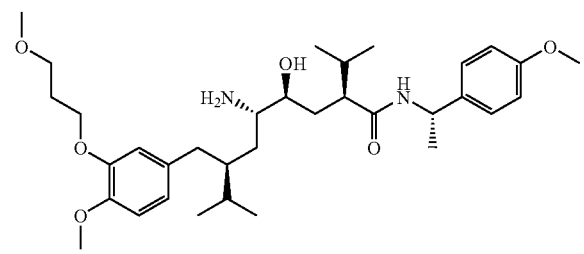

MS (LC-MS): 587.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.07 minutes.

EXAMPLE 104

(2S,4S,5S,7S)-5-Amino-4-hydroxy-2-isopropyl-7-[4-methoxy-3-(3-methoxy-propoxy)-benzyl]-8-methyl-nonanoic acid [(R)-1-(4-methoxy-phenyl)-ethyl]-amide The title compound prepared in accordance with General Procedure (I).

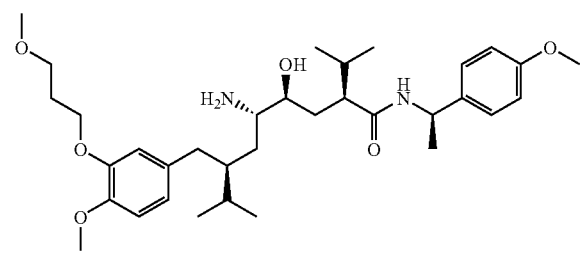

MS (LC-MS): 587.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.09 minutes.

EXAMPLE 105

(2S,4S,5S,7S)-5-Amino-4-hydroxy-2-isopropyl-7-[4-methoxy-3-(3-methoxy-propoxy)-benzyl]-8-methyl-nonanoic acid 2-methylsulfanyl-benzylamide The title compound prepared in accordance with General Procedure (I).

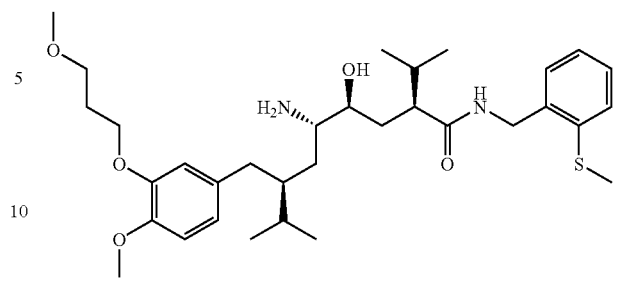

MS (LC-MS): 589.3 [M]⁺; $R_f$[CH₂Cl₂:MeOH (9:1)]: 0.10 minutes.

EXAMPLE 106

(2S,4S,5S,7S)-5-Amino-4-hydroxy-2-isopropyl-7-[4-methoxy-3-(3-methoxy-propoxy)-benzyl]-8-methyl-nonanoic acid 4-methylsulfanyl-benzylamide The title compound prepared in accordance with General Procedure (I).

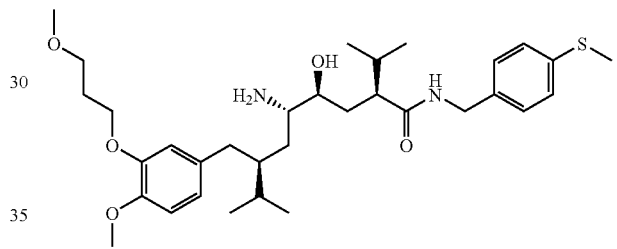

MS (LC-MS): 589.0 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.12 minutes.

EXAMPLE 107

(2S,4S,5S,7S)-5-Amino-4-hydroxy-2-isopropyl-7-[4-methoxy-3-(3-methoxy-propoxy)-benzyl]-8-methyl-nonanoic acid 2,5-dimethoxy-benzylamide The title compound prepared in accordance with General Procedure (I).

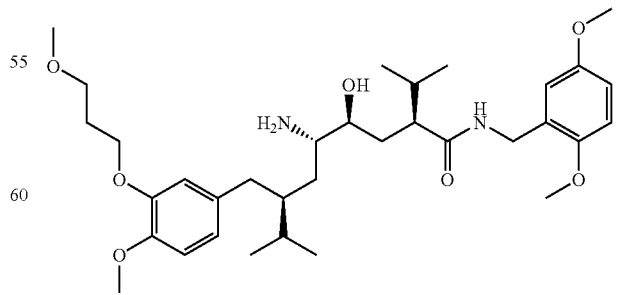

MS (LC-MS): 603.3 [M]⁺; $R_f$[CH₂Cl₂:MeOH (9:1)]: 0.13 minutes.

EXAMPLE 108

(2S,4S,5S,7S)-5-Amino-4-hydroxy-2-isopropyl-7-[4-methoxy-3-(3-methoxy-propoxy)-benzyl]-8-methyl-nonanoic acid 2,3-dimethoxy-benzylamide The title compound prepared in accordance with General Procedure (I).

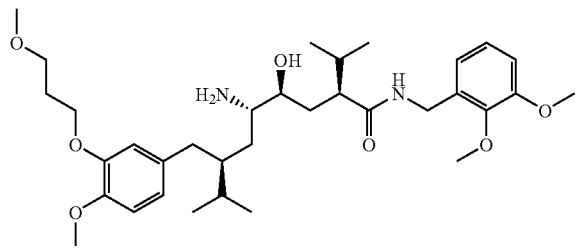

MS (LC-MS): 603.3 [M]$^+$; $t_R$ (HPLC, C18 column, 10-100% $CH_3CN/H_2O$/5 minutes, 100% $CH_3CN$/3 minutes, 100-10% $CH_3CN/H_2O$/3 minutes, flow: 1.5 mL/min.): 5.03 minutes.

EXAMPLE 109

(2S,4S,5S,7S)-5-Amino-4-hydroxy-2-isopropyl-7-[4-methoxy-3-(3-methoxy-propoxy)-benzyl]-8-methyl-nonanoic acid 2,4-dimethoxy-benzylamide The title compound prepared in accordance with General Procedure (I).

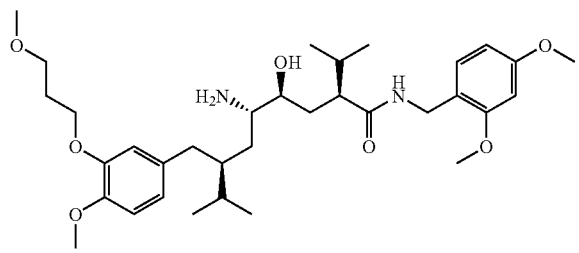

MS (LC-MS): 603.3 [M]$^+$; $R_f$[$CH_2Cl_2$:MeOH (9:1)]: 0.23 minutes.

EXAMPLE 110

(2S,4S,5S,7S)-5-Amino-4-hydroxy-2-isopropyl-7-[4-methoxy-3-(3-methoxy-propoxy)-benzyl]-8-methyl-nonanoic acid 3,4-dimethoxy-benzylamide The title compound prepared in accordance with General Procedure (I).

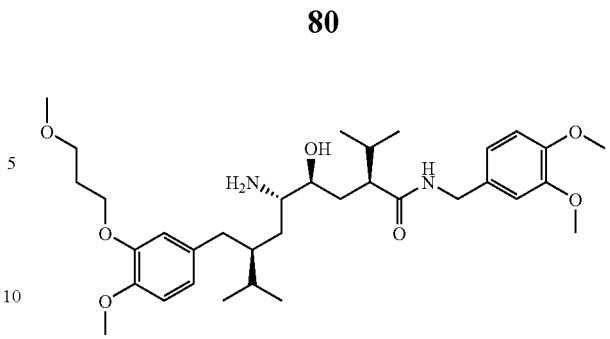

MS (LC-MS): 603.3 [M]$^+$; $R_f$[$CH_2Cl_2$:MeOH (9:1)]: 0.18 minutes.

EXAMPLE 111

(2S,4S,5S,7S)-5-Amino-4-hydroxy-2-isopropyl-7-[4-methoxy-3-(3-methoxy-propoxy)-benzyl]-8-methyl-nonanoic acid 2,6-dimethoxy-benzylamide The title compound prepared in accordance with General Procedure (I).

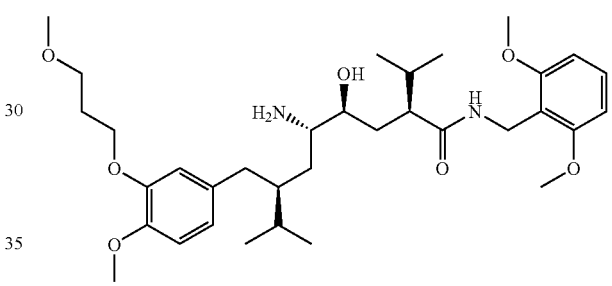

MS (LC-MS): 603.3 [M]$^+$; $R_f$[$CH_2Cl_2$:MeOH (9:1)]: 0.24 minutes.

EXAMPLE 112

(2S,4S,5S,7S)-5-Amino-4-hydroxy-2-isopropyl-7-[4-methoxy-3-(3-methoxy-propoxy)-benzyl]-8-methyl-nonanoic acid 3,5-dimethoxy-benzylamide The title compound prepared in accordance with General Procedure (I).

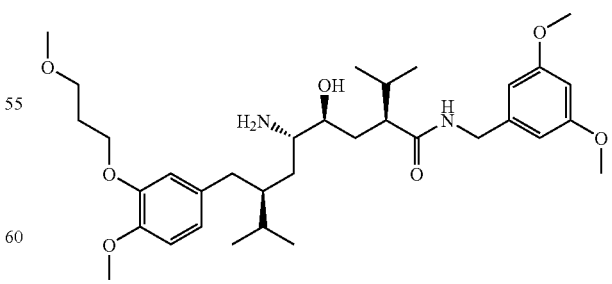

MS (LC-MS): 603.3 [M]$^+$; $t_R$ (HPLC, C18 column, 10-100% $CH_3CN/H_2O$/5 minutes, 100% $CH_3CN$/3 minutes, 100-10% $CH_3CN/H_2O$/3 minutes, flow: 1.5 mL/min.): 5.04 minutes.

EXAMPLE 113

(2S,4S,5S,7S)-5-Amino-4-hydroxy-2-isopropyl-7-[4-methoxy-3-(3-methoxy-propoxy)-benzyl]-8-methyl-nonanoic acid 2-trifluoromethoxy-benzylamide The title compound prepared in accordance with General Procedure (I).

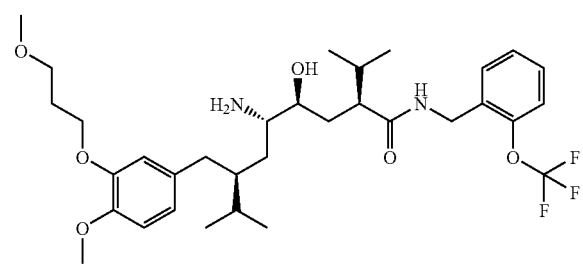

MS (LC-MS): 627.3 [M]$^+$; R$_f$[CH$_2$Cl$_2$:MeOH (9:1)]: 0.31 minutes.

EXAMPLE 114

(2S,4S,5S,7S)-5-Amino-4-hydroxy-2-isopropyl-7-[4-methoxy-3-(3-methoxy-propoxy)-benzyl]-8-methyl-nonanoic acid 3-trifluoromethoxy-benzylamide The title compound prepared in accordance with General Procedure (I).

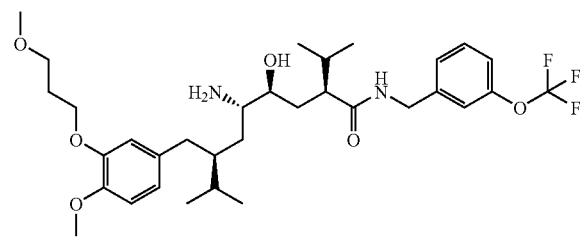

MS (LC-MS): 627.2 [M]$^+$; R$_f$[CH$_2$Cl$_2$:MeOH (9:1)]: 0.17 minutes.

EXAMPLE 115

(2S,4S,5S,7S)-5-Amino-4-hydroxy-2-isopropyl-7-[4-methoxy-3-(3-methoxy-propoxy)-benzyl]-8-methyl-nonanoic acid 4-trifluoromethoxy-benzylamide The title compound prepared in accordance with General Procedure (I).

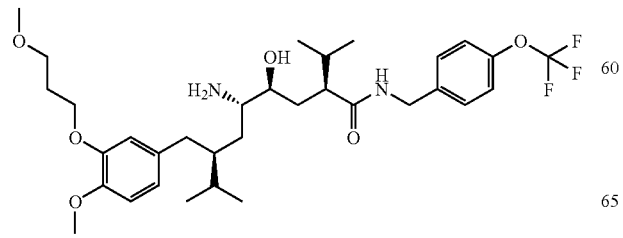

MS (LC-MS): 627.3 [M]$^+$; R$_f$[CH$_2$Cl$_2$:MeOH (9:1)]: 0.26 minutes.

EXAMPLE 116

(2S,4S,5S,7S)-5-Amino-4-hydroxy-2-isopropyl-7-[4-methoxy-3-(3-methoxy-propoxy)-benzyl]-8-methyl-nonanoic acid 2-fluoro-benzylamide The title compound prepared in accordance with General Procedure (I).

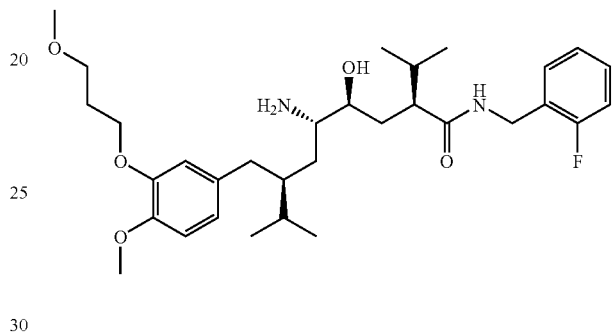

MS (LC-MS): 561.3 [M]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.03 minutes.

EXAMPLE 117

(2S,4S,5S,7S)-5-Amino-4-hydroxy-2-isopropyl-7-[4-methoxy-3-(3-methoxy-propoxy)-benzyl]-8-methyl-nonanoic acid 3-fluoro-benzylamide The title compound prepared in accordance with General Procedure (I).

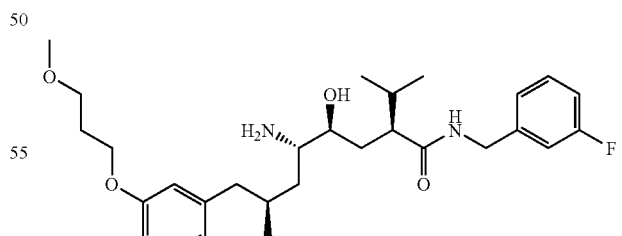

MS (LC-MS): 561.3 [M]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.09 minutes.

EXAMPLE 118

(2S,4S,5S,7S)-5-Amino-4-hydroxy-2-isopropyl-7-[4-methoxy-3-(3-methoxy-propoxy)-benzyl]-8-methyl-nonanoic acid 4-fluoro-benzylamide The title compound prepared in accordance with General Procedure (I).

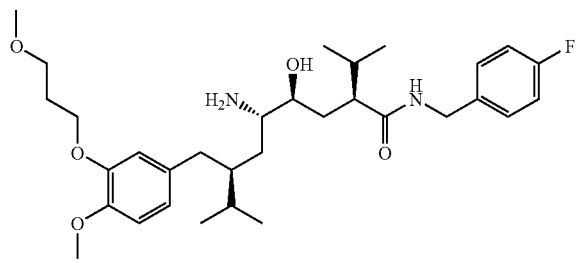

MS (LC-MS): 561.3 [M+H]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.08 minutes.

EXAMPLE 119

(2S,4S,5S,7S)-5-Amino-4-hydroxy-2-isopropyl-7-[4-methoxy-3-(3-methoxy-propoxy)-benzyl]-8-methyl-nonanoic acid [(R)-1-(4-fluoro-phenyl)-ethyl]-amide The title compound prepared in accordance with General Procedure (I).

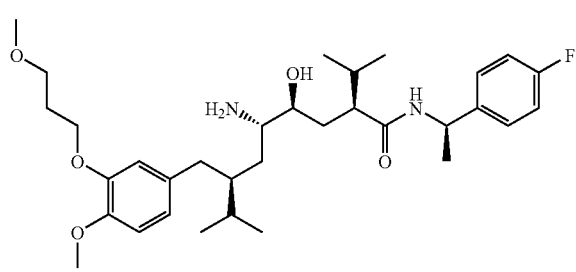

MS (LC-MS): 575.1 [M+H]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.11 minutes.

EXAMPLE 120

(2S,4S,5S,7S)-5-Amino-4-hydroxy-2-isopropyl-7-[4-methoxy-3-(3-methoxy-propoxy)-benzyl]-8-methyl-nonanoic acid [(S)-1-(4-fluoro-phenyl)-ethyl]-amide The title compound prepared in accordance with General Procedure (I).

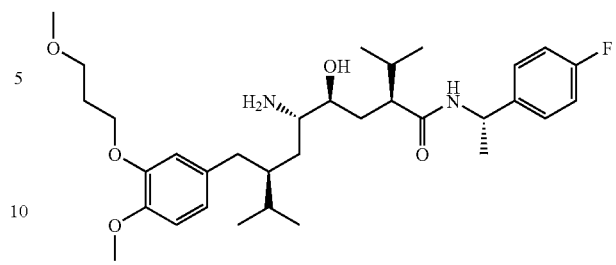

MS (LC-MS): 575.1 [M+H]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.09 minutes.

EXAMPLE 121

(2S,4S,5S,7S)-5-Amino-4-hydroxy-2-isopropyl-7-[4-methoxy-3-(3-methoxy-propoxy)-benzyl]-8-methyl-nonanoic acid 2-chloro-benzylamide The title compound prepared in accordance with General Procedure (I).

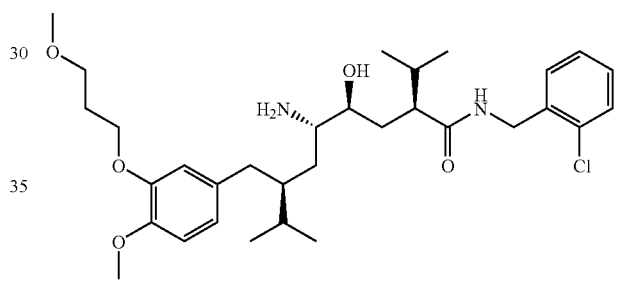

MS (LC-MS): 577.3 [M+H]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.15 minutes.

EXAMPLE 122

(2S,4S,5S,7S)-5-Amino-4-hydroxy-2-isopropyl-7-[4-methoxy-3-(3-methoxy-propoxy)-benzyl]-8-methyl-nonanoic acid 3-chloro-benzylamide The title compound prepared in accordance with General Procedure (I).

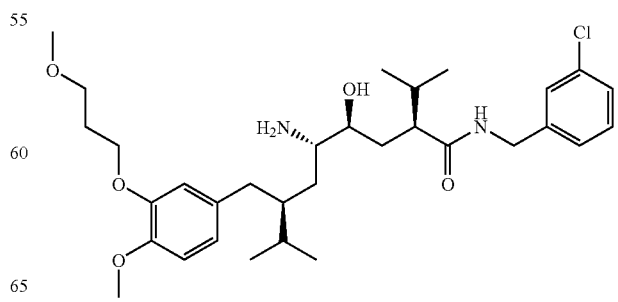

MS (LC-MS): 577.3 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.18 minutes.

EXAMPLE 123

(2S,4S,5S,7S)-5-Amino-4-hydroxy-2-isopropyl-7-[4-methoxy-3-(3-methoxy-propoxy)-benzyl]-8-methyl-nonanoic acid 4-chloro-benzylamide The title compound prepared in accordance with General Procedure (I).

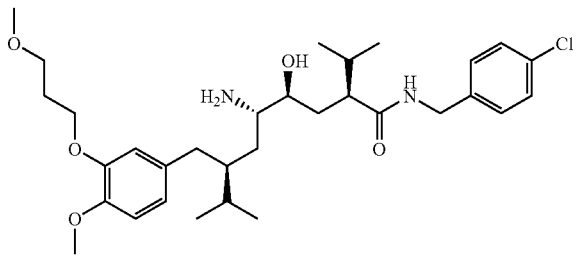

MS (LC-MS): 577.3 [M]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.14 minutes.

EXAMPLE 124

(2S,4S,5S,7S)-5-Amino-4-hydroxy-2-isopropyl-7-[4-methoxy-3-(3-methoxy-propoxy)-benzyl]-8-methyl-nonanoic acid 2,5-difluoro-benzylamide The title compound prepared in accordance with General Procedure (I).

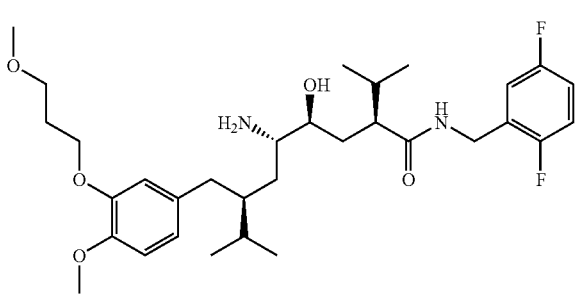

MS (LC-MS): 579.1 [M]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.13 minutes.

EXAMPLE 125

(2S,4S,5S,7S)-5-Amino-4-hydroxy-2-isopropyl-7-[4-methoxy-3-(3-methoxy-propoxy)-benzyl]-8-methyl-nonanoic acid 2,4-difluoro-benzylamide The title compound prepared in accordance with General Procedure (I).

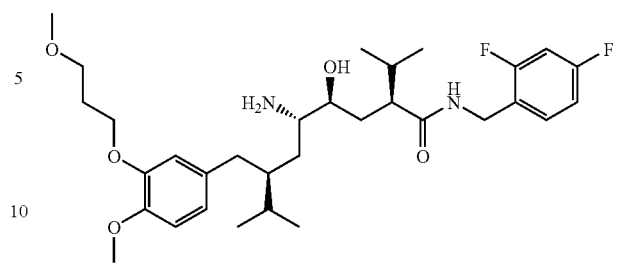

MS (LC-MS): 579.1 [M]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.07 minutes.

EXAMPLE 126

(2S,4S,5S,7S)-5-Amino-4-hydroxy-2-isopropyl-7-[4-methoxy-3-(3-methoxy-propoxy)-benzyl]-8-methyl-nonanoic acid 2,6-difluoro-benzylamide The title compound prepared in accordance with General Procedure (I).

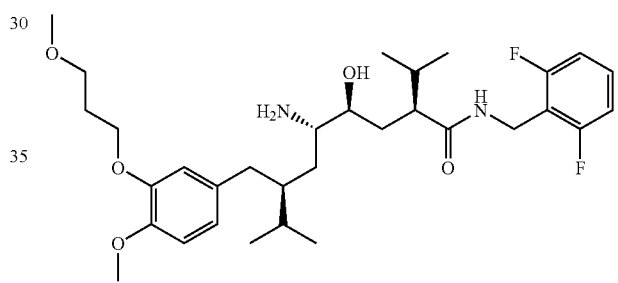

MS (LC-MS): 579.0 [M]$^+$; $t_R$ (HPLC, C8 column, 5-95% CH$_3$CN/H$_2$O/6.5 minutes, 95% CH$_3$CN/H$_2$O/1 minute, flow: 0.5 mL/min.): 4.63 minutes.

EXAMPLE 127

(2S,4S,5S,7S)-5-Amino-4-hydroxy-2-isopropyl-7-[4-methoxy-3-(3-methoxy-propoxy)-benzyl]-8-methyl-nonanoic acid 3,4-difluoro-benzylamide The title compound prepared in accordance with General Procedure (I).

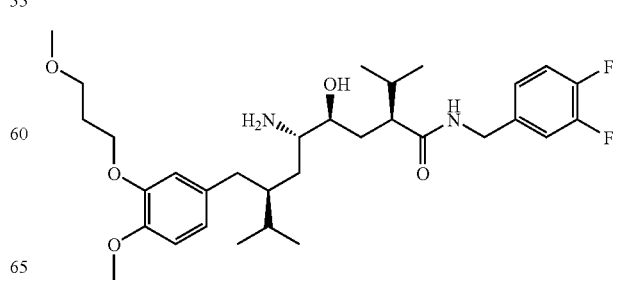

MS (LC-MS): 579.0 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.11 minutes.

EXAMPLE 128

(2S,4S,5S,7S)-5-Amino-4-hydroxy-2-isopropyl-7-[4-methoxy-3-(3-methoxy-propoxy)-benzyl]-8-methyl-nonanoic acid 3,5-difluoro-benzylamide The title compound prepared in accordance with General Procedure (I).

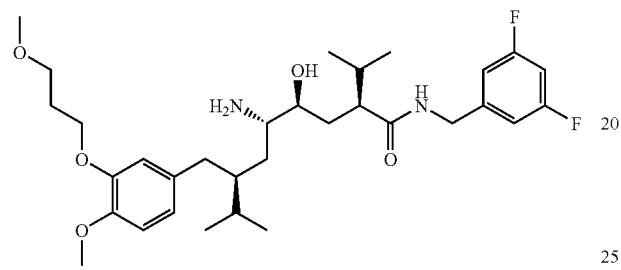

MS (LC-MS): 579.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.12 minutes.

EXAMPLE 129

(2S,4S,5S,7S)-5-Amino-4-hydroxy-2-isopropyl-7-[4-methoxy-3-(3-methoxy-propoxy)-benzyl]-8-methyl-nonanoic acid 2-trifluoromethyl-benzylamide The title compound prepared in accordance with General Procedure (I).

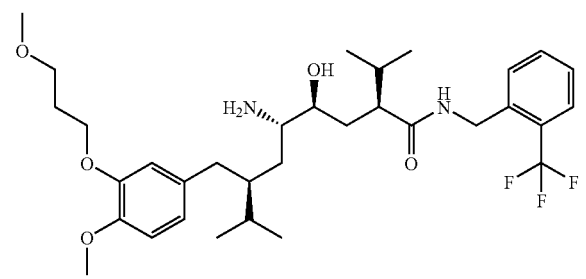

MS (LC-MS): 611.1 [M]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.43 minutes.

EXAMPLE 130

(2S,4S,5S,7S)-5-Amino-4-hydroxy-2-isopropyl-7-[4-methoxy-3-(3-methoxy-propoxy)-benzyl]-8-methyl-nonanoic acid 3-trifluoromethyl-benzylamide The title compound prepared in accordance with General Procedure (I).

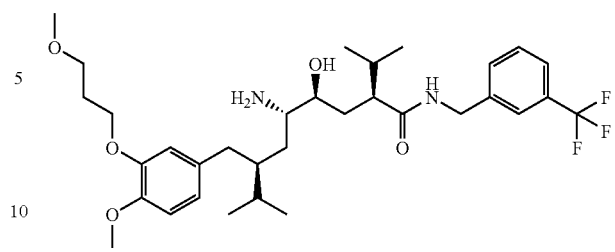

MS (LC-MS): 611.1 [M+H]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.59 minutes.

EXAMPLE 131

(2S,4S,5S,7S)-5-Amino-4-hydroxy-2-isopropyl-7-[4-methoxy-3-(3-methoxy-propoxy)-benzyl]-8-methyl-nonanoic acid 4-trifluoromethyl-benzylamide The title compound prepared in accordance with General Procedure (I).

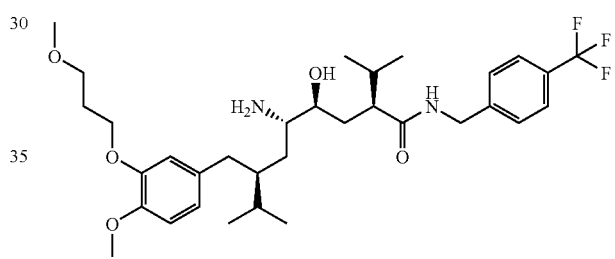

MS (LC-MS): 611.0 [M]$^+$; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.43 minutes.

EXAMPLE 132

(2S,4S,5S,7S)-5-Amino-4-hydroxy-2-isopropyl-7-[4-methoxy-3-(3-methoxy-propoxy)-benzyl]-8-methyl-nonanoic acid 4-cyano-benzylamide The title compound prepared in accordance with General Procedure (I).

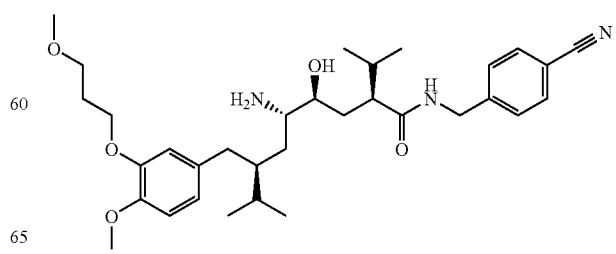

MS (LC-MS): 568.3 [M]+; $R_f$[CH$_2$Cl$_2$:MeOH (9:1)]: 0.25 minutes.

EXAMPLE 133

(2S,4S,5S,7S)-5-Amino-4-hydroxy-2-isopropyl-7-[4-methoxy-3-(3-methoxy-propoxy)-benzyl]-8-methyl-nonanoic acid 4-dimethylamino-benzylamide The title compound prepared in accordance with General Procedure (I).

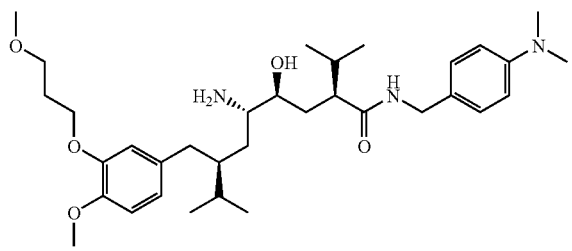

MS (LC-MS): 586.3 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.26 minutes.

EXAMPLE 134

(2S,4S,5S,7S)-5-Amino-4-hydroxy-2-isopropyl-7-[4-methoxy-3-(3-methoxy-propoxy)-benzyl]-8-methyl-nonanoic acid (2,3-dihydro-benzo[1,4]dioxin-6-ylmethyl)-amide The title compound prepared in accordance with General Procedure (I).

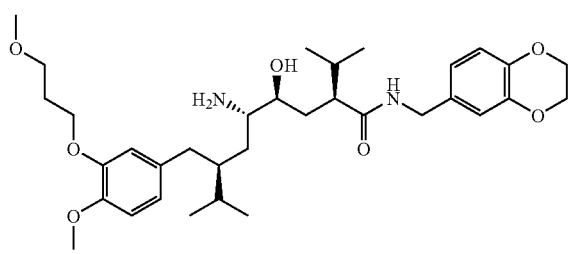

MS (LC-MS): 601.3 [M]+; $R_f$[CH$_2$Cl$_2$:MeOH (9:1)]: 0.25 minutes.

EXAMPLE 135

(2S,4S,5S,7S)-5-Amino-4-hydroxy-2-isopropyl-7-[4-methoxy-3-(3-methoxy-propoxy)-benzyl]-8-methyl-nonanoic acid (2,3-dihydro-benzo[1,4]dioxin-5-ylmethyl)-amide The title compound prepared in accordance with General Procedure (I).

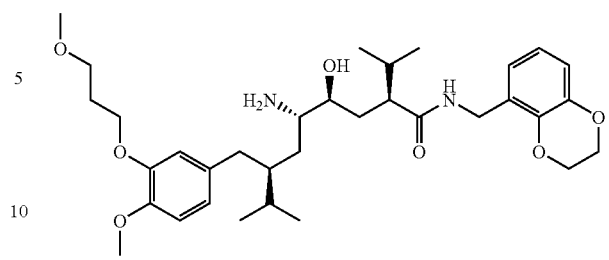

MS (LC-MS): 601.3 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.07 minutes.

EXAMPLE 136

(2S,4S,5S,7S)-5-Amino-4-hydroxy-2-isopropyl-7-[4-methoxy-3-(3-methoxy-propoxy)-benzyl]-8-methyl-nonanoic acid (3,4-dihydro-2H-benzo[b][1,4]dioxepin-7-ylmethyl)-amide The title compound prepared in accordance with General Procedure (I).

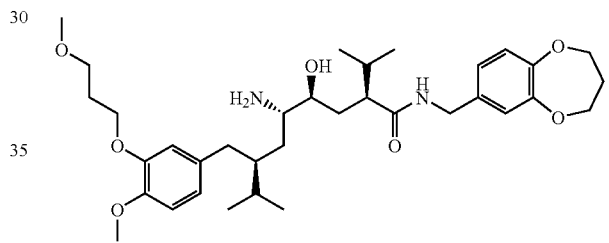

MS (LC-MS): 615.3 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.07 minutes.

EXAMPLE 137

(2S,4S,5S,7S)-5-Amino-4-hydroxy-2-isopropyl-7-[4-methoxy-3-(3-methoxy-propoxy)-benzyl]-8-methyl-nonanoic acid (2,3-dihydro-benzofuran-5-ylmethyl)-amide The title compound prepared in accordance with General Procedure (I).

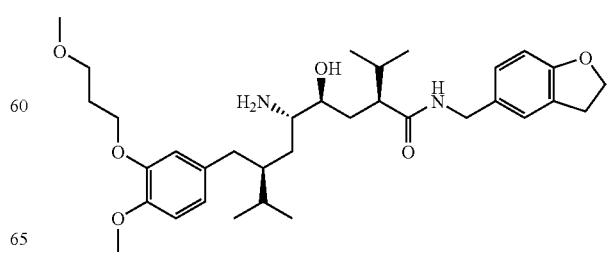

MS (LC-MS): 585.3 [M]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.07 minutes.

EXAMPLE 138

(2S,4S,5S,7S)-5-Amino-4-hydroxy-2-isopropyl-7-[4-methoxy-3-(3-methoxy-propoxy)-benzyl]-8-methyl-nonanoic acid (benzofuran-4-ylmethyl)-amide The title compound prepared in accordance with General Procedure (I).

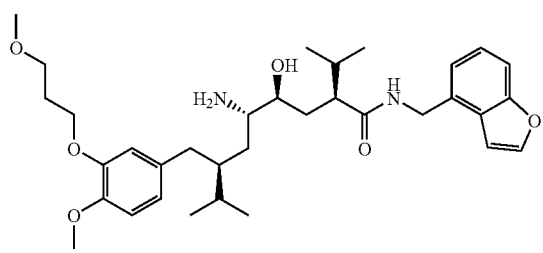

MS (LC-MS): 583.3 [M]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.11 minutes.

EXAMPLE 139

(2S,4S,5S,7S)-5-Amino-4-hydroxy-2-isopropyl-7-[4-methoxy-3-(3-methoxy-propoxy)-benzyl]-8-methyl-nonanoic acid 2-piperidin-1-yl-benzylamide The title compound prepared in accordance with General Procedure (I).

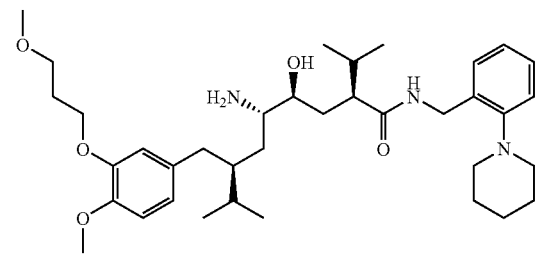

MS (LC-MS): 626.4 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 4.58 minutes.

EXAMPLE 140

(2S,4S,5S,7S)-5-Amino-4-hydroxy-2-isopropyl-7-[4-methoxy-3-(3-methoxy-propoxy)-benzyl]-8-methyl-nonanoic acid 3-piperidin-1-yl-benzylamide The title compound prepared in accordance with General Procedure (I).

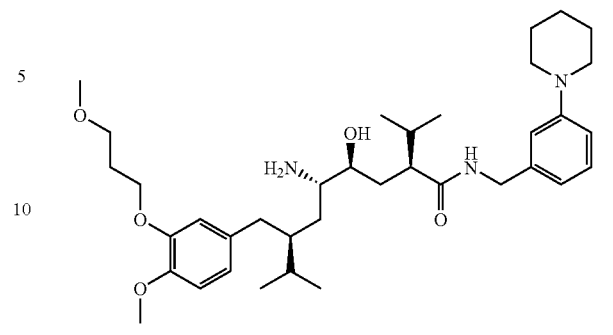

MS (LC-MS): 626.3 [M]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 4.35 minutes.

EXAMPLE 141

(2S,4S,5S,7S)-5-Amino-4-hydroxy-2-isopropyl-7-[4-methoxy-3-(3-methoxy-propoxy)-benzyl]-8-methyl-nonanoic acid 4-piperidin-1-yl-benzylamide The title compound prepared in accordance with General Procedure (I).

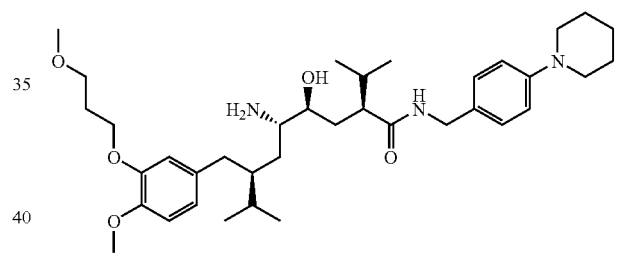

MS (LC-MS): 626.4 [M]⁺; $R_f$[CH₂Cl₂:MeOH (9:1)]: 0.35 minutes.

EXAMPLE 142

(2S,4S,5S,7S)-5-Amino-4-hydroxy-2-isopropyl-7-[4-methoxy-3-(3-methoxy-propoxy)-benzyl]-8-methyl-nonanoic acid 2-morpholin-4-yl-benzylamide The title compound prepared in accordance with General Procedure (I).

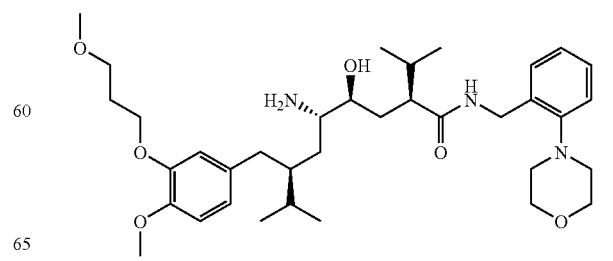

MS (LC-MS): 628.4 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.58 minutes.

EXAMPLE 143

(2S,4S,5S,7S)-5-Amino-4-hydroxy-2-isopropyl-7-[4-methoxy-3-(3-methoxy-propoxy)-benzyl]-8-methyl-nonanoic acid 3-morpholin-4-yl-benzylamide The title compound prepared in accordance with General Procedure (I).

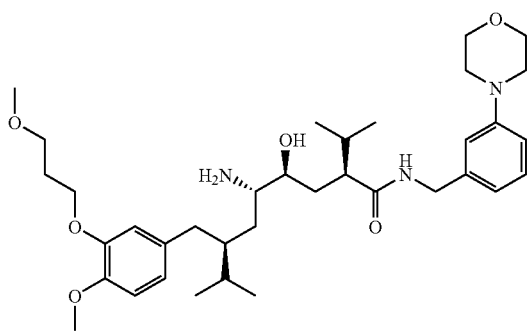

MS (LC-MS): 628.3 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.61 minutes.

EXAMPLE 144

(2S,4S,5S,7S)-5-Amino-4-hydroxy-2-isopropyl-7-[4-methoxy-3-(3-methoxy-propoxy)-benzyl]-8-methyl-nonanoic acid 4-morpholin-4-yl-benzylamide The title compound prepared in accordance with General Procedure (I).

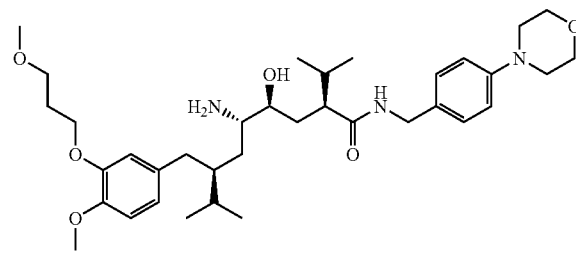

MS (LC-MS): 628.4 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.55 minutes.

EXAMPLE 145

(2S,4S,5S,7S)-5-Amino-4-hydroxy-2-isopropyl-7-[4-methoxy-3-(3-methoxy-propoxy)-benzyl]-8-methyl-nonanoic acid 2-pyrrolidin-1-yl-benzylamide The title compound prepared in accordance with General Procedure (I).

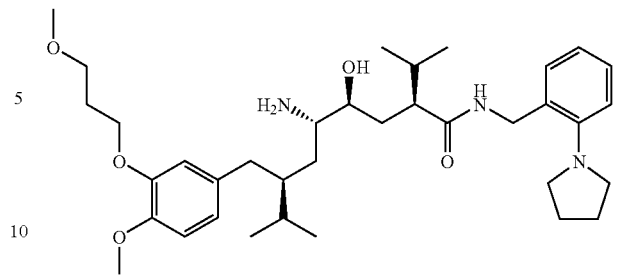

MS (LC-MS): 612.4 [M+H]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.46 minutes.

EXAMPLE 146

(2S,4S,5S,7S)-5-Amino-4-hydroxy-2-isopropyl-7-[4-methoxy-3-(3-methoxy-propoxy)-benzyl]-8-methyl-nonanoic acid 3-pyrrolidin-1-yl-benzylamide The title compound prepared in accordance with General Procedure (I).

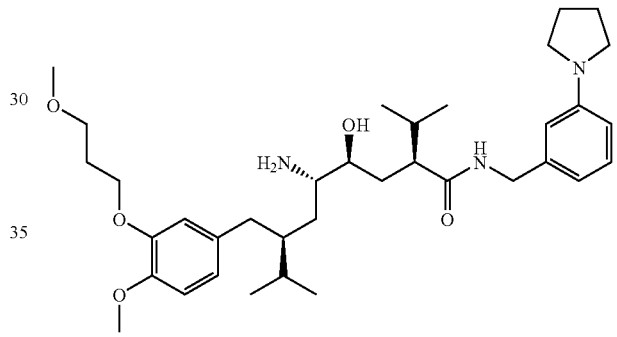

MS (LC-MS): 612.3 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.66 minutes.

EXAMPLE 147

(2S,4S,5S,7S)-5-Amino-4-hydroxy-2-isopropyl-7-[4-methoxy-3-(3-methoxy-propoxy)-benzyl]-8-methyl-nonanoic acid 4-pyrrolidin-1-yl-benzylamide The title compound prepared in accordance with General Procedure (I).

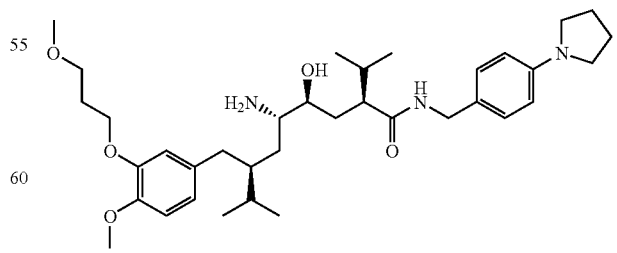

MS (LC-MS): 612.4 [M]+; $t_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 4.37 minutes.

EXAMPLE 148

(2S,4S,5S,7S)-5-Amino-4-hydroxy-2-isopropyl-7-[4-methoxy-3-(3-methoxy-propoxy)-benzyl]-8-methyl-nonanoic acid 3-pyrrol-1-yl-benzylamide The title compound prepared in accordance with General Procedure (I).

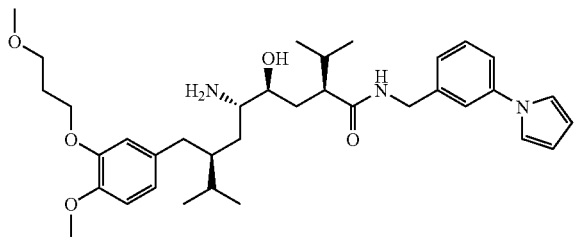

MS (LC-MS): 608.3 [M]$^+$; R$_f$[CH$_2$Cl$_2$:MeOH (9:1)]: 0.37 minutes.

EXAMPLE 149

(2S,4S,5S,7S)-5-Amino-4-hydroxy-2-isopropyl-7-[4-methoxy-3-(3-methoxy-propoxy)-benzyl]-8-methyl-nonanoic acid 4-pyrrol-1-yl-benzylamide The title compound prepared in accordance with General Procedure (I).

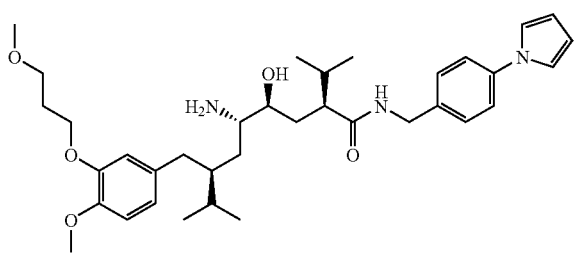

MS (LC-MS): 608.3 [M]$^+$; R$_f$[CH$_2$Cl$_2$:MeOH (9:1)]: 0.35 minutes.

EXAMPLE 150

(2S,4S,5S,7S)-5-Amino-4-hydroxy-2-isopropyl-7-[4-methoxy-3-(3-methoxy-propoxy)-benzyl]-8-methyl-nonanoic acid 4-thiophen-3-yl-benzylamide The title compound prepared in accordance with General Procedure (I).

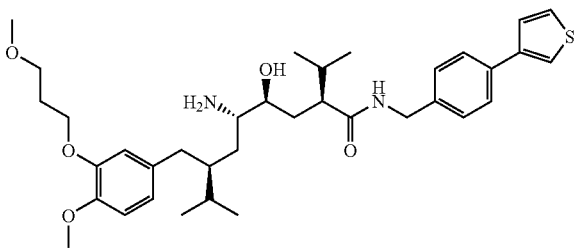

MS (LC-MS): 625.3 [M]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.45 minutes.

EXAMPLE 151

(2S,4S,5S,7S)-5-Amino-4-hydroxy-2-isopropyl-7-[4-methoxy-3-(3-methoxy-propoxy)-benzyl]-8-methyl-nonanoic acid phenethyl-amide The title compound prepared in accordance with General Procedure (I).

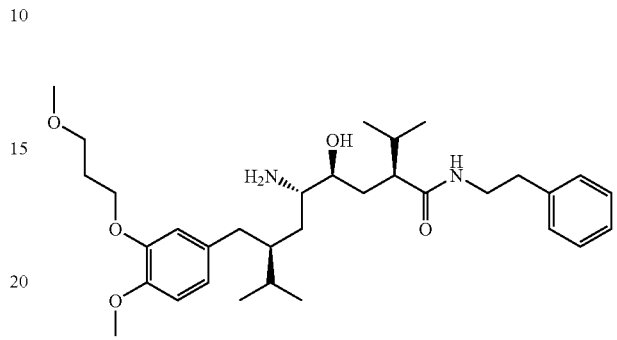

MS (LC-MS): 557.1 [M]$^+$; t$_R$ (HPLC, C18 column, 10-100% CH$_3$CN/H$_2$O/5 minutes, 100% CH$_3$CN/3 minutes, 100-10% CH$_3$CN/H$_2$O/3 minutes, flow: 1.5 mL/min.): 5.18 minutes.

Example 152

(2S,4S,5S,7S)-5-Amino-4-hydroxy-2-isopropyl-7[4-methoxy-3-(3-methoxy-propoxy)-benzyl]-8-methyl-nonanoic acid [1-methyl-1-(1-phenyl-cyclopropyl)-ethyl]-amide The title compound prepared in accordance with General Procedure (II).

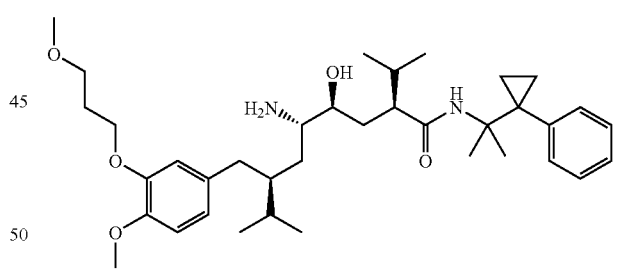

MS (LC-MS): 611.1 [M+H]$^+$; t$_R$ (HPLC, C8 column, 5-95% CH$_3$CN/H$_2$O/6.5 minutes, 95% CH$_3$CN/H$_2$O/1 minute, flow: 0.5 mL/min.): 5.6 minutes.

EXAMPLE 153

(2S,4S,5S,7S)-5-Amino-4-hydroxy-2-isopropyl-7-[4-methoxy-3-(3-methoxy-propoxy)-benzyl]-8-methyl-nonanoic acid [2-(2-fluoro-phenyl)-ethyl]-amide The title compound prepared in accordance with General Procedure (I).

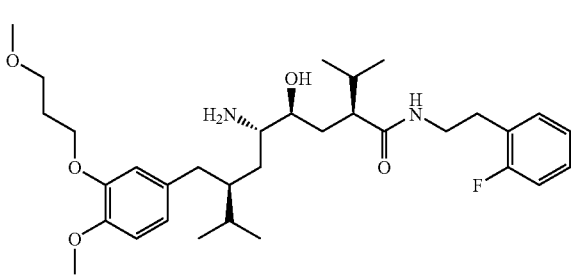

MS (LC-MS): 575.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.12 minutes.

EXAMPLE 154

(2S,4S,5S,7S)-5-Amino-4-hydroxy-2-isopropyl-7-[4-methoxy-3-(3-methoxy-propoxy)-benzyl]-8-methyl-nonanoic acid [2-(3-fluoro-phenyl)-ethyl]-amide The title compound prepared in accordance with General Procedure (I).

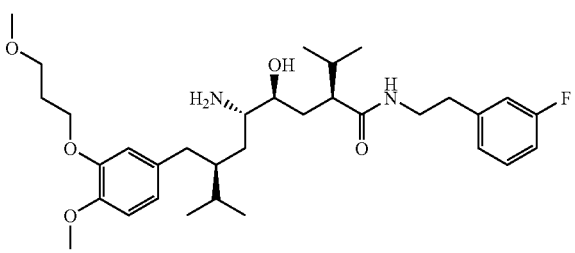

MS (LC-MS): 575.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.11 minutes.

EXAMPLE 155

(2S,4S,5S,7S)-5-Amino-4-hydroxy-2-isopropyl-7-[4-methoxy-3-(3-methoxy-propoxy)-benzyl]-8-methyl-nonanoic acid [2-(4-fluoro-phenyl)-ethyl]-amide The title compound prepared in accordance with General Procedure (I).

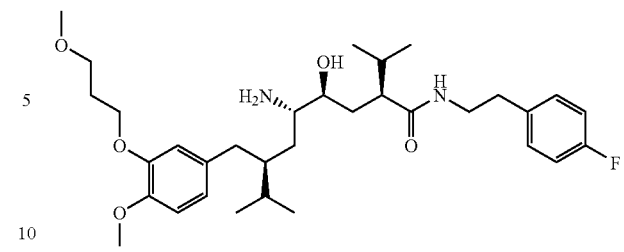

MS (LC-MS): 575.0 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.06 minutes.

EXAMPLE 156

(2S,4S,5S,7S)-5-Amino-4-hydroxy-2-isopropyl-7-[4-methoxy-3-(3-methoxy-propoxy)-benzyl]-8-methyl-nonanoic acid (2-phenoxy-ethyl)-amide The title compound prepared in accordance with General Procedure (I).

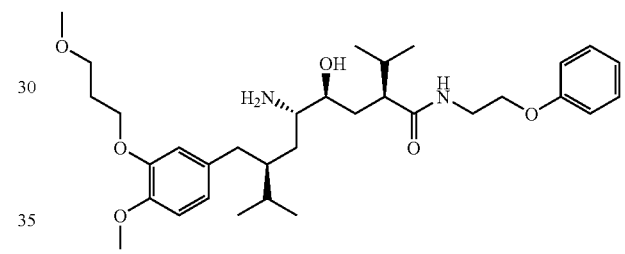

MS (LC-MS): 573.3 [M]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.08 minutes.

EXAMPLE 157

(2S,4S,5S,7S)-5-Amino-4-hydroxy-2-isopropyl-7-[4-methoxy-3-(3-methoxy-propoxy)-benzyl]-8-methyl-nonanoic acid [2-(4-methoxy-phenoxy)-ethyl]-amide The title compound prepared in accordance with General Procedure (I).

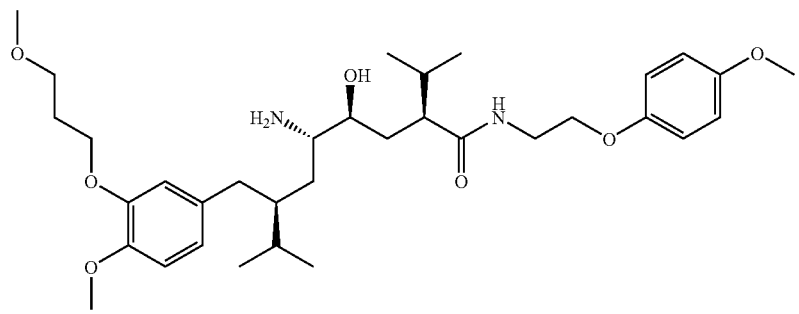

MS (LC-MS): 603.1 [M+H]⁺; $t_R$ (HPLC, C18 column, 10-100% CH₃CN/H₂O/5 minutes, 100% CH₃CN/3 minutes, 100-10% CH₃CN/H₂O/3 minutes, flow: 1.5 mL/min.): 5.09 minutes.

EXAMPLE 158

Gelatin Solution

A sterile-filtered aqueous solution, containing 20% cyclodextrins as solubiliser, of one of the compounds of formula (I), mentioned in the preceding Examples, as active ingredient, is so mixed, with the application of heat and under aseptic conditions, with a sterile gelatin solution containing phenol as preservative, that 1.0 mL of solution has the following composition:

| | |
|---|---:|
| active ingredient | 3 mg |
| gelatin | 150.0 mg |
| phenol | 4.7 mg |
| dist. water containing 20% cyclodextrins as solubiliser | 1.0 mL |

EXAMPLE 159

Sterile Dry Substance for Injection

Five (5) mg of one of the compounds of formula (I), mentioned in the preceding Examples, as active ingredient, are dissolved in 1 mL of an aqueous solution containing 20 mg of mannitol and 20% cyclodextrins as solubiliser. The solution is sterile-filtered and, under aseptic conditions, introduced into a 2 mL ampoule, deep-frozen and lyophilised. Before being used, the lyophilisate is dissolved in 1 mL of distilled water or 1 mL of physiological saline. The solution is administered intramuscularly or intravenously. The formulation can also be filled into double-chamber disposable syringes.

EXAMPLE 160

Nasal Spray

Five hundred (500) mg of finely ground (<5.0 gm) powder of one of the compounds of formula (I), mentioned in the preceding Examples, are suspended as active ingredient in a mixture of 3.5 mL of "Myglyol 8 12" and 0.08 g of benzyl alcohol. The suspension is introduced into a container having a metering valve. Five (5.0) g of "Freon 12" are introduced under pressure through the valve into the container. The "Freon" is dissolved in the Myglyol/benzyl alcohol mixture by shaking. The spray container contains approximately 100 single doses which can be administered individually.

EXAMPLE 161

Film-coated Tablets

The following constituents are processed for the preparation of 10 000 tablets each containing 100 mg of active ingredient:

| | |
|---|---:|
| active ingredient | 1000 g |
| corn starch | 680 g |
| colloidal silicic acid | 200 g |

-continued

| | |
|---|---:|
| magnesium stearate | 20 g |
| stearic acid | 50 g |
| sodium carboxymethyl starch | 250 g |
| water | quantum satis |

A mixture of one of the compounds of formula (I), mentioned in the preceding Examples, as active ingredient, 50 g of corn starch and the colloidal silicic acid is processed into a moist mass with starch paste prepared from 250 g of corn starch and 2.2 kg of demineralised water. The mass is forced through a sieve having a mesh size of 3 mm and dried at 45° C. for 30 minutes in a fluidised bed drier. The dried granules are pressed through a sieve having a mesh size of 1 ram, mixed with a previously sieved mixture (1 mm sieve) of 330 g of corn starch, the magnesium stearate, the stearic acid and the sodium carboxymethyl starch and compressed to form slightly biconvex tablets.

Although the present invention has been described in considerable detail with reference to certain preferred versions thereof, other versions are possible without departing from the spirit and scope of the preferred versions contained herein. All references and patents (U.S. and others) referred to herein are hereby incorporated by reference in their entirety as if set forth in full herein.

What is claimed is:
1. A δ-amino-γ-hydroxy-ω-aryl-alkanoic acid amide compound of formula (I)

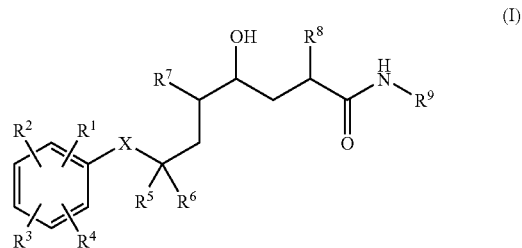

wherein
R¹ is hydrogen, halogen, optionally halogenated alkyl, cycloalkyl, hydroxy, optionally halogenated alkoxy, cycloalkoxy, lower alkoxy-lower alkoxy or free or esterified or amidated carboxy-lower alkoxy or lower alkyl;
R² is hydrogen, halogen, optionally halogenated lower alkyl, hydroxy, cycloalkyl, cycloalkoxy, optionally halogenated lower alkoxy-lower alkyl, optionally substituted lower alkoxy-lower alkyl, cycloalkoxy-lower alkyl; optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl, optionally hydrogenated heteroaryl-lower alkyl, amino-lower alkoxy that is substituted by lower alkyl, by lower alkanoyl and/or by lower alkoxycarbonyl; oxo-lower alkoxy, lower alkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl lower alkoxy, optionally S-oxidised lower alkylthio-lower alkoxy, lower alkylthio-(hydroxy)-lower alkoxy, aryl-lower alkoxy, aryl-lower alkyl, aryl-lower alkoxy, optionally hydrogenated heteroaryl-lower alkoxy, optionally hydrogenated heteroaryl-lower alkyl, cyano-lower alkoxy, cyano-lower alkyl, free or esterified or amidated carboxy-lower alkoxy or free or esterified or amidated carboxy-lower alkyl;

$R^3$ and $R^4$ are independently hydrogen, halogen, optionally halogenated lower alkyl, hydroxy, optionally halogenated lower alkoxy or cycloalkoxy, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene, cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene, cyano-lower alkoxy or free or esterified or amidated carboxy-lower alkoxy; or $R^4$ together with $R_3$ is lower alkeneoxy, lower alkylene-dioxy or a fused-on aryl, optionally hydrogenated heteroaryl or cycloalkyl ring;

X is methylene, hydroxymethylene, oxygen, optionally lower alkyl substituted nitrogen, optionally oxidized sulfur;

$R^5$ is lower alkyl or cycloalkyl;

$R^6$ is hydrogen, lower alkyl, hydroxy, alkoxy or halogen;

$R^7$ is unsubstituted or N-mono- or N,N-di-lower alkylated or N-lower alkanoylated amino;

$R^8$ is lower alkyl, lower alkenyl, cycloalkyl or aryl-lower alkyl;

$R^9$ is optionally substituted cycloalkyl-alkyl, optionally substituted aryl-alkyl, optionally substituted aryloxy-aryl, or a pharmaceutically acceptable salt thereof.

2. The compound according to claim 1 wherein
$R^9$ is optionally substituted cycloalkyl-alkyl (OH, alkoxy, alkoxy-alkyl, halogens on cycloalkyl), optionally substituted aryl-alkyl,
or a pharmaceutically acceptable salt thereof.

3. The compound according to claim 2 wherein
$R^1$ and $R^4$ are hydrogen;
$R^2$ is lower alkoxy-lower alkoxy;
$R^3$ is halogen or mono, di or tri-halo-substituted alkyl;
or a pharmaceutically acceptable salt thereof.

4. The compound according to claim 3 wherein the halogen/halo is fluorine or chlorine;
or a pharmaceutically acceptable salt thereof.

5. The compound according to claim 4 wherein
$R^3$ is fluorine or trifluoromethyl;
or a pharmaceutically acceptable salt thereof.

6. The compound according to claim 5 wherein $R^2$ is in the meta position and $R^3$ is in the para position;
or a pharmaceutically acceptable salt thereof.

7. The compound according to claim 5 wherein $R^3$ is in the ortho position;
or a pharmaceutically acceptable salt thereof.

8. The compound according to claim 5 wherein $R^3$ is in the meta position;
or a pharmaceutically acceptable salt thereof.

9. The compound according to claim 2 wherein $R^2$ is in the meta position and is lower alkoxy-lower alkoxy optionally substituted by halogen(s);
or a pharmaceutically acceptable salt thereof.

10. The δ-amino-γ-hydroxy-ω-aryl-alkanoic acid amide compound according to claim 1 having formula (Ia)

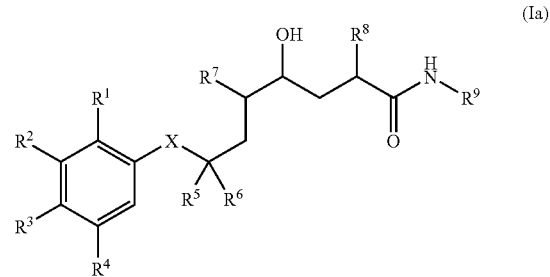

wherein
$R^1$ is hydrogen, halogen, optionally halogenated alkyl, cycloalkyl, hydroxy, optionally halogenated alkoxy, cycloalkoxy, lower alkoxy-lower alkoxy or free or esterified or amidated carboxy-lower alkoxy or lower alkyl;

$R^2$ is hydrogen, halogen, optionally halogenated lower alkyl, hydroxy, cycloalkyl, cycloalkoxy, optionally halogenated lower alkoxy-lower alkyl; optionally substituted lower alkoxy-lower alkoxy, cycloalkoxy-lower alkyl; optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl; optionally hydrogenated heteroaryl-lower alkyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, aryl-lower alkyl, aryl-lower alkoxy, optionally hydrogenated heteroaryl-lower alkoxy, optionally hydrogenated heteroaryl-lower alkyl, cyano-lower alkoxy, cyano-lower alkyl, free or esterified or amidated carboxy-lower alkoxy or free or esterified or amidated carboxy-lower alkyl;

$R^3$ and $R^4$ are independently hydrogen, halogen, optionally halogenated lower alkyl, hydroxy, optionally halogenated lower alkoxy or cycloalkoxy, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxalower alkylene or by optionally S-oxidised thia-lower alkylene; cyano-lower alkoxy or free or esterified or amidated carboxy-lower alkoxy; or $R^4$ together with $R_3$ is lower alkeneoxy, alkylenedioxy or a fused-on aryl, optionally hydrogenated heteroaryl or cycloalkyl ring;

X is methylene, hydroxymethylene, oxygen, optionally lower alkyl substituted nitrogen or optionally oxidized sulfur;

$R^5$ is lower alkyl or cycloalkyl;

$R^6$ is hydrogen, lower alkyl, hydroxy, alkoxy or halogen;

$R^7$ is unsubstituted or N-mono- or N,N-di-lower alkylated or N-lower alkanoylated amino;

$R^8$ is lower alkyl, lower alkenyl, cycloalkyl or aryl-lower alkyl;

$R^9$ is optionally substituted cycloalkyl-alkyl, optionally substituted aryl-alkyl, optionally substituted aryloxy-alkyl or a pharmaceutically acceptable salt thereof.

11. The compound according to claim 10 wherein
$R^9$ is cycloalkyl-alkyl optionally substituted with alkyl, hydroxy, alkoxy, alkoxy-alkoxy or halogens on cycloalkyl or halogens on alkyl or halogens on alkoxy; or optionally substituted aryl-alkyl;

or a pharmaceutically acceptable salt thereof.

12. The compound according to claim 10 wherein
$R^9$ is optionally substituted aryl-alkyl, optionally substituted aryloxy-alkyl, cycloalkyl-alkyl optionally substituted by one or more substituents such as alkenyl, alknyl, halo, hydroxy, alkoxy, alkoxy-alkoxy, alkvlthio, arylthio, aryl-alkoxv, carbamoyl, sulfamoyl, sulfonyl, optionally substituted amino, cyano, carboxy, alkoxycarbonyl, aryl, arvloxy, heterocyclyl or alkyl optionally substituted by amino, halo. hydroxy, alkoxy, carboxy, carbamoyl or heterocyclyl; or $R^9$ is aryl lower alkyl wherein aryl is selected from phenyl or naphthyl each of which is unsubstituted or mono-, di- or tri-substituted by lower alkyl, lower alkoxy optionally substituted with halogens, hydroxy, lower alkylamino, di-lower alkylamino, halogen and/or by trifluoromethyl;

or a pharmaceutically acceptable salt thereof.

13. The compound according to claim 12 wherein
$R^1$ is hydrogen;
$R^2$ is $C_1$-$C_4$ alkoxy - $C_1$-$C_4$ alkoxy or $C_1$-$C_4$ alkoxy - $C_1$-$C_4$ alkyl;
$R^3$ is $C_1$-$C_4$ alkyl or $C_1$-$C_4$ alkoxy;
$R^4$ is hydrogen;
X is methylene;
$R^5$ is lower alkyl;
$R^6$ is hydrogen;
$R^7$ is unsubstituted amino;
$R^8$ is branched $C_3$-$C_4$ alkyl;
$R^9$ is optionally substituted cycloalkyl-alkyl;
or a pharmaceutically acceptable salt thereof.

14. The compound according to claim 13 wherein
$R^2$ is 3-methoxypropyloxy;
$R^3$ is methoxy;
$R^5$ is isopropyl;
$R^8$ is isopropyl;
or a pharmaceutically acceptable salt thereof.

15. The compound according to claim 10 wherein
$R^1$ is hydrogen;
$R^2$ is $C_1$-$C_4$ alkoxy - $C_1$-$C_4$ alkoxy or $C_1$-$C_4$ alkoxy - $C_1$-$C_4$ alkyl;
$R^3$ is $C_1$-$C_4$ alkyl or $C_1$-$C_4$ alkoxy;
$R^4$ is hydrogen;
X is methylene;
$R^5$ is lower alkyl;
$R^6$ is hydrogen;
$R^7$ is unsubstituted amino;
$R^8$ is branched $C_3$-$C_4$ alkyl;
$R^9$ is optionally substituted aryl-alkyl; or
a pharmaceutically acceptable salt thereof.

16. The compound according to claim 15 wherein
$R^2$ is 3-methoxypropyloxy;
$R^3$ is methoxy;
$R^5$ is isopropyl;
$R^8$ is isopropyl;
or a pharmaceutically acceptable salt thereof.

17. The compound according to claim 15 wherein aryl-alkyl is alkyl substituted with phenyl;
or a pharmaceutically acceptable salt thereof.

18. The compound according to claim 17 wherein aryl-alkyl is methyl substituted with phenyl.

19. A compound according to claim 18 wherein
$R^2$ is 3-methoxypropyloxy;
$R^3$ is methoxy;
$R^5$ is isopropyl;
$R^8$ is isopropyl;
or a pharmaceutically acceptable salt thereof.

20. A method for the treatment of hypertension comprising:
administering a therapeutically effective amount of the compound according to claim 1 to a warm-blooded animal in need thereof.

21. A pharmaceutical composition, comprising:
the compound according to claim 1 and
one or more pharmaceutically acceptable excipient(s).

* * * * *